(12) United States Patent
LaDue

(10) Patent No.: US 6,259,889 B1
(45) Date of Patent: Jul. 10, 2001

(54) ACTIVE SYMBOLIC SELF DESIGN METHOD AND APPARATUS

(75) Inventor: Christoph Karl LaDue, Santa Cruz, CA (US)

(73) Assignee: Symbix, Incorporated, Santa Cruz, CA (US)

(*) Notice: Subject to any disclaimer, the term of this patent is extended or adjusted under 35 U.S.C. 154(b) by 0 days.

(21) Appl. No.: 09/568,654

(22) Filed: May 10, 2000

Related U.S. Application Data

(62) Division of application No. 09/014,303, filed on Jan. 27, 1998, now Pat. No. 6,097,927.

(51) Int. Cl.[7] ................................................ G09B 5/00
(52) U.S. Cl. .................... 434/308; 434/310; 434/322; 434/323; 434/236; 434/238
(58) Field of Search ............... 434/308, 29, 30, 434/35, 38, 43, 46, 357, 236, 237, 238, 48, 49, 50, 51, 55, 59, 69, 219, 220, 226, 309, 310, 314, 322, 323, 324; 472/59, 60, 61, 64, 65, 68

(56) References Cited

U.S. PATENT DOCUMENTS

| | | | |
|---|---|---|---|
| 740,385 | * | 6/1903 | Bassell . |
| 3,901,215 | * | 8/1975 | John ................................. 128/2.1 B |
| 4,683,891 | * | 8/1987 | Cornellier et al. ............... 128/630 X |
| 4,913,160 | * | 4/1990 | John ................................. 128/731 X |
| 4,987,903 | * | 1/1991 | Keppel et al. .................... 128/732 X |
| 5,316,480 | * | 5/1994 | Ellsworth ............................... 434/29 |
| 5,320,538 | * | 6/1994 | Baum ................................ 434/307 X |
| 5,447,166 | * | 9/1995 | Gevins .................................. 128/731 |
| 5,469,511 | * | 11/1995 | Lewis et al. ...................... 381/173 X |
| 5,477,166 | * | 12/1995 | Matthews ............................ 326/38 X |
| 5,807,114 | * | 9/1998 | Hodges et al. .................... 434/236 X |

\* cited by examiner

Primary Examiner—Valencia Martin-Wallace
Assistant Examiner—Binh-An Nguyen
(74) Attorney, Agent, or Firm—Jeffrey A. Hall

(57) ABSTRACT

A method for behavior modification and memory enhancement utilizing a central processing unit, comprising compiling a symbolic profile of a subject participant, interpreting the subject participant's stored symbolic constructs, instructing the subject participant using virtual reality means, evaluating and recording physiological parameters of the participant and delivering symbolic containers to the participant; and delivering symbolic prescriptions to the subject participant for behavior modification and memory enhancement. The methodology allows for accessing and recognition of stored memory symbolic constructs by isolating symbolic quests embodied within multiple multimedia virtual reality events, and delivering the multimedia virtual reality events to a user by artificial intelligence and multi-media means, applying the symbolic constructs to the user. Apparatuses for behavior modification and memory enhancement, comprising devices for evaluating and constructing a symbolic profile of a subject participant, interpretative apparatus, virtual reality instruction apparatus for instructing the participant in behavior and memory modification, apparatus for evaluating and recording physiologic parameters of the subject participant and delivering symbolic containers to the participant and delivery apparatus for delivering symbolic prescriptions to the participant are included.

15 Claims, 22 Drawing Sheets

ACTIVE SYMBOLIC SELF DESIGN METHOD AND APPARATUS

CROSS REFERENCE TO OTHER APPLICATIONS

This application is a divisional application of and claims priority from patent application Ser. No. 09/014,303, now U.S. Pat. No. 6,097,927 filed Jan. 27, 1998.

BACKGROUND OF THE INVENTION

1. Field of the Invention

The present invention relates to methods and apparatuses designed to alter behavior and memory. In particular, the present invention discloses such a methodology which utilizes and combines apparatuses such as biofeedback machines, virtual reality systems, head mounted displays, holograms, tactile data gloves, body suites, wearable personal computers, and the like, for behavioral modification and memory enhancement.

2. Description of Related Art

There are numerous methods and apparatuses which have been disclosed that purport to create artificial behavioral modification environments. Devices such as immersion or isolation tanks have contributed to the myth of various so-called new age means and methods that are embodied in apparatuses such as brain machines, relaxation machines and other such 'suggestion software' technologies. The invention departs from all prior art brain machines, for it uses virtual reality or telepresence means that creates the illusion of being immersed in an artificial or mythological world, or of being present in a remote location in the physical world. The present invention may be described as a complete holographic "Mind Mirror" or psycosymbolic mind matrix self-design system.

To enter virtual reality (VR), a person puts on a head-mounted display (HMD), or enters the invention's 'Egg Room-consciousness simulator'. The HMD contains a pair of tiny television tubes, special optics and wide-angle lenses. There is also a device that tracks the position of the subject's head mounted in the HMD. When worn, the normal view of the outside world is substituted by a stenographic, three-dimensional computer graphics depiction of a 'world model' that exists in a computer, and is created by a high speed multitasking-computer based VR reality 'engine.' Besides being immersed in the artificial world, the subject is able to navigate within that world, and to manipulate it using hands and fingers and other body movements. Up until now VR has primarily been used for experimentation, medical instruction, entertainment and other commercial applications.

There has been some work towards a VR system that helps promote subject weight reduction by visual, and tactile reinforcement of various weight loss self talk or 'suggestive' reinforcement concepts. There has also been work completed towards of VR being used for interactive novels, role-playing games, fantasy games such as Dungeons and Dragons and other first-person role-playing related work that are structured in a multiform narrative style. The invention uses revolutionary role playing or psycho-dramatic immersion techniques, that in fact, change a person's behavior based on fundamentally modifying how he relates to past memory and life event trauma (LET).

The present invention is the first of its type to use VR and other technological means to initiate, stimulate and re-arrange symbolic memory material within the context of intense sensory immersion and realignment of how a person 'talks to himself' in the course of everyday life. The invention enables and provides a unique process that utilizes the symbolic-construct (SC) inventory that is stored in memory cluster material of the human brain. This symbolic construct (SC) material is retrieved by special technological means. Then it is uniquely re-arranged, re-constructed and fed-back to the patient in a 'mind mirror' metaphorical-symbolic-construct (SC) means and method. With ASSDM, the patient is truly a 'participant.' The participant in fact 'participates,' and directs the, construction of his own symbolic 'prescriptions.' ASSDM provides a total integrative therapeutic approach. This special self-directed approach is delivered to the participant via special artificial intelligence computers, televisor walls, VR hardware, software, and unique fully integrated ASSDM system control. The participant is able to explore his own specific life-event issues, and understand them in a more complete multi-dimensional holographic reality, and thus learn how to 'meta' or self-program around the 'embedded' psycho-symbolic obstacle, that in fact are his old life behavior scripts.

The invention's immersion method contributes to the creation of a receptive environment, for the cognitive realignment of human personality elements that are structured around key traumatic events. This realignment is enabled via the restructuring of symbolically connected 'life event' memory material. The invention provides the means to re-visit these events and therefore change one's holographic perception that encompass the negative significance of these events.

The invention utilizes many conventional VR apparatus, while adding new processes; via software, firmware, and hardware means. Additionally the invention uses other apparatus such as biofeedback machines, electroencephalograph or EEG systems, isolation tanks, and specially designed immersive room environments. For example, there has been work completed in the late 1980s that teaches a technique of causing music and sounds to play as a result of the automatic input of brain wave measurements from an EEG device. This technique demonstrates and effectively proves that the brain can act as an automatic electronic switch that can cause selected multimedia systems to respond during the invention's processes and procedures. However this prior art approach only tangentially touches upon the present invention's means and methods and desired results.

The invention couples key sensory input elements together to create a totally ground breaking approach. The approach completely stimulates and 'frees up' repressed memory, and causes a person whom becomes a participant, to truly assess the complete meaning of, a traumatic event that has had a profound impact upon his everyday behavior. The invention creates an interpersonal world that provides the means and methods for enabling a participant to really examine his internal feelings, which are caused by symbolic construct (SC) arrangements that are embedded in the participant's memories. These symbolic constructs (SC) govern a person's internal relationships with the self, and external relationships with other people and society-at-large.

These unhealthy behaviors are often the result of experiences that have been imprinted on our psyches during vulnerable moments when we were highly receptive or suggestible, particularly in childhood. What ever life event (LE) is transpiring during this suggestive state becomes imprinted as a 'truth.' These truths become an integral component of one's stored memory based symbolic behavior. These truths are not really true but become the fundamental behavioral template of life programs, that, we in fact 'believe' to be true without knowing we believe the program.

In Michael Hutchison's book 'Mega Brain Power,' Chapter Eighteen; Rescripting, Scripts and Imprints; pages 188 to 201, he relates, "All of us have certain chronic or recurrent states and behaviors we would like to change. Some of these may be harmful, self-defeating, self destructive, or habitual states and behavior patterns. Or they may simply be states or behaviors that we have found to be unfulfilling, or unrewarding, or that keep us from living up to our full human potential.

These unsatisfactory states or behaviors are often the result of experiences that have been imprinted on our psyches in moments when we were highly receptive or suggestible, particularly during childhood and early adolescence. Knowing what we do about mental imagery, and how the mind tends to work in terms of a progression of mental images, plus, being raised as we have been in a world of movies and television shows, it makes sense to speak of these internally guided behaviors as 'scripts.'

Many of our unwanted, harmful, or negative states and behaviors are the result of life event trauma (LET) conditioning. If we could remember those childhood experiences when the scripts were created, we could rationally go back and expose the script as the false creation it is. "Oh yes, I remember it well, I was three months old and I was just touching my penis. Well, Mommy was simply tired and became angry; that doesn't mean I'm really bad; that doesn't mean it's really naughty to experience sexual pleasure." However, it's extremely difficult to remember those childhood experiences. They usually remain unconscious, because they are state dependent or, even more resistant to memory, what the scientists call "state bound." The invention is designed to disrupt this 'state bound' condition, and re-arrange the behavioral template that it has in fact become.

There are many techniques known to those whom practice the therapeutic art that have varying degrees of success. Such techniques or 'mind tech methods' as neural linguistic programming (NLP); with it's imagery 'swishing techniques,' biofeedback related therapy, acoustic field generators, color therapy, flotation, and other related methods have had some degree of success. The invention provides the first truly revolutionary breakthrough for integrating prior art therapeutic techniques into a total hypertext, virtual reality immersive world, which creates a complete holographic reality, produced by the invention's artificial intelligence means, method and apparatus. The central problem with these prior art techniques is that they depend upon an individual's visualization abilities. In fact these prior methods fall seriously short of enabling and providing a truly effective means of reprogramming human consciousness. The invention provides the means and methods to suspend belief of prior programming. Then it enables a reconstruction of a new belief system, created by specialized firmware, software and hardware means that is fully integrated and controlled by the participant's physiological responses. These measured responses act as real time feedback that, through the invention's artificial intelligence means; further reinforces the participant's 'metaphorical-therapeutic-intent' that further serves to completely reinforce a new self- belief mythological system.

New mind technologies clearly provide the most effective tools yet developed for counteracting these deeply imbedded scripts. Like the body centered therapies, 'mind tech' works directly on the body-mind to slow brain-wave activity, activate the right hemisphere, and alter limbic activity such as breathing patterns. But new mind tools go far beyond the body-centered therapies by directly entraining and slowing brain-wave activity into the appropriate theta frequency range, effectively blocking out the distractions of normal life and the reminders of adult consensus reality. In terms of the using of acoustic field generators, flotation, and ganzfeld techniques, brain technology actively disrupts logical and customary adult thought patterns and injects the user into a whole-body nonlinear unpredictable reality. This experience triggers the emotional limbic brain to resonate and activate the mind-molecule web of information, and permit access to state-dependent and even state-bound childhood experiences.

In addition, brain technology permits the user or an associate to make use of the powers of hypnosis to, in Rossi's words, "access and reframe state-dependent memory." It is a process called "rescripting." The technique involves, first, the uncovering of the scripts, second, the creation of counter-scripts which present a more positive outcome, and third, the repeated presentation of the counter-script, preferably while in a deeply relaxed or hypnotic state. The L/S is used both to facilitate the uncovering and rescripting itself."

It is a primary object of the invention to release these 'states' that exist within or stored memory based programs, that are in fact linear and non-linear arranged symbolic constructs (SC) that we associate with our own scripted-mythological truths. These truths or programs are associated symbolic constructs (ASC). The invention provides non-associated symbolic constructs (NSC) that act as new programs or states. The invention provides symbolic quests (SQ) that are either programmed and planned symbolic quests (PSQ) or randomly selected and applied symbolic quests (RSQ) that are created via specially linked symbolic pathways (SP). Symbolic pathways (SP) are defined as a group of symbolic constructs that contain significant metaphorical content that relates to a specific psychological intent or goal. This metaphorical intent or goal is embodied in the specially selected symbolic constructs (SC).

These specially selected symbolic constructs 'contain' the desired metaphorical quality, due in fact to the special interrelationship between one or more symbolic construct (SC) to one another. The embodied metaphor can have universal-mythological connotations. The embodied metaphor can also have specific personal meanings that symbolize events in a given participant's life. These life event scenarios (LES) can have positive connotations or negative connotations. This connotative aspect relates to the 'intent' that is attached or 'contained' within each symbolic construct (SC), and the metaphorical connection between one or many symbolic constructs (SC). For example the intent or goal can be based on the participant's desire to release repressed memories. Once these memories are released then the metaphorical intent changes for the purpose of placing these memories in a more positive context in relation to the participant's present life goals. Therefore each symbolic pathway (SP) contains the metaphorical-therapeutic-intent of the participant. This special category of human intent or purpose is therefore contained within the special arrangement of the symbolic constructs (SC), thus creating unique symbolic containers (SCr).

The invention provides for eight or more linked symbolic pathways (SP).

When combined, the eight linked symbolic pathways (SP) create the desired symbolic quest (SQ). Each symbolic pathway (SP) can embody multiple symbolic containers (SCr). Each symbolic construct (SC) can have its own positive or negative polarity or quality. This quality relates to the participant's past life event scenario (LES), and or the goal of the participant in terms of his intention to change the metaphorical significance of a past life event scenario (LES).

These symbolic containers (SCr) contain associated symbolic constructs (ASC), and/or non-associated symbolic constructs (NSC), that are specifically delivered with the invention's artificially and technologically derived; ASSDM Multimedia Virtual Reality Events (AMV). These AMV events are completely created, governed, managed and delivered to the participant via the inventions unique artificial intelligence means, methods and apparatus. The invention provides symbolic containers (SCr) that become the embodiment of a person or participant's mental tool to extract the old program, and then rescript and reinsert a new program or script to live by. Each individual singular symbolic container (SSC) when joined together become a plurality of metaphorical symbols that when specially arranged and reconstructed to; fulfill a participant's metaphorical-therapeutic-intent; that in fact becomes the symbolic-embodiment comprised of; a plurality of symbolic constructs (SC). These specially arranged symbolic constructs (SC) create the metaphorical-polarity (MT) that is embodied in the symbolic containers (SCr) that in fact becomes a symbolic pathway (SP), that, when linked together create the desired symbolic quest (SQ)

The invention creates the full cognitive missing link and technical connection to a person's stored symbolic constructs (SC), which are in fact his memory clusters. The invention uses technical means to integrate a person's internal processes with; (1) present day behavior, (2) how it connects to dysfunctional behavior, and (3) how memory fabric governs both. The invention provides complete holographic symbolic quests (SQ), that, are linked together via the invention's artificial intelligence means. The invention's artificial intelligence means creates individual symbolic path workings or symbolic pathways (SP). These pathways are specially comprised and arranged symbolic containers (SCr) that are in fact constructed of 'symbolic constructs (SC),' that are used to revisit and transform life event traumas (LET), and other memories that shape present day attitudes about present day life experiences.

Human consciousness on all levels is intrinsically tied to how it interprets, quantifies and qualifies symbolic constructs (SC). From colors, to, familiar objects such as chairs, clothing, buildings, architectural styles, and mythological images. Natural elements such as trees, flowers, bodies of water and other familiar natural and man-made forms are also symbolic constructs (SC). Such personal symbolic constructs (SC) as body language, facial expressions, voice fluctuations, and vocal intonations. Such symbolic constructs (SC) as familiar music that triggers old memories, and familiar olfactory stimulators that trigger old memories, are used by the present invention to revisit memories and restructure them.

The invention utilizes all relevant symbolic elements, to reprogram a person's memory material, by re arranging its connotative relevance. The invention does not erase memory, ASSDM broadens its elements and creates an inner environment of consciousness flexibility.

The language of human cognitive processes, and the brain itself is comprised of symbolic constructs (SC). There are symbolic constructs (SC) that are associated, and those that have no present day direct association, to stored memory fabric. The invention provides terminology that clearly and directly connects to its unique technical processes and procedures. There are three main concepts that the invention utilizes. (1) Associated symbolic constructs (ASC), and (2) non-associated symbolic constructs (NSC) and symbolic containers (SCr). These terms represent the multilayered complex concepts that are connected to the processes and procedures that make up the dynamic framework of human cognition and behavior.

A basic example of associated symbolic constructs (ASC) relates to observed phenomenon that is familiar, such as driving your own automobile down a familiar road near your home town. The trees along the roadside are familiar, the lake in the back ground, the sky is blue and other related experience. An example of a non-associated symbolic construct (NSC) is as follows. Say you travel to China, nothing is familiar: the people, the topography, physical landmarks and other such phenomenon. Except in fundamental ways, there is not much that you are familiar with. Another example is like all of a sudden waking up on another planet where familiar physical laws and cultural do not apply to your prior experience.

Even though all human facial expressions and body languages have universal significance, a mother's facial expressions have singular significance to the child of that mother. No one else can relate to and experience his mother's facial expressions like that child. The child then grows and matures to adulthood. The adult walks down the street, and passes a woman whom has a facial expression that triggers a memory of his mother's approving or disapproving facial expression. In another related scenario the person's supervisor can remind him of his mother, because of her demeanor, facial shape, voice, body language and other factors.

Because of earlier experiences he can in fact 'act out' behavior that is based upon earlier trauma that occurred with the mother and transfer it to the boss. Depending upon the significance of the memory, this encounter can shape the person's perceptions of other associative symbolic constructs (ASC), i.e. encounters with other people that relate to this particular memory stored symbolic construct (SC). This encounter can effect his feelings either positively or negatively throughout the remainder of the day, even without him consciously recognizing the effect of the ASC in connection with the prior-stored memory based (SMB) SSCs.

The invention embodies an innovative approach to applying symbolic manipulation means and methods within the framework of artificial intelligence means via computer hardware, firmware, and software. The invention utilizes head-mounted displays, body suits, natural environment simulators, and other conventional apparatuses in a unique and innovative ways. Other graphic and cinematic based media are used by the invention.

Additionally, the invention applies a unique use of retrieved neural signal inputs, various computer input systems, and programs that control what symbols, visual sequences, cymatic sound, music, and tactile stimulation means to be applied to the instant ASSDM immersion experience. Devices such as tactile transducers and other 'vibratory apparatus' are used unique by the invention. The invention also provides for full integration of biofeedback systems, electroencephalogram (EEG), and other related apparatus used for psychometrics and human physiological system measurements. These psycho-biological measurement systems are used by the present invention to measure key 'metaphorical tension' that is produced within the consciousness of the participant while immersed in the inventions means and methods.

There are apparatuses and procedures that teach how to control computers with neural signals. These apparatuses enable the use of electrical impulses from nerves and muscles, and how they can command computers directly. These prior art methods also teach that by using eye movements, based upon visual input from observing a computer screen that are monitored via by measuring signals in the brain, a handicapped person can communicate with the rest of the world. The invention uses a completely improved approach to these technological means and method

SUMMARY OF THE INVENTION

To achieve the foregoing objects, and in accordance with the purposes of the invention as embodied and broadly described herein, an artificial intelligence means and method that provides software, firmware and hardware control of selected integrated apparatus, which enable, a completely innovative approach to human behavior modification. The invention provides a preprogrammed and automatic insertion of specially created symbolic quests (SQ) that have embodied metaphorical symbolism that creates psychological tension and change.

These symbolic quests (SQ) can take the linked multimedia formatted and pre-planned artificially programmed symbolic pathways (SP) that are linked together via artificial intelligence means to create; programmed and planned symbolic quests (PSQ), and/or randomly applied symbolic quests (RSQ), that embody manipulated symbolic-containers (SCr), that are constructed of specially designed and formatted symbolic-constructs (SC).

These carefully arranged symbolic constructs (SC) enable cyber-psycho-symbolic-sequences that re-enact and integrate individual personalized experiences; via an assortment of artificially constructed and applied human sensory input means. The invention provides these symbolic quests (SQ) that embody narrative and non-narrative sequences that are specially arranged cyber-psychodramatic scenarios that are comprised of specially selected symbolic containers (SCr).

The symbolic container (SCr) is in fact a special arrangement of key metaphorical symbolic constructs (SC), that in fact create a 'numinous tension' within the consciousness of the participant by providing crucial 'metaphorical polarity.' This 'metaphorical polarity' is embodied with the narrative structure of the symbolic quest (SQ) which are specially linked symbolic pathways (SP), that embody a plurality of linked symbolic containers (SCr) that are created from the special arrangement of key symbolic constructs (SC). These symbolic containers (SCr) are metaphorically structured to provide an intense paradoxical conflict within the consciousness of the ASSDM participant.

A primary object of the invention is to provide software and firmware means that enables randomly programmed and applied symbolic quests (RSQ), and planned and programmed and applied symbolic quests (PSQ). Said symbolic quests (SQ) are stored in the inventions ASSDM multimedia virtual reality (AMV) transport, and symbolic quest storage apparatus. These apparatuses include computer digital hard drives, static memory, digital video disc (DVD), compact read-only memory disc (CD-ROM), recordable digital discs, digital video tape decks (DV), digital audio sampling storage and sound segment delivery systems. Said applied symbolic quests (SQ) are delivered to the participant via the analysis of artificial intelligence means embodied in one or more main ASSDM system main computers, media computers and private personal computers (PPC) that are connected to a centralized control management hub called the ASSDM cyber center. This specialized cyber center is connected to private personal computers (PCC) via the internet world wide web (WWW). The inventions cyber center expands the inventions means and methods to a worldwide bases, where anyone, anywhere can access, participate and benefit from immersing himself in the invention's means and methods.

At a centralized ASSDM facility, upon command initialized by an ASSDM facilitator, the main computer accesses a plurality of data files that contain unique digital instruction sets. These instruction sets cause the main computer(s) software to select eight or more separate symbolic pathways (SP), that are individually created and arranged 'metaphorical paradoxical stories.' These mythological stories are in fact embodied in selected symbolic containers (SCr) that are comprised of multiple symbolic constructs (SC), that are delivered to the participant's sensorium via linear and multiform montage cinematic narrative and non-narrative techniques. Said symbolic constructs (SC) can also be delivered in non-linear, abstract-spatial relationships that cause a plurality of human conscious responses based on the law of psychological paradox and the metaphorical tension created by the symbolic paradox embodied in the inventions technological processes and procedures.

This aforementioned input phenomenon is the core of the invention's ASSDM multimedia VR technological event (AMV), which embody the invention's symbolic quest (SQ) means and methods. Said symbolic quests (SQ) are the core sensorial fabric of AMV events that include but are not limited to; designed and scripted virtual reality-cinematic-sensory immersion sequences that are; designed non-linear cinematic-symbolic constructs (SC) that include; orchestrated-integrated; cymatic sound arrangement, music, tactile-kinetic vibrations, filmic vignettes, and psycho-symbolic sequences that create the desired 'metaphorical tension.'

The participant is directly interfaced with; computer displays, HDTV systems, 3-D holograms, head-mounted displays (HMD), body suits, tactile data gloves, body position controls, olfactory stimulators, tactile transducers, computer displays, projection screen television, flight simulators, the inventions egg room, and the delivery of the event to the participant's sensory experiences in order to create the desired 'metaphorical tension.' The invention also provides the means and methods for orchestrating preprogrammed algorithms that automatically control the impacts of the AMV event via its sensory intensity and the desired symbolic-thematic content that embodies the desired 'metaphorical tension.' These specialized processes and procedures can occur at a specially constructed ASSDM psycho-symbolic ASSDM facility, and or, via the internet world wide web (WWW) and the participant's private personal computer (PPC).

A primary object of the invention is to provide sensory experiences that are artificially recreated to emulate and approximate past traumatic memories contained within a designated AMV event; for the expressed purpose of re-experiencing said memories in order to reassess the impact of the particular related traumatic event. These traumatic memories are released and triggered by the inventions 'metaphorical tension,' embodied in the inventions programmed and selected symbolic paradoxes by the inventions artificial intelligence means.

Another related object of the invention is to provide statistical measurements of the psycho-biological impact of the AMV event in the context of the participant's experience of 'metaphorical paradox.' These measurements are detected, retrieved and used in real time control by artificial intelligence means of; exactly what type of psycho-symbolic experience that is embodied and designated by the symbolic quest (SQ). This symbolic quest (SQ) is comprised of multiple symbolic pathways (SP), that are linked by the content of the embodied symbolic container (SCr), that are comprised of metaphorically linked symbolic constructs (SC); that are created by the inventions artificial intelligence means, that in fact creates the embodied AMV event. These AMV events can be experienced at a specially designed and constructed ASSDM psycho-symbolic therapeutic center or via the internet world wide web (WWW), the invention's cyber center and the participant's private personal computer (PPC).

Furthermore, the invention selects computer based artificial intelligence means; that control and monitor, and statistically evaluate psycho-biological measurements that include; Alpha, Beta, Theta, Delta and Mu brain waves, and occipital lobe flash rates, and heart-pulse rates, that are measured by; electroencephalogram (EEG), galvanic skin response (GSR), human nervous system based frequency modulation (FM) radio signals, electroocular-symbolic pulses, emitted from the human nervous system, and the brain's occipital lobe, and muscle tissues. The aforesaid measurements directly influence control of the selection of specialized AMV event content. This event content is created, preprogrammed and selected via multi-media computer intelligence means of just how, and, by what medium, the embodied symbolic quest (SQ), that is comprised of multi-linked symbolic pathways (SP), that in fact embody specially created and linked symbolic containers (SCr), that are comprised of specially selected symbolic constructs (SC), that must be applied to the participant's senses; while immersed in a complete ASSDM Stage experience; in order to achieve the desired 'metaphorical tension.' Also, the invention measures exactly what level of sensory intensity the participant can tolerate while experiencing AMV event immersion-sensory-stimuli techniques.

Another object of the invention is to provide unique computer hardware and software based systems that automatically insert the aforementioned AMV event as result of the response that is automatically attuned to specific types of psychometric- and physiological measurements. These measurements include but are not limited to biofeedback analysis of brain wave states, and optical analysis of eye-cornea-retinal activity while the participant is immersed in the AMV environment. This specially measured and applied cornea-retinal activity result in the invention's special electrooculosymbolic signal measurements. The invention modifies this conventional electrooculographic means and methods, and transforms these conventional methods to create complete revolutionary electrooculosymbolic means and methods. These measurements derive from 'flashes' that transpire during the corneal reflex; and the voltages that are generated between the retina and cornea and sent to the occipital lobes of the brain via synaptic and neuron circuitry that are recorded as EEG traces.

The peak electrooculosymbolic measurements can be used to pinpoint exactly what symbolic construct (SC) contained within a linked and selected symbolic container (SCr), that is contained and linked to a symbolic pathway (SP), that is embodied in a selected symbolic quest (SQ) and delivered to the participant via a designated AMV event. The participant immerses himself within this AMV hypertext event ,and focuses his attention to the symbolic constructs (SC) and symbolic containers (SCr). Depending upon what level the 'metaphorical tension' has been attained within the psychological and physiological reactions of the participant; the effect results in, and is aligned with, the desired metaphorical-therapeutic-intent. This measured reaction can indicate that additional associated symbolic constructs (SC) must be introduced to the participants senses immediately via; visual, and/or auditorial, and/or tactual, and/or olfactory, and/or tactile-position, and other means.

Participant brain activity is measured in detail while experiencing 'metaphorical symbolic tension.' Participant brain waves are carefully mapped. These waves are currently defined as alpha waves, beta waves, theta waves, delta waves and mu waves. The invention utilizes conventional electroencephalogram (EEG) systems in unique and innovative ways. EEG systems can be used to track the activity of the five categories of brain waves. Metabolic measurements of participant's breathing rates, measurements of heart beat rates, measurement of pulse, and measurement of muscle stress.

It is another object of the invention to provide the means of collecting the aforesaid measurements, and store and process the measurements in such a way as to create a unique statistical engine. This statistical engine in turn provides data to the inventions artificial intelligence means that governs the symbolic-construct (SC), symbolic container (SCr), and symbolic quest (SQ) output of the ASSDM apparatus during an AMV event. This AMV event is the physical embodiment, which contains the invention's psycho-symbolic process. These processes are therefore created by the special arrangement of symbolic constructs (SC), that are embodied in the invention's symbolic container (SCr), and are further embodied in the inventions symbolic pathway (SP) that create and comprise the invention's symbolic quest (SQ).

It is another object of the invention to provide individual symbolic quest (SQ) 'prescriptions' for home or office use. These symbolic quest (SQ) prescriptions are carefully constructed multiple AMV events that can be delivered via digital videodisc (DVD), compact disc read only memory mediums (CD-ROM), videotapes and laser disc (LD). Furthermore these individual symbolic quest (SQ) prescriptions can be delivered to individual participants via the internet and their personal computers. These computers are located at home or at the office. The participant can be supplied with the inventions 'consciousness machine' (CM) that is a specially created VR based portable or wearable system that includes; HMDs, televisors, data gloves, audio headphones, wireless EEG transmitters, and wireless EEG receivers. This system is provided so that a remote immersive AMV experience can be enabled away from the main ASSDM facility.

Another feature of the inventions conscious machine (CM) is that it embodies special wireless communications means. Such wireless networks as cellular, personal communications (PCS) systems, and satellite networks can deliver text messages, real time video images, still video images, sound and other psycho-symbolic programming means. Furthermore the invention provides for subdermal sensors that communicate with special wrist and legbands, that are communicatively linked to the consciousness machine (CM) via radio waves and other wireless means. These sensors can be used to monitor blood content; such as sex hormones, adrenaline, drug levels, alcohol levels and other metabolic data.

Another important object of the invention is to provide an internet based cyber-psycho-symbolic (CPS) interactive system. This CPS interactive system comprises of the specially programmed private personal computer (PPC) that are linked via the inventions multi-media cyber center via the internet world wide web. The cyber-center is the central hub for providing real time video interactive sessions that embody the inventions specialized psycho-symbolic means and methods. Furthermore, the invention provides unique cyber-psychodramatic therapy whereby; multi-participant's from around the world can engage role playing for acting out issues that are tied to internal mythologies; facilitated by a trained ASSDM therapist facilitator.

The facilitator can be either a real person, or a computer generated based character. The human facilitator can don many computer generated psycho-symbolic 'masks' from an archetypal-mythological character to a wild animal; whatever is symbolically necessary to achieve the desired psycho-symbolic goal or theme. Furthermore, the invention can provide for participant 'morphing' of archetypal masks for his own psychological benefit, as well as the other participant's benefit during a cyber-symbolic session in real time. Another object of the invention is to record these real time multi-participant sessions, archive them and then reuse these in real time sessions for other ASSDM multi stage purposes.

Additional objects and advantages of the invention will be set forth in part by the description that follows, and in part will be obvious from the description, or may be learned by practice of the invention. The objects and advantages of the invention will be realized and attained by means of the elements and combinations particularly pointed out in the appended claims.

BRIEF DESCRIPTION OF THE DRAWINGS

The accompanying drawings, which are incorporated in and constitute a part of the specification, illustrate a preferred embodiment of the invention and, together with a general description given below and the detailed description of the preferred embodiments which follows, serve to explain the principles of the invention.

FIG. 2 is a depiction of the ASSDM multi-participant screen and video conference center, according to the invention.

DETAILED DESCRIPTION OF THE PREFERRED EMBODIMENTS OF THE INVENTION

Figure 1:
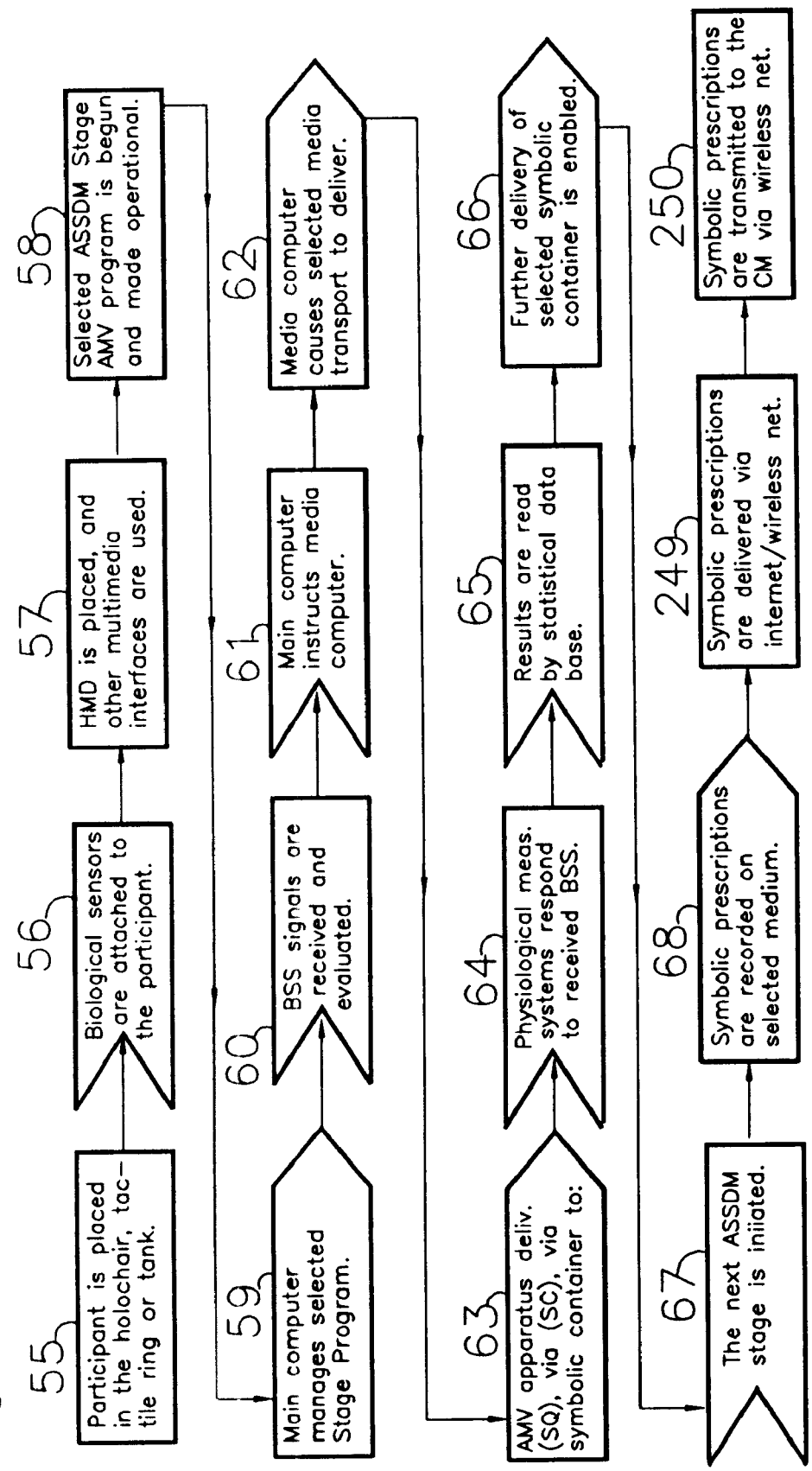
FIG. 1 is a block diagram of the systems holographic protocol according to the invention.

Reference will now be made in detail to the present preferred embodiments of the invention illustrated in the accompanying drawings. In describing the preferred embodiments and applications of the invention, specific terminology is employed for the sake of clarity. However, the invention is not intended to be limited to the specific terminology so selected, and it is understood that each specific element includes all technical equivalents, which operate in a similar manner to accomplish a similar purpose.

Accordingly, there is provided a method, a means and apparatus for accessing and discovering significant stored human memory based symbolic constructs (SC), by supplying carefully designed symbolic quests (SQ) that are embodied within multiple; ASSDM Multimedia Virtual Reality (AMV) events, that are embodied within the invention's multi-stage processes and procedures. These AMV events are delivered to the participant's senses by artificial intelligence means, and specially selected multi-media based apparatus. Furthermore, once stored human memory based symbolic constructs (SC) are discovered, the invention applies completely relevant artificially created symbolic constructs (SC) to the senses of a human participant while immersed in the inventions means, methods and apparatus.

These artificially created, orchestrated and applied symbolic constructs, that are embodied within symbolic containers (SCr), that are further embodied within designated symbolic containers (SCr), that are technologically embodied within the invention's AMV events. These AMV events are designed to cause the participant to experience his own past life event issues in a completely different context, and then redefine, and therefore reprogrammed so that the psychological significance of these events can be understood and placed in proper psycho-symbolic context.

Additionally, new symbolic construct (SC) information can be inserted during key periods of psychological vulnerability that is revealed by automatically measuring biological sensor signals (BSS). Furthermore these BBS signals are technically integrated to become 'cues' reported by the invention's physiological measurement means and methods. These measured cues therefore directly control the invention's electronic cues that are detected by the inventions main computers, control the multi-media transport and storage systems that deliver the invention's AMV events.' Said electronic 'cues' are embodied within the invention's symbolic quests (SQ) that are comprised of multiple AMV linear and non-linear event sequences. Typically linear AMV event sequences are comprised of narrative symbolic quests (SQ) and abstract or surreal non-narrative symbolic quest (SQ).

These AMV event sequences can be comprised of cinematic style linear-narrative stories of the self. The invention provides the means and method of immersing the participant in the holographic reality of an 'other world' event sequences, that may or may not relate to real life event (LE) scenarios. Additionally, the invention provides for the means and methods of immersing the participant in cinematic style linear-narrative stories that may cause the participant to revisit life event traumas (LET). Furthermore, the invention provides for the means and methods to construct new artificially derived life event scenarios (LES) that are embodied within randomly selected symbolic quests (RSQ). The invention also provides for the means and method of providing new artificially derived life event scenarios (LES), that are embodied within carefully selected and planned symbolic quests (PSQ).

Once the past life event issues are re-experienced, the invention is therefore used to create new symbolic construct (SC) based mythological stories also known as symbolic quests (SQ) that become self-programmed multiple AMV event scenarios. These symbolic quests (SQ) can be configured and delivered in a planned and arranged symbolic quest (PSQ), or a randomly arranged symbolic quest (RSQ). These symbolic quests can be arranged by the participant or by an ASSDM facilitator. Once created, these new artificially derived stories are applied to the senses of the participant in linear and non-linear multi-sensory stimuli formats that are embodied in selected AMV event scenarios. These symbolic quest (SQ) are enabled via specific firmware, software and hardware means that are embodied in the inventions methods and apparatus that in fact create the desired AMV event that are embodied in selected symbolic quests (SQ).

These artificially derived symbolic quests (SQ) are created and orchestrated uniquely for each participant. These unique stories in effect become AMV event symbolic construct 'prescriptions' that can be downloaded to digital video disc (DVD) formats, compact disc (CD) formats, video tape formats and other mediums. Once downloaded or recorded, the prescription embodied in conventional multimedia storage and transport mediums and is given to the participant to take home and replay and re-experience as an act of positive reinforcement whenever needed. These symbolic quest (SQ) prescriptions can be delivered to the participant via his own personal computer, the computer video display and the internet world wide web (WWW). Furthermore, the participant can use his personal computer along with portable head mounted displays (HMD), data gloves and other virtual reality means at his home or office as a further means of positive reinforcement of the invention's means and methods while on-line with the internet.

The participant can also subscribe to the invention's means and methods via the internet once he has completed the multistage, ASSDM means and methods at a specially designed ASSDM institute facility.

The invention also measures the data retrieved from biological signal sensors (BSS). This data is automatically entered into a specially designed statistical engine database (SED), which communicates with the main computer. A designated ASSDM Stage session, in fact embodies; multiple symbolic quests (SQ), that embody multiple AMV events, which in fact embody; multiple symbolic pathways (SP) that contain multiple symbolic containers (SCr), and which in fact embody; multiple symbolic constructs (SC), which in fact embody; associated symbolic constructs (ASC), which in fact embody; non-associated symbolic constructs (NSC), which in fact embody; singular symbolic constructs (SSC). Whereas, these different categories of symbolic quests (SQ) that contain specialized AMV event sequences, can in fact contain special combinations of combined ASCs, NSCs, and SSCs. That these combinations can be linear logically based, or non-linear intuitive based. That these AMV events can also contain the invention's modified REM means and methods.

The collected BSS data is analyzed by the main computer and various statistical reports are compiled and produced that may result in specific automatic and or manually induced AMV event actions to occur in accord with main computer and media computer algorithms and protocols. These AMV event actions contained with specialized symbolic quests (SQ) therefore occur as a result of the report of this comprehensive BSS analyses.

The main computer's actions include but are not limited to the following scenarios. (1) Applying relevant symbolic quests (SQ) that contain selected AMV events that embody specific symbolic containers (SCr) that contain specific symbolic constructs (SC), and are applied to the senses of the participant while he is totally immersed in the invention's artificially constructed holographic virtual reality AMV event environments. These AMV events are carefully orchestrated, and then applied to the senses of the participant as a result of specially configured firmware, and software based apparatus instruction sets that are sent to the media computer from the main system computer.

(2) That these artificially derived symbolic quests (SQ) that contain selected AMV events, are specially designed to relate to the participant's life experiences from early childhood to the present day. (3) That these artificially produced and delivered symbolic quests (SQ) that contain specialized AMV events can cause the participant to become fully aware of past issues and therefore revisit and discover the true relevance of a particular event or group of associated events. (4) That these artificially produced symbolic quests (SQ) that contain selected AMV events can cause the participant to discover his own inner symbolic mythology, or symbolic landscape and therefore learn how to recreate a new more effective inner mythology that enables a better way of experiencing and coping with present day life issues. And (5), during an immersed ASSDM Stage session, that in fact embody selected symbolic quests (SQ) that contain selected multi-AMV events, that further embody multiple symbolic containers (SCr), that in fact embody multiple symbolic constructs (SC). Whereby these symbolic constructs (SC) can be associated symbolic constructs (ASC), non-associated symbolic constructs (NSC), and singular symbolic constructs (SSC), the desired metaphorical-therapeutic-metaphorical intent can be achieved.

The physiological reactions of the participant can be measured and the specific results can cause the main computer to instruct the media computer to select which combinations of the media system and its associated delivery format is to be applied to the participant's senses via a selected AMV event. A selected symbolic quest (SQ) that embodies multiple AMV events creates an artificially derived life event scenario (LES). This LES is embodied in a specially derived symbolic quest (SQ) that can be sent from the invention's multimedia storage and transport systems, that are controlled and managed by the invention's specially designed main computer, to a head mounted display (HMD) or other selected AMV apparatus via the ASSDM facility network, or via the internet world wide web (WWW). The HMD in fact projects and immerses the participant in a three dimensional reality along with other VR apparatus such as a body suit, data glove, tactile ring, holochair or flotation tank, televisor, and the invention's wearable consciousness machine (CM).

The invention's multi-dimensional symbolic quests (SQ) that contains selected AMV event information, is supplied by a DVD video and audio system, and/or a videotape deck source, and/or a CD-ROM source, and/or digital video source, and/or audio from a digital sampling source, and/or tactile vibrations delivered via tactile transducers, and/or olfactory stimulators sent from an associated apparatus. The invention's artificial intelligence means controls exactly how, it is to be applied to the senses of the participant while seated in the inventions holochair, or suspended via the inventions tactile wheel. These multi-media systems are used to select which of the invention's artificially designed singular symbolic containers (SCr) or multiple symbolic containers (SCr) are to be applied to the participant's senses. These symbolic containers (SCr) act as possible life event simulations (LES) that occur during the experience of the invention's specially designed symbolic quests (SQ).

The invention's artificial intelligence means can cause an automatic shutdown of a symbolic quest (SQ) that contains multiple AMV event experiences, when the reported condition of the participant's physiological system warrants such an action.

The invention's method preferably encompasses seven levels or stages of participant analysis, psycho-symbolic evaluation, and symbolic quest (SQ) immersion means and methods. Stage One also known as the 'Mind Method,' involves the act of compiling a comprehensive symbolic-profile of the participant during a one-on-one session with a specially trained symbolist-therapist. In traditional 'talk therapy' sessions a patient tends to deal with chronicles of life event issues through discussing the events in terms of what was said, what transpired and who did what to whom.

The present invention provides the means to enable a unique process that departs from 'talk therapy' techniques. What is not normally talked about in conventional therapeutic sessions is the life event environment. An ASSDM trained facilitator-therapist is primarily a 'symbolist.' The facilitator-symbolist can compile what is essentially a symbolic inventory, and therefore 'peer' into the participant's life event (LE) memory material. For example, when an early traumatic event occurred, how did the instant LE holographic environment 'feel?' What was 'seen,' and 'heard?' How was the participant touched by significant others? What smells were prevalent? What facial expressions were dominant? What was the symbolic significance of experienced facial expressions? What type of body language was exhibited during this particular life event (LE) issue? Where did a particular life event transpire? Did it unfold inside of a particular building? Did the life event transpire outdoors in a forest, or near the seashore? What dominating symbolic factors existed when this life event occurred?

By exploring these LE symbolic aspects, memories that are repressed or buried in the psyche can be brought to the surface and examined. What recurrent dream themes seem to be prevalent? What symbolic constructs tend to dominate the participant's dreams? Stored memory (SC) Information can also be derived from understanding the significance of his cultural origins, and how those origins influenced the participant's early childhood.

The invention's means and methods enable the release of memory material that is composed of different types of collected and compiled symbolic constructs. By applying artificially composed relevant symbolic constructs, that are embodied in selected symbolic containers (SCr), that take place during a symbolic quest (SQ) that contain multiple AMV events; memory based symbolic constructs that are the details of life event issues can be released into the levels of conscious thought. These artificially derived symbolic containers (SCr) embody symbolic construct (SC) 'triggers' that enable the participant to 'revisit' the specific memory or memory cluster and learn to better cope with its initial impact. Adults can therefore revisit childhood memories and place the relevance of these memories into the context of mature critical thinking and feelings based upon a lifetime of experience. Therefore, Stage One enables the symbolist-therapist to compile a complete symbolic inventory of a particular participant. Once this is accomplished the next stage of the invention's method can commence. The invention's Stage One means and methods can be completely facilitated via the inventions cyber center, the internet world wide web (WWW), the participant's private personal computer (PPC) and or the participant's consciousness machine (CM).

According to psychiatrist Rollo May symbols are specific acts or figures while myths develop and elaborate these figures into a story of the self. Questions about resident, memory based symbolic 'self-concept-myths' can help the participant discover and experience a greater reality in the outside world. By drawing out the inner landscape via symbolic quests (SQ) answers about the self can be realized. The invention embodies these myths within the context of it's symbolic quests (SQ). Symbolic quests can be created to discover the participant's current mythologies. Furthermore, symbolic quests (SQ) can be created and applied for the purpose of inserting a new mythology of the self within the perceptions of the participant. In a broad sense, this aspect can be compared to how and improved software revision for a computer is utilized, for sometimes a computer's resident operational program has to be upgraded.

The present invention enables a person to upgrade his own 'operational program.' This 'human operational program' is embodied with the feelings, the self-talk, and the self-view that we perceive or believe the self to be. We carry these beliefs around with us while conducting our everyday life. This 'operational belief program' is in fact the core of our personal mythology. It is a primary object of the invention to enable a technological means to first discover one's inner mythology. And second, to enable a technological means and method to construct a new inner mythology.

People do not act according to logical principles but according to the myths or internal 'self-talk' stories that we believe about ourselves. In Stage Two for example, also known as the 'Mind Map' phase, the facilitator assists the participant in the process of discovering his inner mythological landscape. During this act of this discovery, various stored memory based symbolic constructs emerge.

This symbolic construct 'emergence' or realization is activated or 'triggered' by the invention's means and methods. These means and methods are embodied in the invention's symbolic quests (SQ) that are derived from uniquely configured firmware, software, and hardware.

During Stage Two the participant's internal 'myths' are 'read' in that the myths reveal a functional or dysfunctional 'picture language' that is composed of stored memory based symbolic constructs (SC). The participant's stored symbolic constructs are mapped in a way that causes the participant to 'react' and have those reactions measured. The invention's Stage Two can be completely enabled via the invention's cyber center, that is connected to the internet world wide web (WWW), and the participant's private personal computer (PPC) and or his consciousness machine (CM).

In Stage Three the participant is instructed in the meaning of symbols, archetypes, connotative imagery, cymatic theory and other relevant information. The participant is taught the significance of the different categories of ASSDM means and methods. The participant also attends classes that deal with the meaning of archetypal symbols, mythological symbols and the meaning of his own symbolic constructs (SC). An important element of the ASSDM experience is based upon how well a participant understands the meaning of the various symbolic and technological techniques that are embodied in selected ASSDM Stages. Like previous stages, Stage Three can be enabled and accomplished via the invention's cyber center, the internet world wide web (WWW) and the participant's private personal computer (PPC).

In Stage Four the participant is exposed to a randomly composed symbolic quest (RSQ). The composition of this RSQ is based upon an arrangement of eight or more selected AMV events that encompass multiple symbolic containers (SCr) that reflect ancient and contemporary archetypal symbolism. Embodied in this symbolism are key sequences that further contain symbolic 'cues.' These cues contain symbolism that reflects the individual participant's cultural preferences. Additionally, stage four sequences contain symbolic sequences that reflect the individual participant's other more personal familiar symbolic preferences. Therefore, in this way a symbolic-therapeutic-agenda is created. During the processes and procedures of Stage Four, further discovery is made concerning the participant's symbolic 'hot points.' These symbolic hot points are recurrent symbolic motifs that contain and project images, sounds, music, vibrations and other sensory stimuli that tend to 'trigger' or release buried memories, feelings and certain intense reactions to the Stage Four means and methods. These 'symbolic trigger' are symbolic containers (SCr) that are key archetypal symbols that may have personal significance to the participant.

During this stage, the participant is exposed to many different types of 'symbolic trigger-containers.' The participant's reactions to the exposure of these key 'symbolic triggers.' Are measured by the inventions means and methods. Furthermore an ASSDM facilitator monitors the participant's reactions, and evaluates the significance of these reactions. Even if a participant is not aware of his agenda, this process helps to in fact discover and codify one. This stage can only be experienced while immersed in the invention's AMV apparatus at a specially designed ASSDM psycho-symbolic therapeutic center.

In Stage Five the participant becomes an active designer of his own planned symbolic quest (PSQ). The participant and the facilitator work jointly to create a symbolic quest (SQ) that reflects the desired result of the participant. He may want to deal with certain childhood issues, relationship issues with his spouse and other important aspects of his life. During the processes and procedures of Stage Four, and Stage Five, intense memories of traumatic life event trauma (LET) events will emerge. The participant now submits to the processes and procedures of Stage Six. Stage Five can only experienced at the invention's ASSDM psycho-symbolic therapeutic center.

In Stage Six the participant is immersed within the processes and procedures of the invention's AMV-REM event means and methods. In this stage the symbolic quest (SQ) evolves to a combined instructional and experimental phase. For example in Stage Six the participant is again taught that a symbolic construct (SC) is a concept that embodies the complete totality of human perceptual experience. That during the preceding stages, the participant has become quite familiar with his own internal mythology. The participant discovers that the totality of human experience is embodied within the essential self of each individual. Certain aspects of his own mythology may be governed by key traumatic events. During Stage Six the participant will work with the facilitator to construct a combined non-linear abstract symbolic reality, that is coupled with key narrative AMV sequences. The participant may want to revisit memories about a parent, a spouse, a sibling or other significant person whom may have had a profound impact upon his life.

The invention provides unique means and methods of creating psycho-symbolic sequences that have intense similarities to past events. Even such aspects as re-experiencing a significant person's facial expressions, vocalizations, dominant body language and other key factors. The invention provides for special computer generated images that enable specialized recreations of the face and body of a significant person. Various morphing techniques are used for this purpose.

A participant may be able to simulate a conversation with a deceased parent or other person. Finally, the person may be able to conclude issues that have hindered him all of his life. Interspersed with this psycho-cinematic technique are sequences that contain key symbolic constructs (SQ). These symbolic constructs are in fact symbolic containers (SCr) that enable a rearrangement of memory based symbolic construct material that is relevant to the particular morhphing techique that is transpires during a Stage Six process and procedures. Stage Six also embodies a unique process that enables the participant to become his own symbolic container (SCr). Special symbolic quests (SQ) are created that depict the participant as the main character in his own transformative journey. He can become the Christ, or the Buddha, or Krishna, or Sir Gawain of the Arthurian Legends. The participant can therefore discover his own worthfulness. The participant becomes one with the symbolic container (SCr), and in fact becomes the symbolic container (SCr) and its transcendent power. The participant discovers his own unique power to transform the self. The invention's technological means and methods enable this process in a complete innovative way that has never been taught or specified by any other technology. Stage Six can only be experienced within the invention's specially configured AMV immersive hypertext apparatus that is located at a specially designed ASSDM psycho-symbolic therapeutic center.

Stage Seven enables a real time video and audio access to the present invention's cybercenter, and its cybersymbolic psychodramatic programs, process and procedures. The participant can only access these special multi-participant real time interactive programs via the internet, after he has experienced and passed through the invention's Stage Four, Stage Five and Stage Six at a specially designed ASSDM psycho-symbolic therapeutic center.

Stage Eight is reserved for research, development and experimentation. The ASSDM means, method and apparatus is in a constant state of evolution. This stage deals strictly with new processes and procedures that will be embodied by the inventions means and methods in conjunction with utilizing Federal Drug Administration (FDA) approved smart drugs, such as cognition enhancers and other such substances.

All stages of the invention therefore reinforce the fact that human perception is essentially an interior experience, and that all anterior, or external experiences can be viewed as compilations of multi-level holographic symbolic constructs (SC). The participant is taught that an associated symbolic construct (ASC) is a class of symbolic construct that has connotative and denotative significance to the participant's accumulative life experience and therefore relates to the participant's prior experiences in life. Anything that is embodied in symbolic phenomenon that a participant is even remotely familiar with is an associated symbolic construct (ASC). The invention provides for ASC's that can be in fact life event simulations (LES) embodied in symbolic quests (SQ) that embody AMV event sequences or groups of sequences that contain key symbolic containers (SCr). These symbolic quests (SQ) that embody AMV events are delivered via AMV apparatus, and stored, selected and transported by DVDs, CD-ROMs, videotapes, laser discs, digital storage devices such as computers, digital video effect systems, audio samplers, and other digital and audio systems.

The delivery of the selected symbolic quests (SQ), is managed by the invention's multiple main computer, and media computer. Information is gathered from the sensory responses of the participant that is measured by the invention's means and methods. The invention also provides symbolic quests (SQ) that have abstract connotations that are more poetic than a symbolic quest (SQ) that is possibly narrative. A symbolic quest (SQ) that use abstract ASCs for example can be compiled to be non representational of any everyday mundane experience that uses non-linear representations of form, color, sound and vibrations that produce an effect that is described as visual music. These symbolic quests (SQ) contain abstract ASCs that, can in fact trigger an unexpected response from buried memory.

Furthermore a symbolic quest (SQ) can contain AMV events or multiple event sequences that can be completely composed of nonlinear abstract symbolism that will assist the participant to overcome such problems as post-traumatic stress syndrome. Many war veterans are effected by post-traumatic stress. One therapeutic technique used by therapists is directed rapid eye movement (REM). Stage Six utilizes a unique variation of this technique.

Traditionally this REM technique is designed to release the memory of traumatic events. The movement of eyes during these directed conventional therapeutic sessions cause a disruption of normal processes of visual information to the occipital lobe of the brain. This disruption then causes memories to be released very much the same way certain people experience in lucid dreaming. The present invention can emulate and intensely reinforce through the invention's technological means and methods, a REM session during the processes and procedures of Stage Six.

The symbolic quest (SQ) of Stage Six embodies specialized AMV apparatus and firmware and software means that enable the participant to experience the same benefits of a conventional REM session. A selected AMV event can be constructed that causes similar disruption of visual signal information delivery from the eyes to the occipital lobes of the brain. Additionally, all the guided information supplied by a therapist in a conventional REM session can be delivered to the participant via specially configured symbolic quest (SQ) that embodies multiple AMV events that further embodies; selected REM trigger AMV event information. In fact the present invention's means and methods can amplify REM techniques and methods and create ASSDM AMV-REM procedures. These specialized procedures, significantly improves the effectiveness of the conventional REM therapeutic procedures, and therefore dramatically departs from the original procedure so significantly that the invention in fact creates a new human cognitive reprogramming paradigm.

The participant is also further taught that a non-associative symbolic construct (NSC) is a class of symbolic construct that has no immediate connotative or denotative association to the participant's life experience. A NSC can be construed as a group of compiled symbolic containers (SCr) that embody new SC information. NSCs can be used with ASCs in order to construct a new mythological point-of-view for the participant. For example, the disruptive nature of the aforementioned AMV-REM procedure can be utilized to create a 'symbolic window of opportunity.' In that because of the disruptive nature of the invention's AMV-REM procedure, another symbolic container component (SCC) embodied within a carefully constructed symbolic quest (SQ) can be introduced. This new protocol contains symbolic data that is introduced into the AMV-REM symbolic quest (SQ) protocol during the delivery of important 'cued symbolic containers (SCr) that are components of a symbolic quest (SQ) that embodies AMV events that are dominated by the inventions non-linear abstract ASC event sequences.

These sequences are embodied in a specialized AMV-REM event procedural protocol. In this way, the invention provides the means, method and apparatus for reprogramming human consciousness. During the delivery of these specialized AMV-REM abstract sequences, linear based 're-arrangements' of the memory based stored symbolic constructs (SC) can be introduced into the memory clusters of the participant. This new symbolic data can be used to reconstruct a memory and thus cause the effects of a possible life event trauma (LET) to be diminished or eliminated all together. A specific LET can be eliminated from the memory thus enabling a means to change the present day perceptions of the participant whom may have experienced an LET. However these symbolic quest (SQ) must contain non-associated symbolic constructs (NSC) that are introduced to act as 'connective transitions.' These connective transitions connect stored ASC based life events (LE) that are healthy and needed to maintain a familiar self-identity. These connective transitions are constructed in the invention's AMV apparatus, and are designed to artificially approximate a complete holographic LE that is in embodied in this special class of symbolic quest (SQ).

This new symbolic quest (SQ) that contains a plurality of artificial AMV Life event sequences. This new life event (LE) data will replace the stored memory based life event trauma (LET). The invention provides new symbolic quest (SQ) life experiences that heighten the positive side of one's life, and diminish the traumatic negative effects. Therefore, once this portion of the invention's processes and procedures is completed, the participant will then equate various associative anterior event experiences with the new connotative and denotative meaning of a particular present day event. Therefore, the participant will react to present day anterior LE based stimuli in a more productive way. This portion of the invention's processes, and procedures can benefit the individual participant and human society as a whole. Today, society is moving to fast for an individual to adhere to a universal mythology. The days of unified cultural concepts have past into history. The individual must find, or create his own inner mythology. The invention provides the technological means and methods for the individual participant to codify, create and recreate in his own inner mythological landscape via the process embodied in the inventions ability to fulfill a participant's metaphorical-therapeutic-intent that is also known as a therapeutic agenda.

Figure 4:
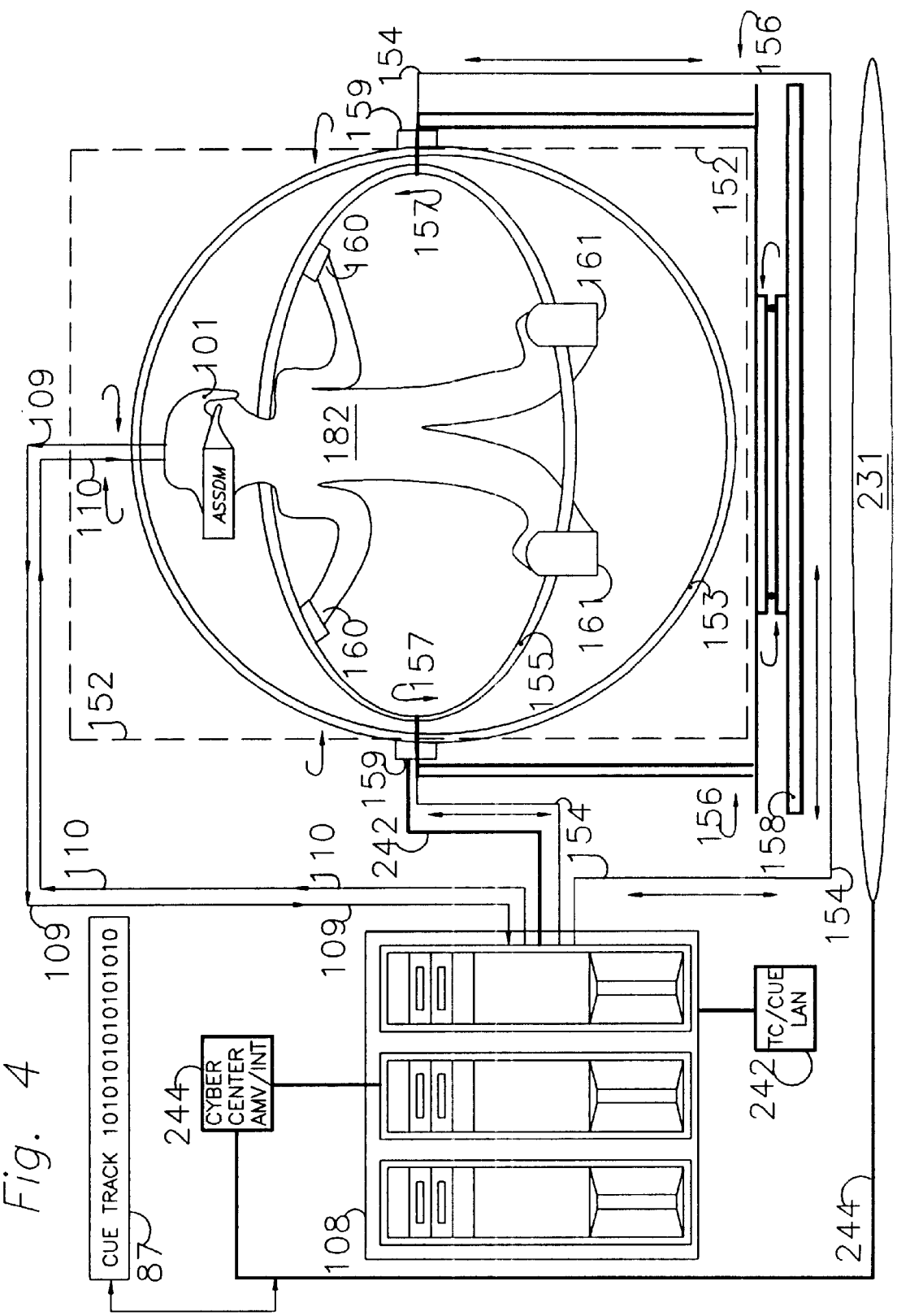
FIG. 4 depicts the tactile 360 degree position wheel, the HMD and the main system control computer, according to the invention.
Figure 5:
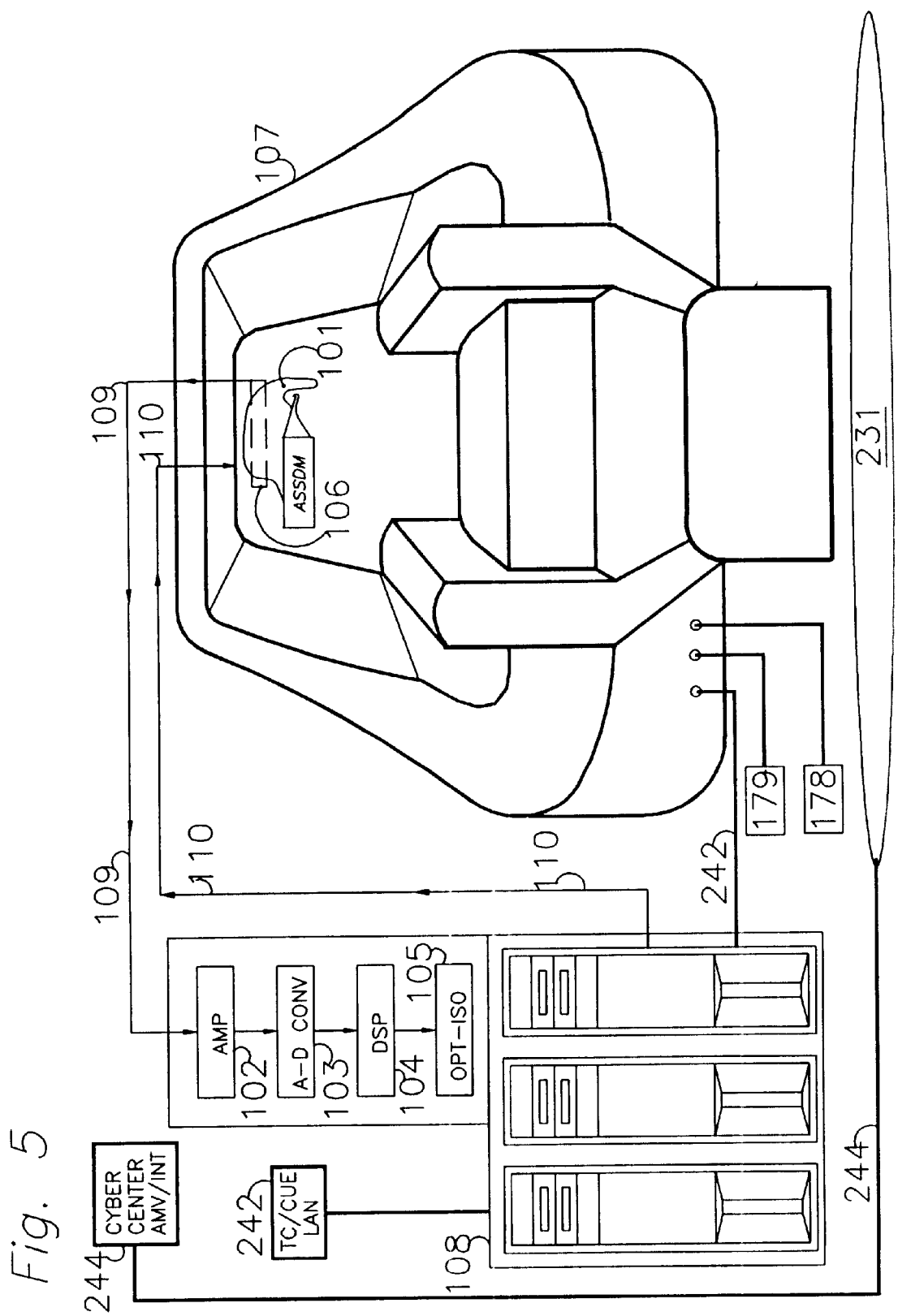
FIG. 5 depicts the holochair, the HMD and the electroocular process, according to the invention.
Figure 9:
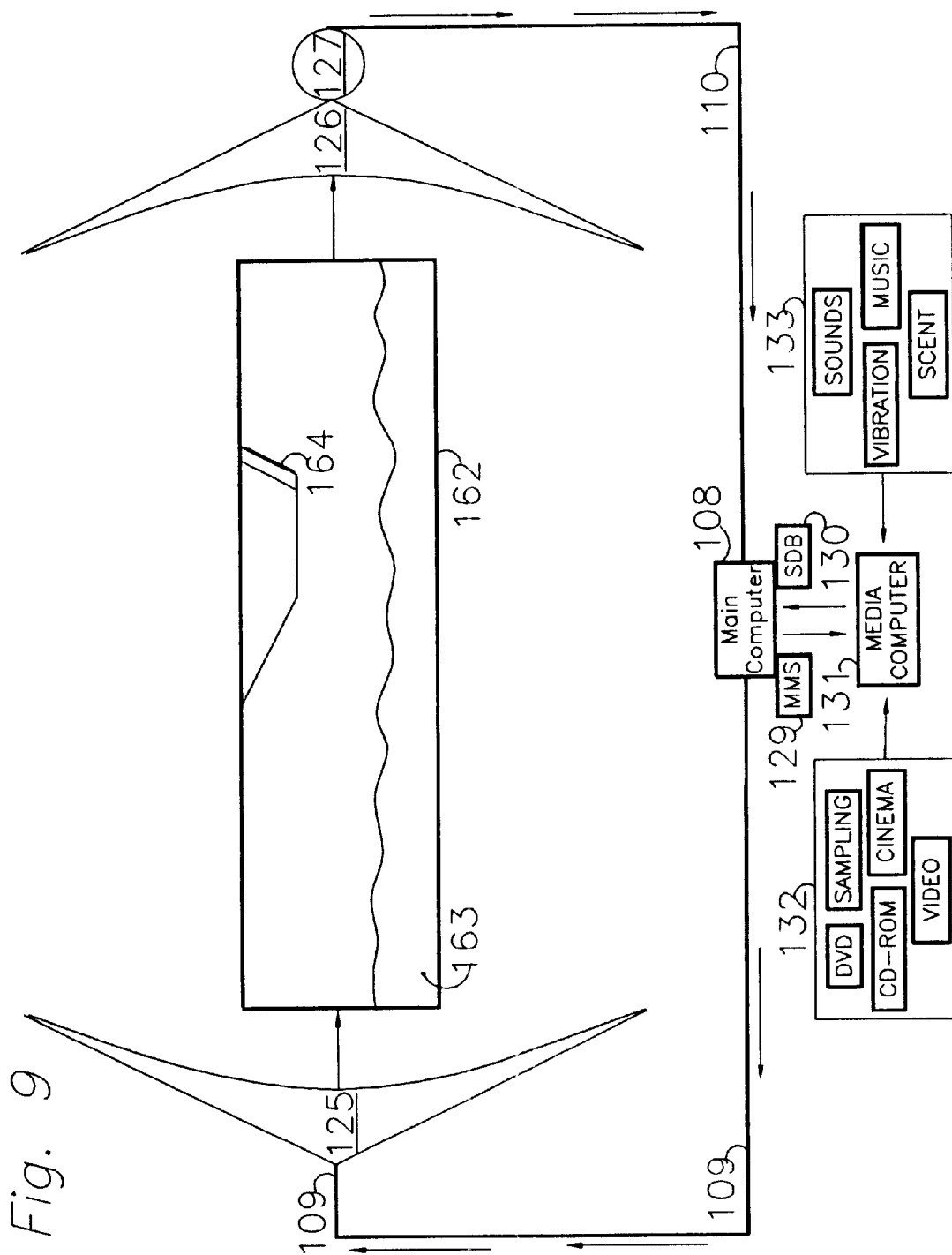
FIG. 9 depicts a floatation tank as an immersion means and how it is adapted to the invention, according to the invention.
Figure 16:
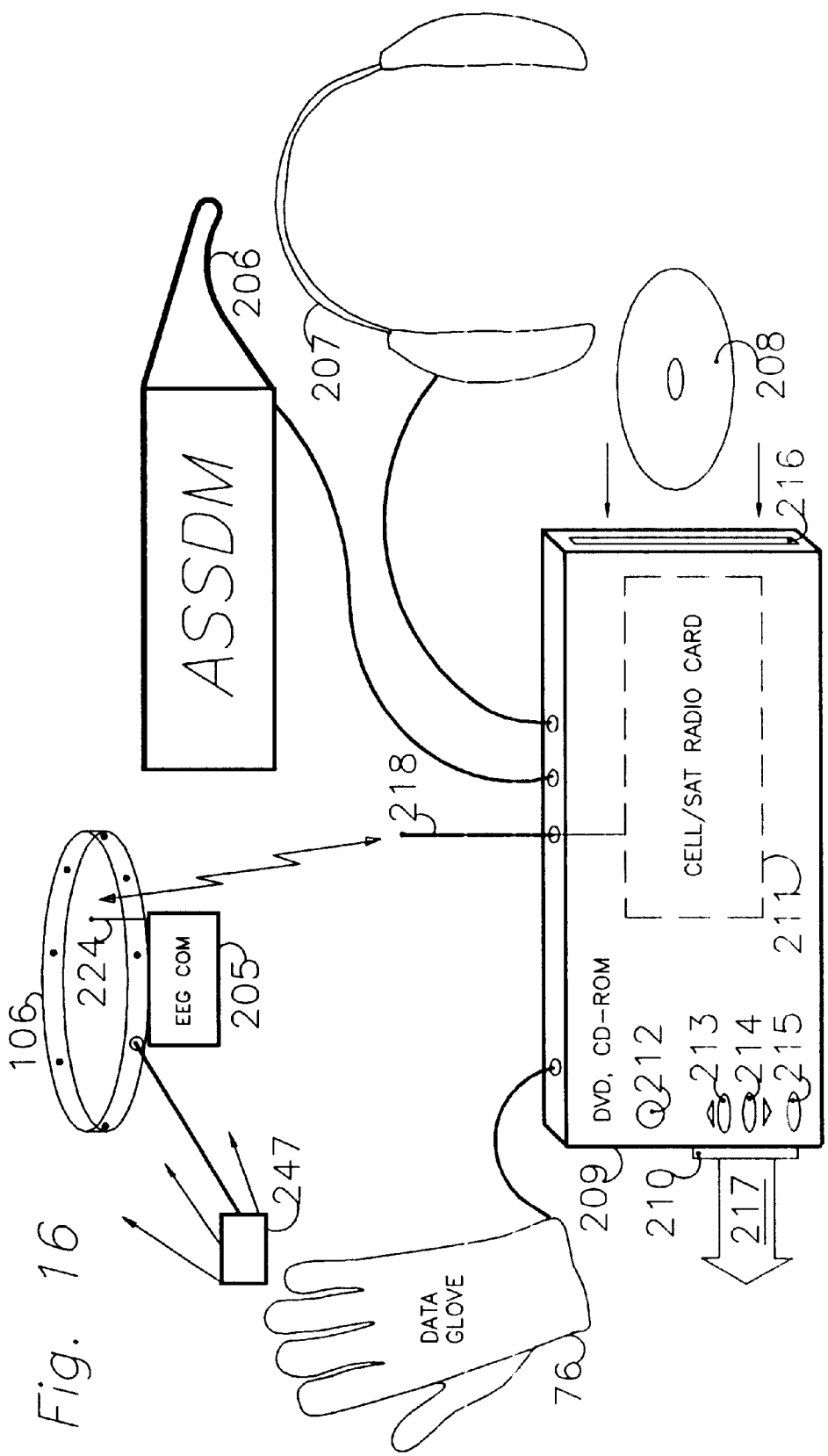
FIG. 16 shows the invention's consumer based consciousness machine, according to the invention.
Figure 18:
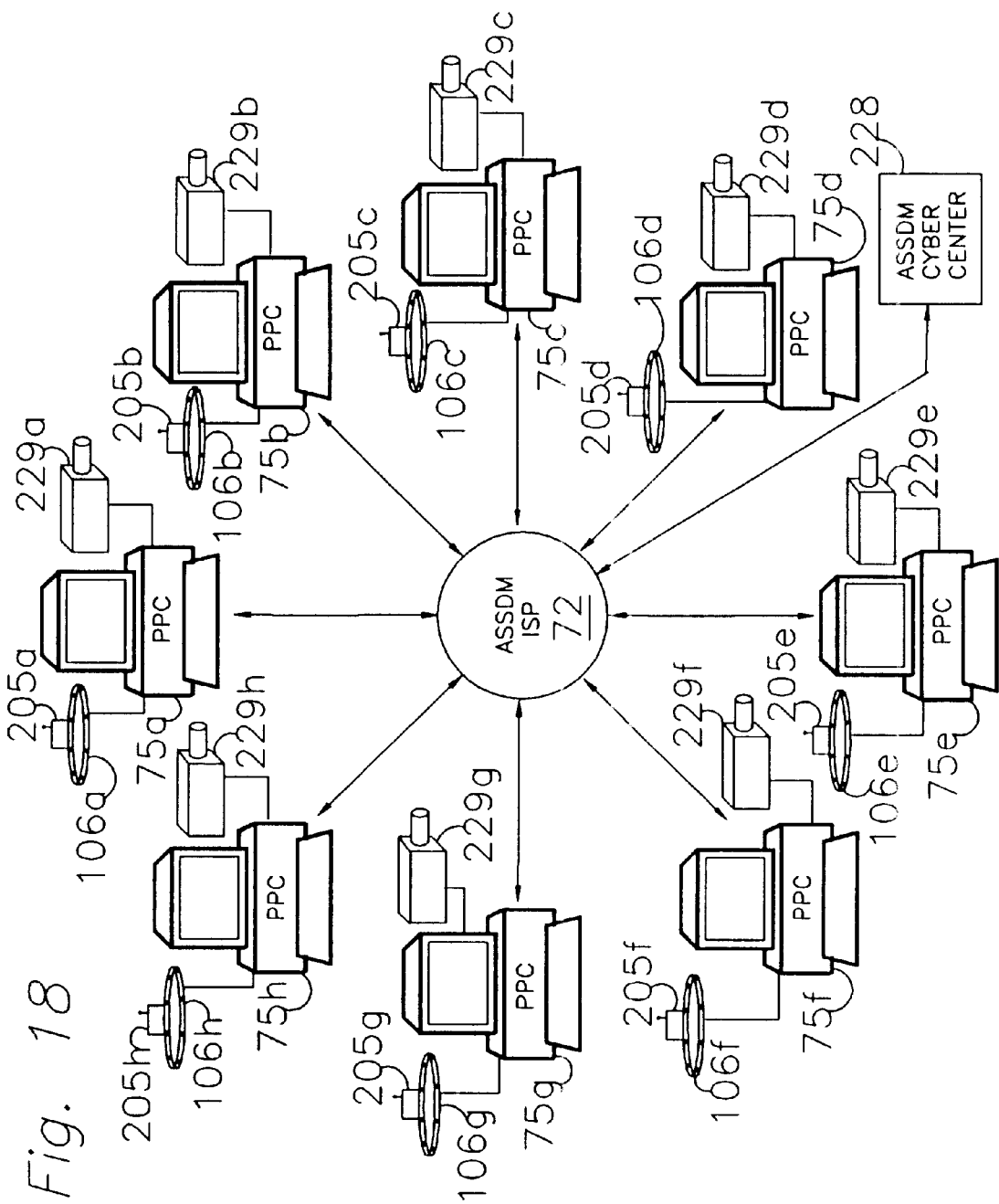
FIG. 18 is a logical diagram of the ASSDM Cybersymbolic network, according to the invention.
Figure 19:
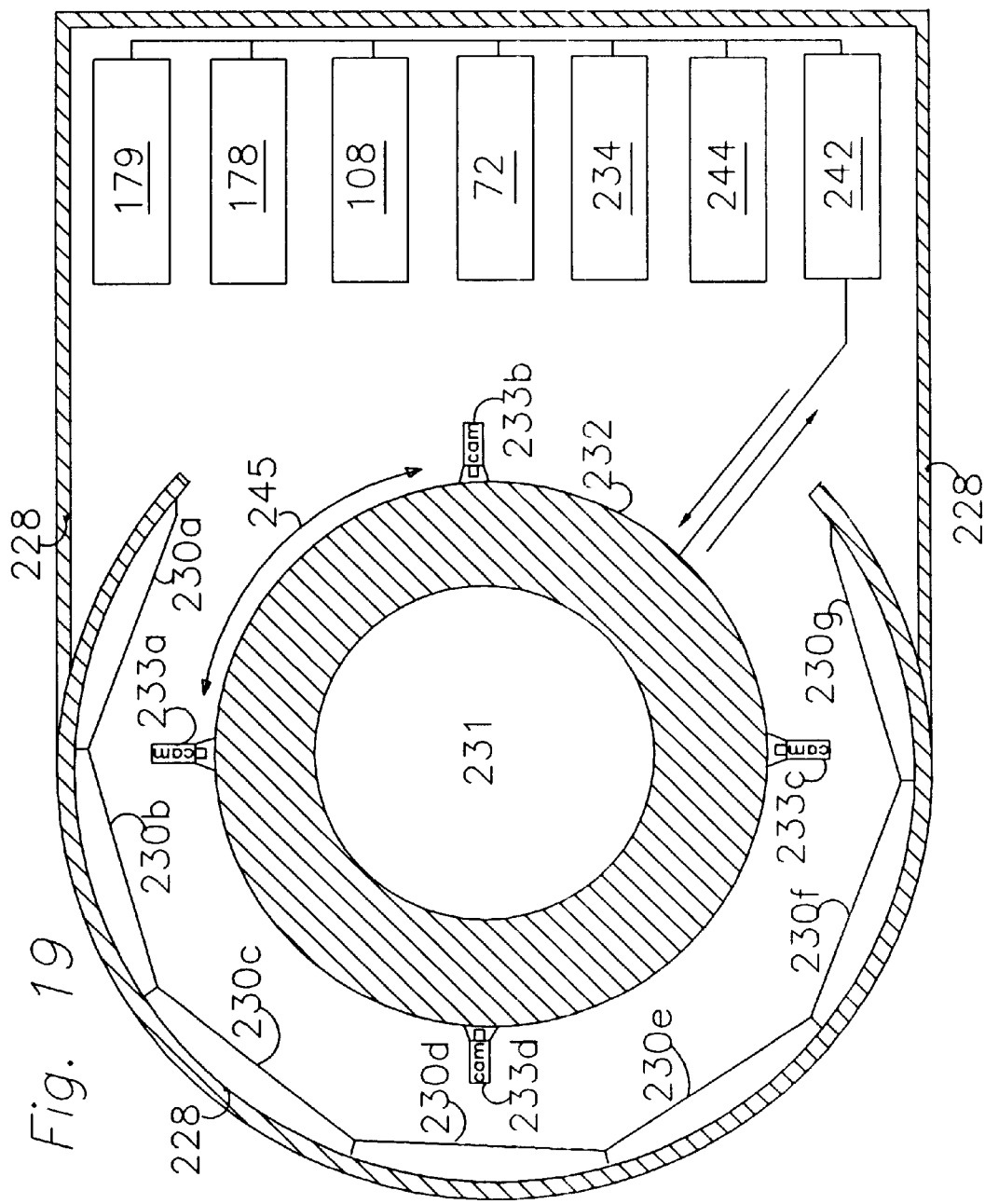
FIG. 19 is a logical diagram of the ASSDM Cybersymbolic internet video conference interactive center, according to the invention.
Figure 20:
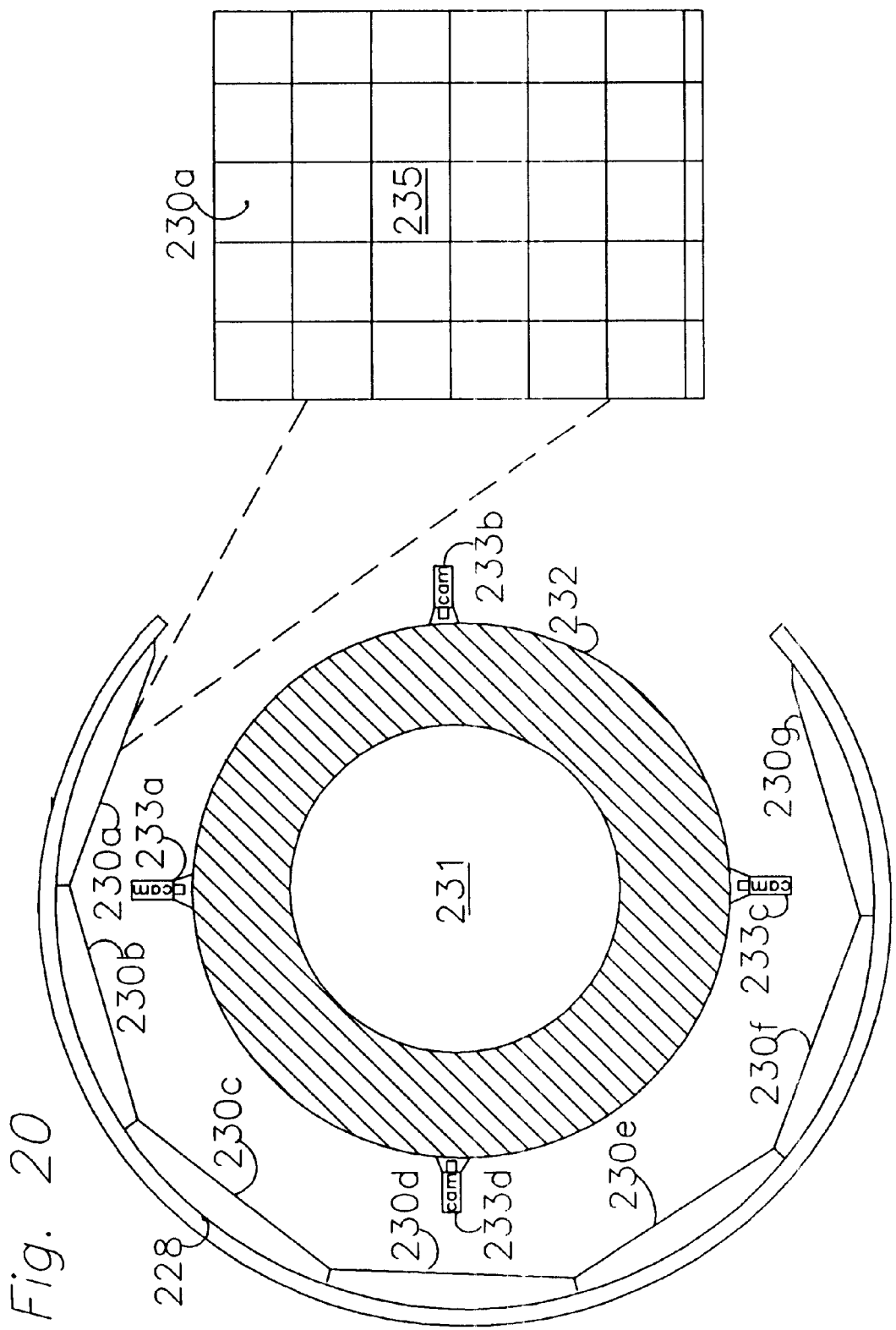

Referring to FIG. 1, the participant is places himself in an AMV apparatus 55, such as the invention's holochair 107, as depicted in FIG. 5, or is placed in the tactile ring 152, as depicted in FIG. 4, or in the flotation tank 162 as depicted in FIG. 9. Additionally depending on the therapeutic purpose, the participant can access the invention's means and methods via the internet world wide web (WWW), and the invention's cyber center as depicted in FIG. 19, and FIG. 20. In addition he can use his own private personal computer (PPC) 75a as depicted in FIG. 18, and or his own 'consciousness machine (CM) 209 as depicted in FIG. 16 for the purpose of utilizes the invention's technological means and methods.

Figure 11:
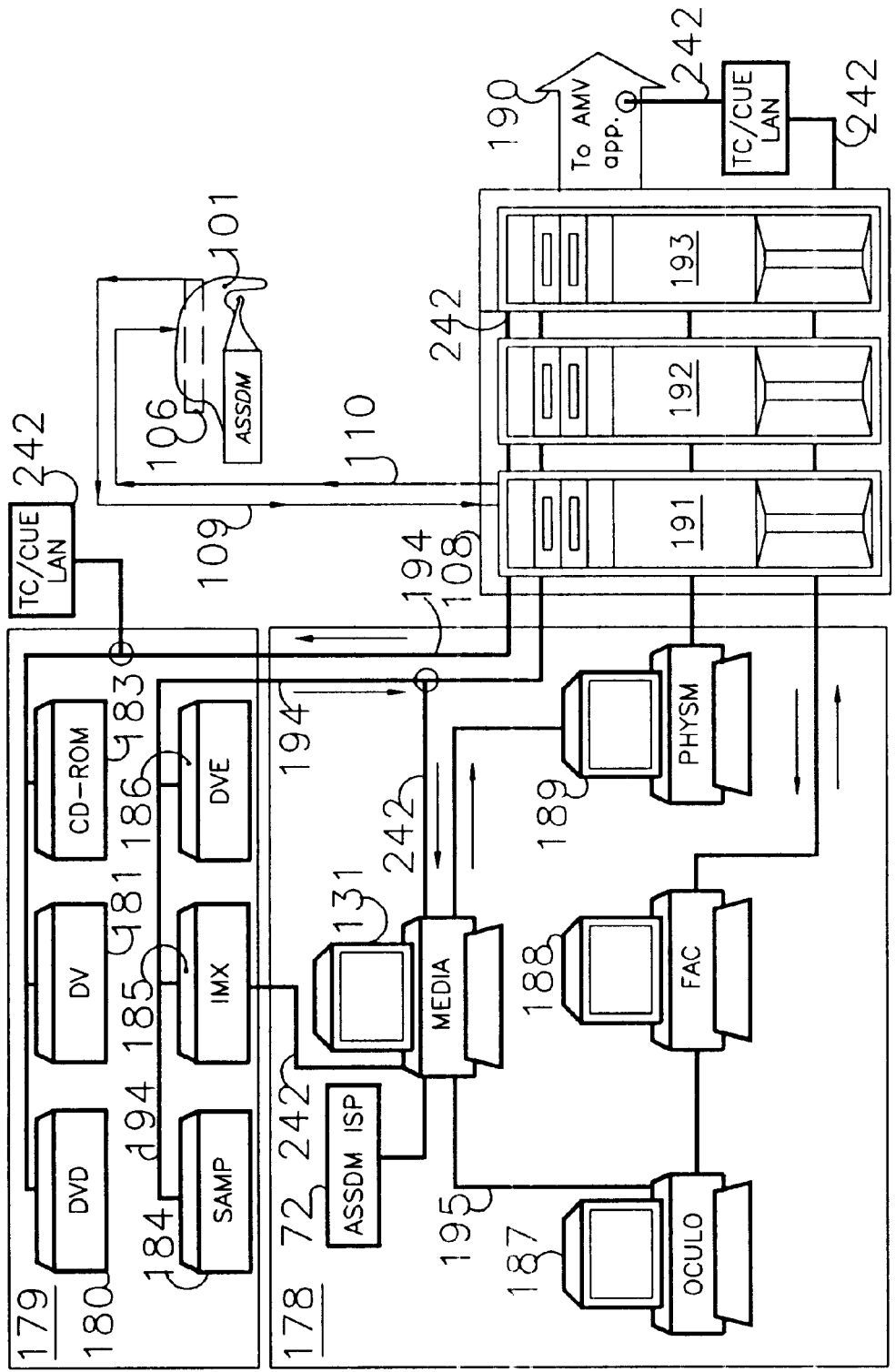
FIG. 11 depicts symbolist-facilitator computer monitoring stations and apparatus, according to the invention.

Referring to FIG. 1, once the participant is places himself in the selected AMV-VR apparatus, the biological signal sensors (BSS) are attached to the participant 56, by a facilitator. The biological signal sensors can be configured for usage with, and embodied within a headstrap 106 as depicted in FIG. 5. The BSS can be an integral part of the HMD apparatus 101, or attached and applied to any other area of the human body. The HMD is placed on the participant 57 and other AMV apparatuses are activated in accord with the technological requirements embodied within the selected ASSDM Stage artificial intelligence based program. A selected ASSDM Stage program that embody selected symbolic quests; that embody multiple AMV events; that embody multiple symbolic pathways SP); that embody multiple symbolic containers (SCr), that embody the metaphorical-psychological polarity of the selected symbolic constructs (SC), is therefore initialized 58. The main computer 108 as depicted in FIG. 11. Referring to FIG. 1, the aforementioned main computer begins managing the selected ASSDM Stage program 59 by preparing the delivery of selected symbolic quests (SQ), that embody selected AMV events, to the participant's senses, via the inventions selected AMV apparatus, and specially constructed symbolic quest (SQ), that embodies selected symbolic containers (SCr), that contain multiple symbolic constructs (SC).

The main computer receives the data produced by the biological signal sensor (BSS) and evaluates the data 60. The main computer than instructs the media computer to arrange the selected symbolic constructs, contained within a selected symbolic quest (SQ) via selected symbolic container (SCr) 61. The media computer causes selected multimedia transports to initialize and cue as a technical preparation for the delivery of selected symbolic constructs (SC) via selected symbolic containers (SCr) 62 to the participant sensory perceptions via artificial reality and ASSDM multimedia VR apparatus (AMV).

Figure 2:
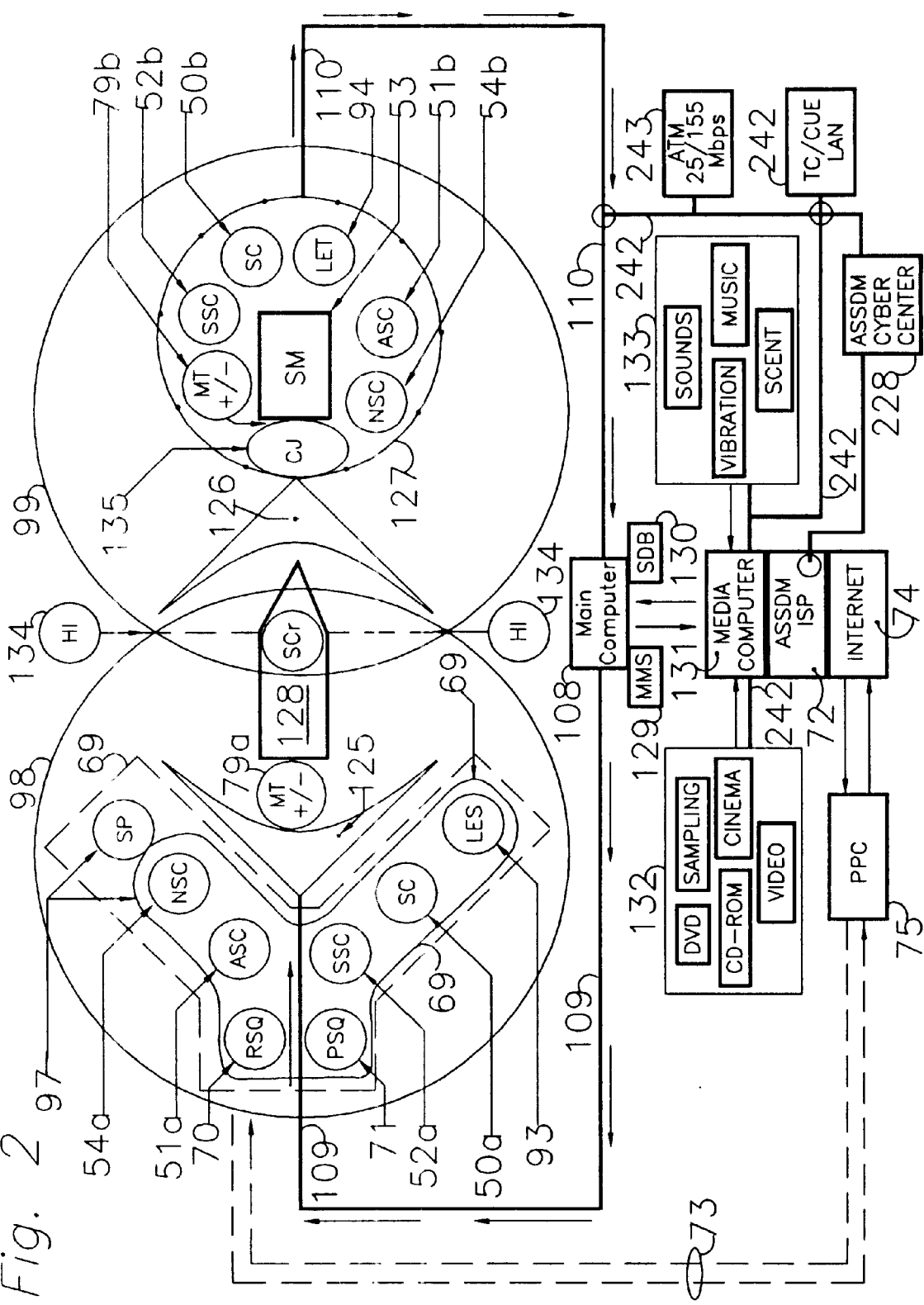
FIG. 2 depicts the interaction of the participant with the means, method and apparatus of the on-site ASSDM system and internet system, according to the invention.

Selected AMV apparatus deliver selected symbolic quests (SQ), which embody symbolic constructs (SC) via selected symbolic containers (SCr) to the selected MV apparatus and participant's senses 63. The main computer 108 as depicted in FIG. 2, in conjunction with the statistical database (SDB) 130, and physiological measurement apparatus such as an EEG system, respond to received biological signal sensors (BSS) 64 as shown in FIG. 1. Results are read by main computer in conjunction with statistical database or engine 65. The Main computer, in conjunction with the media computer continue to provide symbolic quest (SQ) sequences that embody additional selected AMV events, that in fact embody symbolic containers (SCr) that embody selected symbolic constructs (SC) and deliver the selected symbolic quest (SQ) via technologically designed AMV immersive event. The AMV technological event and its related AMV apparatus provide the artificial reality to the participant's senses via AMV apparatus 66. Results of the symbolic quest (SQ) that is embodied ASSDM Stage AMV events, will have desired impact upon the participant's perceptions, based upon his therapeutic agenda that is embodied with his metaphorical-therapeutic-intent.

The impact of the invention's symbolic quest (SQ) experience is evaluated as a result of physiological readouts, and the observations of the facilitator. These aggregate evaluations cause the next ASSDM Stage to be initiated 67. The invention's main computer then compiles the dominant AMV sequences that had the desired impact upon the participant's perceptions. These selected AMV sequences embody the completed ASSDM Stage. The main computer therefore instructs the media computer to select the preferred media transport system 179 as depicted in FIG. 11 and downloads them to the appropriate media transport medium. The selected transport medium can be a DVD recorder 180, or a digital video deck 181, or a recordable CD-ROM deck 183, or other type of digital retrieval system such as an IMX system 185.

In FIG. 1, the symbolic 'prescription' is therefore provided to the participant for home or office use 68. Also, the symbolic prescription can be delivered and retrieved via the internet or selected wireless network to the participant's personal computer (PPC) 249. The PPC embodies the invention's special PPC software, and its specialized AMV apparatus. The selected symbolic prescription can also be delivered to the participant's wearable consciousness machine (CM) 209 as depicted in FIG. 16 via the internet world wide web (WWW), and or associated cellular telephone systems, personal communications systems (PCS) or satellite networks 250.

Referring to FIG. 2, the ASSDM methods encompass many levels of manipulating and orchestrating artificially derived symbolic quests (SQ) 69 that embody a plurality of symbolic pathways (SP) 97. These symbolic pathways (SP) 97 are in fact composed of selected symbolic containers (SCr) 128, that are comprised of selected symbolic constructs (SC) 50a, that can be deemed associated symbolic constructs (ASC) 51a, and/or non-associated symbolic constructs (NSC) 54a, and/or singular symbolic constructs (SSC) 52a. These symbolic constructs (SC) 50a are delivered to the participant's 99 natural perceptual sensorium 126, via an artificially constructed reality 98 that is embodied in uniquely designed and arranged symbolic containers (SCr) 128. These symbolic containers (SCr) 128 comprise specially selected and arranged symbolic constructs (SC) 50a that enable the psychological processes and procedures of participant's The metaphorical intent is further embodied within the invention means and method for creating the desired and scripted 'metaphorical polarity' (MT) 79 represented by this simple mathematical symbol '−/+.' This metaphorical polarity (MT) 79 is represented by key symbolic constructs (SC)

50a that embody multiple meaning that create a healthy conflict resolution environment. This metaphorical conflict enables the desired psychological stress that further creates the opportunity for reprogramming the participant's internal mythological structure, via the re-arrangement the symbolic constructs (SC) 50b that are embodied in the inventions symbolic containers (SCr) 128, that are multiply linked to create individual symbolic pathways (SP) 97, that are the embodiment of the inventions symbolic quests (SQ). This metaphorical conflict causes psycho-symbolic 'triggers' to release symbolic constructs (SC) to be released into the conscious perceptions of the participant. This release function creates an opportunity for reprogramming the embedded the participant's stored memory 53 with new more healthy information.

In FIG. 2, selected AMV apparatus outputs for human perception 125, are defined as; HMDs, computer screens, video screens, television monitors, body suites, holochairs, tactile position rings, flotation tanks, data gloves, audio speakers, headphones, tactile transducers, olfactory stimulators, brain implants, subdermal implant-receivers, neural implant-receivers, topical sensor-receivers and other multimedia apparatus. Symbolic Quests (SQ) that embody one or more AMV events that embody multiple symbolic containers (SCr) 128 that in turn embody multiple, symbolic constructs (SC), fed from the main computer 108 via ASSDM facility network means 109. The main computer 108 controls the media computer 131 that access various multiple media storage (MMS) 129 and transport systems such as DVDs, digital and analog audio sampling, CD-ROMs, cinematic transports, and other video transports 132.

The media computer preferably uses these transport mechanisms to deliver sounds, tactile vibrations, music and olfactory scent 133 to the participant's natural biological reality 99 via an orchestrated symbolic quest (SQ) 69 symbolic container 128 that is one of the preprogrammed and specially designed AMV event experience 134. This AMV event experience is an artificially derived sensory phenomenon that will have the desired effect upon the participant's sensory perceptions 126 and the various (SC) 50b contained in his stored memory 53.

The symbolic container (SCr) 128 effects the participant's (PAR) 99 critical judgement 135 by merging 134 artificial reality 98 with symbolic constructs (SC) 50b that are received and compared with stored human memory 53. These symbolic constructs (SC) can be received singular symbolic constructs (SSC) 52b, received non-associated symbolic constructs (NSC) 54b, and received associated symbolic constructs (ASC) 51b. The participant's conscious and subconscious reactions to the received symbolic containers (SCr) 128 are measured via biological signal sensors (BSS) 127. The electrical signals are amplified, incremented and sent to the main computer 108 via the ASSDM facility system network return means 110 and fed into a statistical database (SDB) 130.

Each SDB data increment contains the responses that the participant produced from experiencing a designated symbolic quest (SQ) 69, that is embodied in a selected ASSDM Stage, that contains a selected category group of a desired AMV event technological experience 134, further that embodies multiple symbolic containers (SCr) 128, that are composed of multiple symbolic constructs (SC) 50a.

The SDB 130 directly intercommunicates with the main computer 108 for the purpose of providing the physiological measurement data that directly tracks and records participant response to one of the multiple of AMV 134 events that occurs during a designated ASSDM Stage session.

The main computer 108 retrieves the SDB information, stores it and evaluates the participant responses tracked by the statistical database (SDB) 130. Once the AMV-SDB data is received by the main computer 108, it then instructs the media computer 131 to initiate and send carefully selected AMV event sequences that significantly relate to the selected symbolic quest's (SQ) 69. The selected symbolic quest (SQ) 69 embodies the preplanned thematic motif, cinematic style, symbolic-content and multi-form-montage features of the subsequently experienced AMV event. The participant's attention and physiological responses therefore cause the ASSDM system to deliver specific AMV events to the participant's senses. Within the content of the selected AMV event are selected symbolic containers (SCr) 128 that will in fact reinforce or defuse the impact of the prior AMV event experience. These AMV event experiences are governed by the observed and measured needs and recorded reactions of the participant. In this way, the participant becomes his own therapist.

Figure 10:
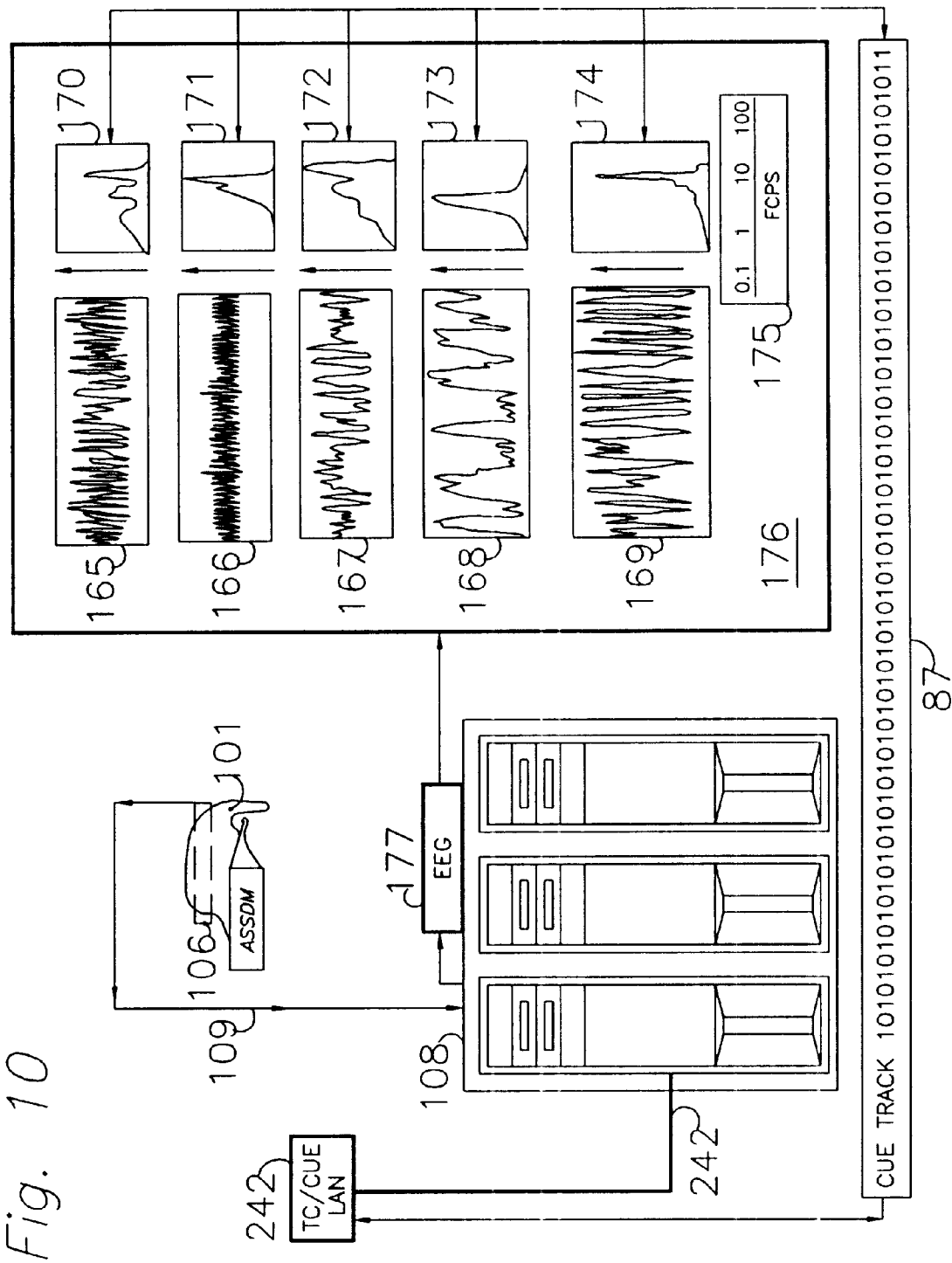
FIG. 10 depicts electroencephalogram readouts of the five main brain waves, according to the invention.

In FIG. 10, the invention's physiological measurement means is a critical component of its processes, and procedures. A primary object of the invention is to utilize measurements of human brain wave activity. Since EEG was first devised in the 1920s researchers have discovered that the brain has a tendency to produce brain waves of five distinct varieties, which are called alpha 165, beta 166, theta 167, delta 168 and mu 169 waves. For example, alpha waves 165 tend to occur when we close our eyes and become more relaxed, passive or unfocused, brain-wave activity slows down, and the brain produces bursts of alpha waves, which range in frequency from about 8 to 13 Hz 170. When a person becomes relaxed and unfocused, alpha waves become dominant throughout the brain, producing a calm and pleasant sensation called the alpha state. The alpha state seems to be the brain's "neutral" or idling state, and people who are healthy and not under stress tend to produce a lot of alpha activity. Lack of significant alpha activity can be a sign of anxiety, stress, brain damage, or illness.

Referring to FIG. 10, beta waves 166, the most rapid brain waves, range in frequency from 14 Hz to more than 100 Hz 171. When a person is in a normal waking state, eyes open, focusing on the anterior reality that we perceive to be external, or dealing with concrete, beta dominate the brain processes. We a person focuses upon specific problems that activate the analytical-intellectual aspect of our consciousness, again beta waves dominate. Beta waves are associated with alertness, arousal, concentration, cognition, and in some cases, anxiety.

Theta waves 167 occur when a person's consciousness deepens into drowsiness. The brain shifts to slower, more powerfully rhythmic theta waves, with a frequency cycles per second (FCPS) 175 of about 40 to 8 Hz 172. Theta has been called the twilight-state, between waking and sleep. During this state the brain is receptive to the input of new data, in the form of new symbolic constructs (SC), delivered by the invention's key symbolic containers (SCr), that is embodied in the invention's symbolic quest (SQ). The theta-state is often accompanied by unexpected, dreamlike mental images. Often these images are accompanied by vivid memories, particularly childhood memories. The invention also utilizes this state to access memory based symbolic constructs (SC) by in fact inserting symbolic containers (SCr) into the conscious, or near conscious perceptions of the participant. The symbolic containers (SCr) are provided to the participant's senses via selected AMV events that are components of selected symbolic quests (SQ). The invention utilizes the theta-state to insert randomly applied symbolic quests (RSQ) and planned symbolic quests (PSQ). The theta-state offers the participant access to unconscious material, reveries, free association, sudden insight, and creative ideas. The invention uses this state to insert symbolic constructs (SC) embodied in symbolic containers (SCr) to cause specific memories to be released and examined.

Delta waves 168 tend to dominate human consciousness when a person falls asleep. The frequency bandwidth of delta waves tends to range below 4 Hz 173. When most people fall asleep. However, there is growing evidence that individuals may maintain consciousness while in a dominate delta-state. The invention utilizes this brain wave state to insert non-visual symbolic constructs (SC). Interestingly, it is during the delta-state that the brains produce large quantities of healing growth hormone that directly relates to new memory storage capabilities. The invention fully exploits this researched and verified fact.

The invention utilizes the delta-state to cause behavioral programming to occur, especially during the invention's rapid eye movement (REM) sleep state therapeutic methods. The invention provides auditorial, and tactile-vibrational based symbolic constructs (SC) and symbolic containers (SCr) that in fact cause new consciousness states to occur such as, deep learning opportunities. By applying various acoustic resonates and vibrational and positional techniques new programming can occur, and stored memories can be released and examined by the participant and facilitator during the discovery or uncovering stage embodied in the invention's Stage Four. During this stage, the participant's therapeutic agenda is established. Mu waves 169 for example are another level of brain wave, which resemble croquet wickets in shape 174, are associated with physical movements, are a directed intention to move about physically.

Most people have certain recurrent behavioral themes or motifs. Some of these behavioral habits may in fact be harmful, self-defeating, and self-destructive. These negative behavior states are often the result of experiences that have been imprinted within our consciousness during moments when we were highly receptive to; the programming nature of a given life event (LE) or suggestible-particularly during childhood. The mind operates in a progression of symbolic constructs (SQ) that are amalgamated into internally guided behaviors that are in fact our internal psycho-symbolic mythology.

Figure 3:
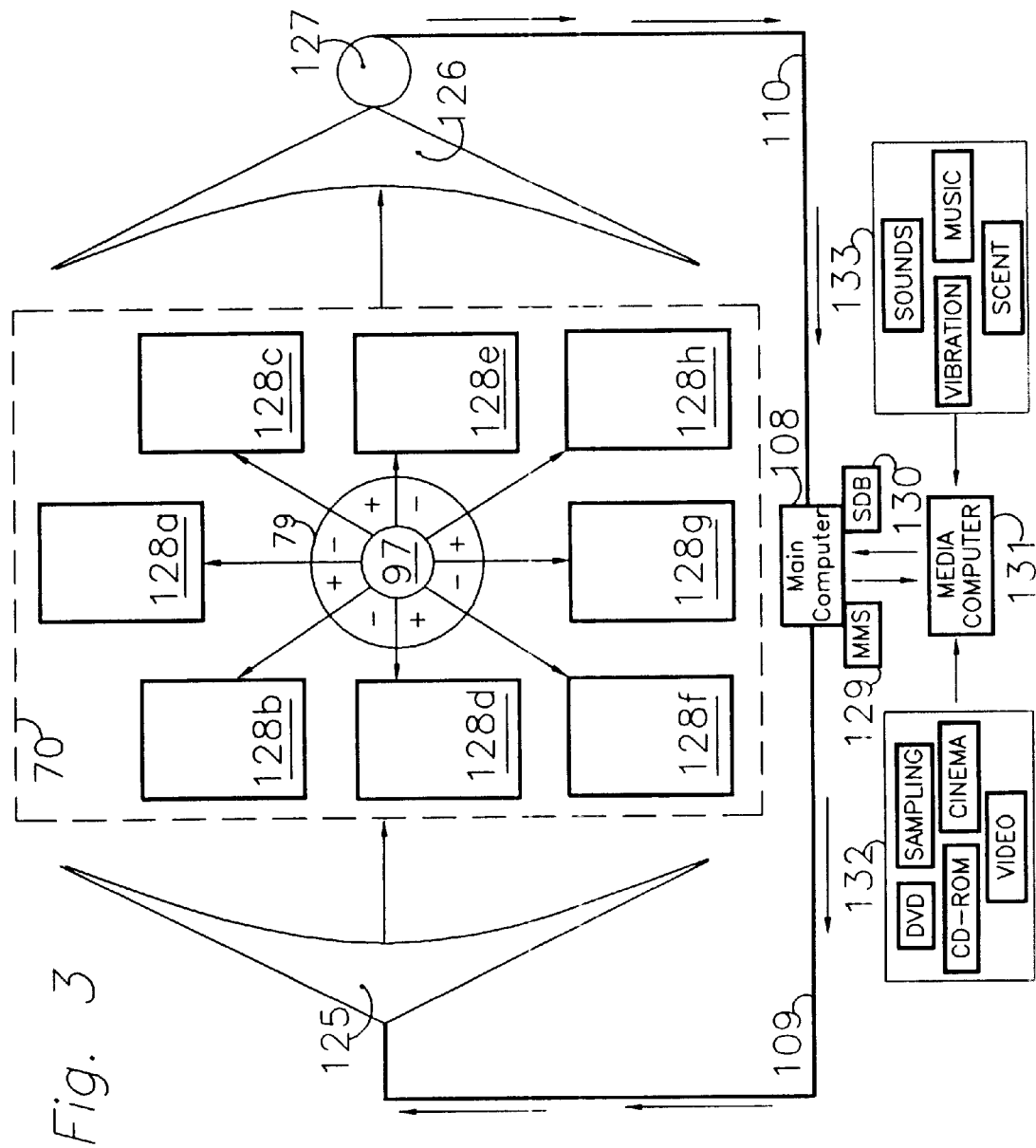
FIG. 3 illustrates the ASSDM system with its random multiple scenario means, embodied in symbolic quests, according to the invention.

With reference now to FIG. 3, depicted here is a diagrammatic-template of a randomly applied symbolic quest (RSQ) 70. This RSQ 70 is comprised of eight symbolic pathways (SCr) 97. Each symbolic pathway (SP) 97 contains and embodies its own unique symbolic containers (SCr), 128a, 128b, 128c, 128d, 128e, 128f, 128g, and 128h, which contains special arrangements of symbolic constructs (SC), when specially arranged by the inventions means and methods; create associated symbolic constructs (ASC), and non-associated symbolic constructs (ASC). The differing metaphorical energies of the selected symbolic constructs (SC) 50a further create selected symbolic containers (SCr) in a directed 'act' of metaphorical-polarity 79 that is in fact embodied in the participant's and the facilitator's metaphorical-therapeutic-intent.

Each symbolic pathway (SP) 97 is specially designed to tell its own mythological story or scenario. Each of the eight or more symbolic pathways (SP) 97 tells a particular metaphorical story of the self via its embodied multiple symbolic containers (SCr) 128a, and this includes the positive and negative connotative polarity contained in the symbolic metaphor. Each symbolic pathway (SP) 97 also acts as an embodiment of metaphorical-polarity 79 when the participant intellectually, emotionally and experientially compares one symbolic pathway (SP) 97 with another via; the embodied symbolic containers (SCr) 128a, 128b, 128c, 128d, 128e, 128f, 128g, and 128h, and the selected and embodied symbolic constructs (SC) that in fact create the symbolic containers (SCr).

Figure 8:
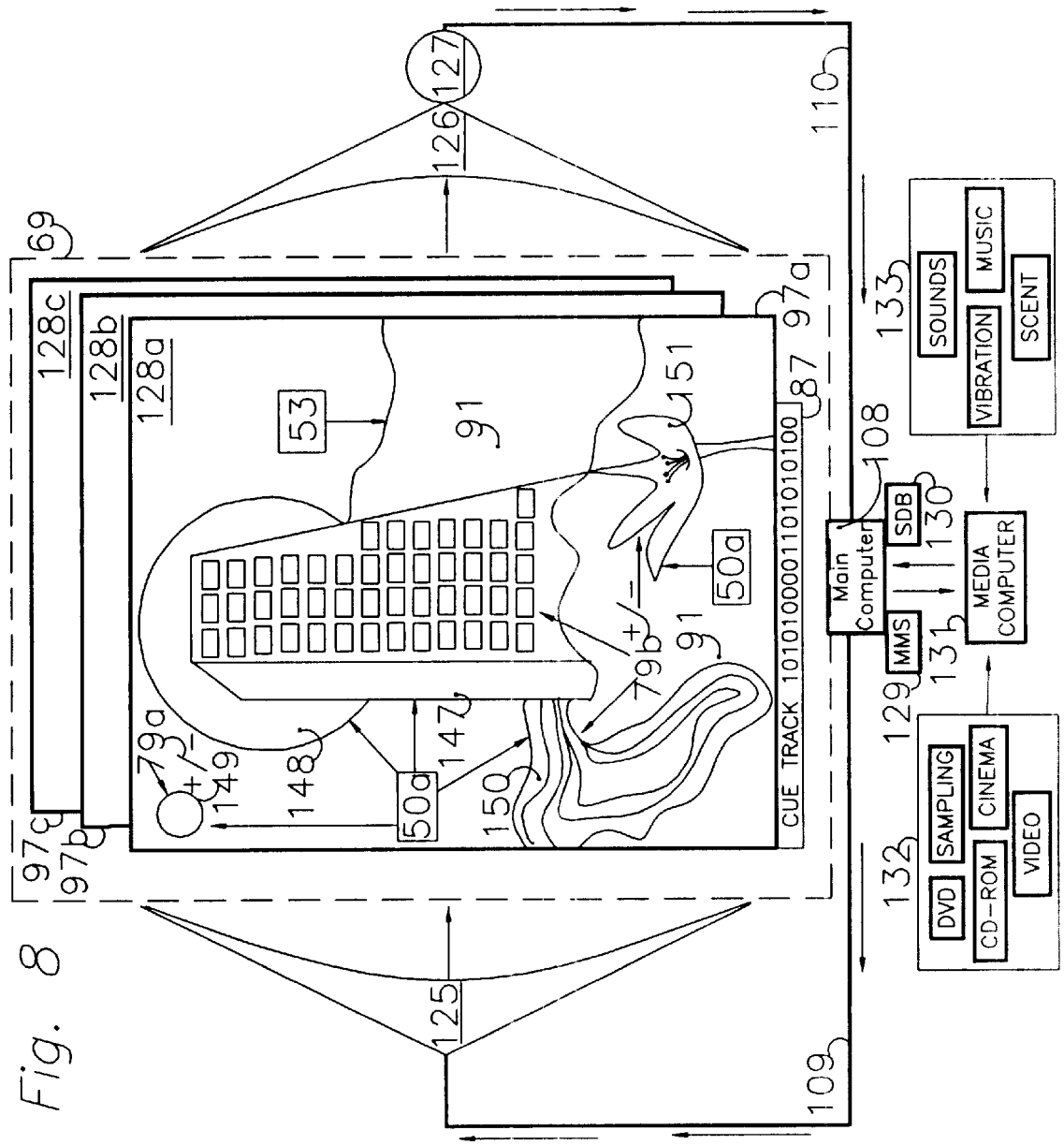
FIG. 8 depicts an archetypal symbolic journey as symbolic container, according to the invention.

Referring to FIG. 8, depicted here is a symbolic pathway (SP) 97a. This symbolic pathway (SP) 97a is comprised of symbolic constructs (SC) 50a that connote and relate to archetypal psychological symbolism that in fact relate to; universal symbolic concepts embodied in selected multiple symbolic containers (SCr) 128a. During the seminar environment of Stage Three, the participant learns to recognize and understand the different archetypal and psychosymbolic meanings and qualities of each symbolic construct (SC) 50a. One important aspect the participant learns, is how certain symbols compare and contrast with one another in the symbolic metaphorical context of the participant's metaphorical-therapeutic-intent, also known as the therapeutic agenda or goal. Additionally, the intrinsic emotional, intellectual, and life event based experiential connection of the metaphor embodied in each symbolic construct (SC) 50a creates the metaphorical-polarity that stimulates the participant with emotional, intellectual and experiential metaphorical-tension.

For example, the Sun 148, and the Moon 149 are associative symbolic constructs (ASC). Both of these symbolic constructs (SC) are familiar universal symbols that speak to each person in different ways based upon the metaphorical-therapeutic-intent that is predetermined by the facilitator and the participant.

In FIG. 8, the positive or negative metaphorical polarity 79, embodied in the experiential nature of the symbolic container (SCr) 128a, is the active therapeutic principle that causes the change within the participant's perceptions of past life event trauma (LET), and how he deals with current and future life events (LE). This change in perception causes the desired psychological stress. This stress occurs within the consciousness of the participant, and in fact results in noticeable changes in the participant's physiological metabolic stress level measurements. This 'stress' is expressed here as symbolic-metaphorical-polarity (MT) 79, and, is the casual factor that alters the significance of the life event trauma (LET), and therefore alters the significance of the stored memory material that is associated with the LET.

When the desired psychological stress is achieved within the participant's consciousness; measurable physiological stress results, then the inventions software, firmware and hardware means and methods 'read' participant's metabolic stress level reactions. Therefore, based upon the analytical significance of the participant's received 'stress measurement data,' the inventions main computer determines what additional symbolic containers (SCr) 128a need to be delivered to the participant's sensorium during the instant immersion experience of AMV technological event that is embodied in a selected psycho-symbolic stage of the inventions means and methods.

This metaphorical or symbolic intent, that is in fact based on the participant's therapeutic-intent cause participant's perceptual 'change' or 'movement.' This experiential-symbolic-intent therefore is embodied in the multiple symbolic containers (SCr) 128*a* that are comprised of specially arranged symbolic constructs (SC) 50*a*. It is in fact the metaphorical-symbolic-content of the provided symbolic constructs (SC) 50*a* that create the numinous metaphorical polarity (MT) 79, that, in fact is the desired psychological 'action' embodied in the multiple facets of inventions symbolic container (SCr) 128*a*.

This action or psychological 'movement' results from the transformative effect for the participant, when he embodies his metaphorical-therapeutic-intent within a selected symbolic quest (SQ) 69. The selected symbolic quest (SQ) 69 is comprised of technologically linked multiple symbolic pathways (SP) 97, that embody a plurality of symbolic containers (SCr) that are constructed of a plurality of symbolic constructs (SC). Therefore, the psychological movement of the participant's perceptions, and its resultant transformative effects, are caused by the inventions means and methods and embodied apparatus.

In FIG. 10, the EEG readout 176 of the participant's brain waves will immediately indicate what the instant effect ASSDM symbolic quest (SQ) has made upon the participant's perceptions, and physiological reactions.

With reference to FIG. 8, while some people in highly technical societies view these symbols in one way another person from an indigenous society will view these symbolic constructs (SC) 50*a* in yet completely different way. The participant is taught to see these symbols in a personal mythological connotation by first learning the universal quality endemic to specific cultures. Next, the participant learns to recognize the metaphorical concepts of these symbolic constructs (SC) 50*a* in relation to his own personal mythological landscape, and for the purposes of embodying his own therapeutic-metaphorical-intent. For example, the universal symbolic qualities of the Moon 149 relate to the twelve to thirteen 'lunar months' of the year. The Moon also relates to the ebbs and tides of human emotions. In a more esoteric sense, the Moon 149 relates to the mysterious, and the unknown.

The Moon symbol 149 also means gentle evolutionary completions and beginnings. It is therefore associated with growth and maturation through knowing the hidden inner self. The Moon 149 also relates metaphorically to the feminine self, the world of dreams, and the world of endless dualities. The three phases of the Moon relate to beginnings, completions and endings in human relationships. The Moon has many connotative symbolic metaphors that have many layers and meanings attached to it. This important symbolic construct (SC) 50*a* becomes powerful, when the participant learns to attach personal connotative meanings to his own personal metaphorical life, and therefore 'contains' the symbolic-metaphor that in fact is the experiential symbolic container (SCr) 128*a*.

The connotative animal nature of the Moon 149 is for example, how it symbolically relates to the primal drive of the wild wolf, or the sensitivity of a dolphin or the night owl. The Moon 149 also metaphorically relates to the 'cool' of the night. The Moon symbol 149 can be construed as an associated symbolic constructs (ASC) that is first of all relatable on the most mundane of universal symbolic levels, such as the fact that everyone in all cultures 'see' the Moon 149 in the night sky. In still other ways the Moon embodied as an esoteric symbolic construct (SC) 50*a* that is at first glance non-associative, in that, its esoteric connotations are not well none to most people and therefore has no transformative relevance. The participant is taught to view the Moon 149 as part of the mythological self, and therefore it becomes an associative symbolic construct (ASC) that is familiar on the deepest esoteric psycho-symbolic levels.

Symbolic constructs (SC) 50*a* have no inherent 'power,' their power comes from relating to symbols in the guise of a personal metaphor that can be an active experiential aspect of the self, that in fact takes on a 'life' of its own. The symbolic life force therefore is an inherent part of the metaphorical-therapeutic-intent. This intent is embodied within the symbolic structure of the inventions symbolic quest (SQ) 69. The Moon 149 therefore is but one component of this symbolic container (SCr) 128*a* that is constructed by the inventions artificial intelligence means and method to tell a unique scenario via the symbolic pathway (SP) 97*a* or story of the self that contains the symbolic metaphorical qualities of the mythological self.

Another important symbolic construct (SC) 50*a* is the Sun 148, that is the metaphorical opposite of the Moon 149. In a broad connotative sense, the symbolic-metaphor that is embodied as 'polar-opposites' in fact create the metaphorical-polarity 79. In a basic sense, the intellectual active qualities of the Sun 148 are the polar opposites of the passive, emotional, and intuitive symbolic metaphor that is embodied in the Moon 149 symbolic construct 50*a*. The psycho-symbolic nature of the Sun 148 and the Moon 149 in fact can create the desired metaphorical-tension (MT) 79. This psychological-tension is embodied in the participant's metaphorical-therapeutic-intent.

The Sun 148 relates to a universal metaphor as the giver of life. The Sun 148 is the emitter of light and heat. The Sun 148 on a more esoteric level relates to the 'Law of Radiance.' The rays of the Sun awaken and give life. The radiant light of the Sun brings consciousness, hence the association of the Sun with the all-seeing eye. In India the Sun as Surya is the Eye of Varuna; in Greece as Helios, the Eye of Zeus; in Egypt it is the Eye of Ra. To the participant, he is taught that the Sun 148 is the inner eye that reveals repressed memories of the self.

These repressed memories need to come out in the light of the day. The Sun in its metaphorical sense relates to the ability of the participant to discover his bright mind, his warm heart, his potentially active body and his fiery spirit. The Sun 148 as a symbol connotes the act of giving life in a vital sense that is embodied in the image of the youthful king Tutankhamun, the Sun King. Through the symbolic construct (SC) 69 that is the Sun 148, the participant can learn how to extract his own Sun nature. The participant becomes the Sun in his human nature, he can become the central character in his own world. He becomes the embodiment of his own life giving powers through the symbolic construct (SC) 50*a* the Sun 148. In addition, symbolic constructs (SC) such as the Moon 149 and the Sun 148 can be singular symbolic containers (SCr) 52*a* when used as a single metaphorical embodiment of the participant's metaphorical-therapeutic-intent, as depicted in FIG. 2. However the preferred embodiment of the invention produces the desired metaphorical-polarity 79, and metaphorical-psychological-tension from the unique interplay of symbolic constructs (SC) 50*a* as the Sun 148 and the Moon 149. This desired symbolic interplay creates the inventions concept of the symbolic container (SCr) 128*a*. The symbolic container (SCr) is a key psycho-symbolic tool that is used and enabled by the inventions technological means and methods.

Referring now to FIG. 8, the present invention utilizes these powerful symbols in accord with other symbolic constructs (SC), via the aforementioned multi-level symbolic container (SCr) 128*a* that is embodied as a symbolic pathway (SP) 97*a* of the self. In fact each of the inventions symbolic container (SCr) 128*a* stories 97*a*, becomes an embodiment of the participant's life story, or the story he needs to, or so chooses to create through the inventions completely novel; processes, procedures, software, firmware and hardware means, methods and apparatus.

In FIG. 8, the depicted symbolic container (SCr) 128*a* contains selected and arranged symbolic constructs that enable a truly unique symbolic pathway (SP) 97*a*. Another important symbolic construct (SC) 50*a* embodied in this symbolic pathway (SP) 97*a* is the Tower 147. Surrounding the Tower 147 is flowing Lava 150 from a hidden Volcano, and a Spring flower 151, and the Mountain 91, upon which the Tower 147 is built. In the world of archetypal-psycho-symbolism; the metaphorical concept of the Tower 147 relates to rapid, and sometimes painful internal changes to ones perceptions about the self and life in general. The Tower 147, in terms of it's mythological context relates to building edifices of self concepts that are based false internal mythologies. These false self concepts effect ones entire 'life script.' In a Biblical context, the Tower 147 is the edifice of the ego that was built as a 'stairway to God.' This ego edifice was destroyed because of human arrogance. Quite often in the transformative journey, the Tower 147 relates to false-hoods that are generally tied to arrogant self concepts, or delusions connected to one's current human relationships. A person's current job may end abruptly. This abrupt ending is complete and painful surprise to the person. His whole world seems to be coming to an end. In this scenario, a person will experience rapid, painful change that hurts! After the initial shock, the person will probably slide into depression.

This symbolic pathway (SP) 97*a* metaphorical suggests that when one experiences these painful changes that there is always hope based upon one's directed interior and anterior actions. The message here is that change is inevitable, and one must have faith in one's own ability to overcome the interior and anterior obstacles that the abrupt life change causes. The core of the issue here is that the participant may need to change or purge himself of harmful and limiting self-concepts. That, the participant needs to change his internal mythology in order to affect the desired change that will lead to a better more complete life. For example, the symbolic construct (SC) 50*a* Flowing Lava 150 connects metaphorically to self-destructive change. The heat or friction from the Lava destroys the Mountain 91 around it. However, once the Lava cools new life is produced that is symbolized by the Spring Flower 151. This symbolic construct (SC) 50*a* connotes; that from the destruction of life limiting self-concepts, new life 'springs forth and arises anew.

Desired metaphorical-polarity 79*b* is therefore created when the participant 'experiences' the painful psycho-symbolic contrast created between the metaphorical Tower 147 concept and the Flowing Lava 150 concept, and the Spring Flower concept 151. That, sometimes the Tower 147 connotes an abrupt ending which produces a seemingly 'dead end.' The participant therefore must understand that the internal delusions represented by the Tower 147, must be burned away, and this 'burning' is represented by the Flowing Lava 151. However, the heat, or friction from the internal psycho-symbolic changes can create excruciating psychological pain.

Sometimes these processes can cause serious depression, also known as, 'the Dark Night of The Soul' in many mythological stories. This painful change that has transpired within the conscious framework of the participant's self view, is embodied in the Tower 147 and its metaphorical interplay with the Flowing Lava 150 that connotes painful but needed change. The hidden hope of the participant's salvation is embodied in the symbolic construct (SC) 50*a* Spring Flower 151 that arises from 'cooled lava' that has become part of the renewed Mountain 91, that metaphorically represents the participant's self conceptual core. The participant's 'Mountain core' 91, in fact relates metaphorically to the participant's stored memory 53. In addition to the visual symbolic constructs (SC) 50*a* depicted in the symbolic pathway (SP) 97*a*, there is also provided a plurality of other multi-sensory-stimuli; symbolic construct (SC) information. This non-visual symbolic material includes but is not limited to; sound effects, narrative voice overs, sound-vibration, tactile-position, applied heat or cool stimuli, specific and supportive olfactory stimuli, and other sensory stimuli sources. The participant can in fact experience and complete his metaphorical-therapeutic-intent without being stimulated by visual based symbolic constructs (SC).

This non-visual symbolic construct (SC) information is supplied by the invention's means, method and apparatus. This symbolic construct (SC) information can be used to provide metaphorical-symbolic-reinforcement, enable metaphorical-polarity, and amplify metaphorical-tension, measure the psycho-biological reactions and stress; and therefore embody, and enable the participant's metaphorical-therapeutic-intent. Human consciousness relates and interprets all sensory stimuli as symbolic constructs (SC) 50*a* regardless of the sensory stimuli source.

Figure 13:
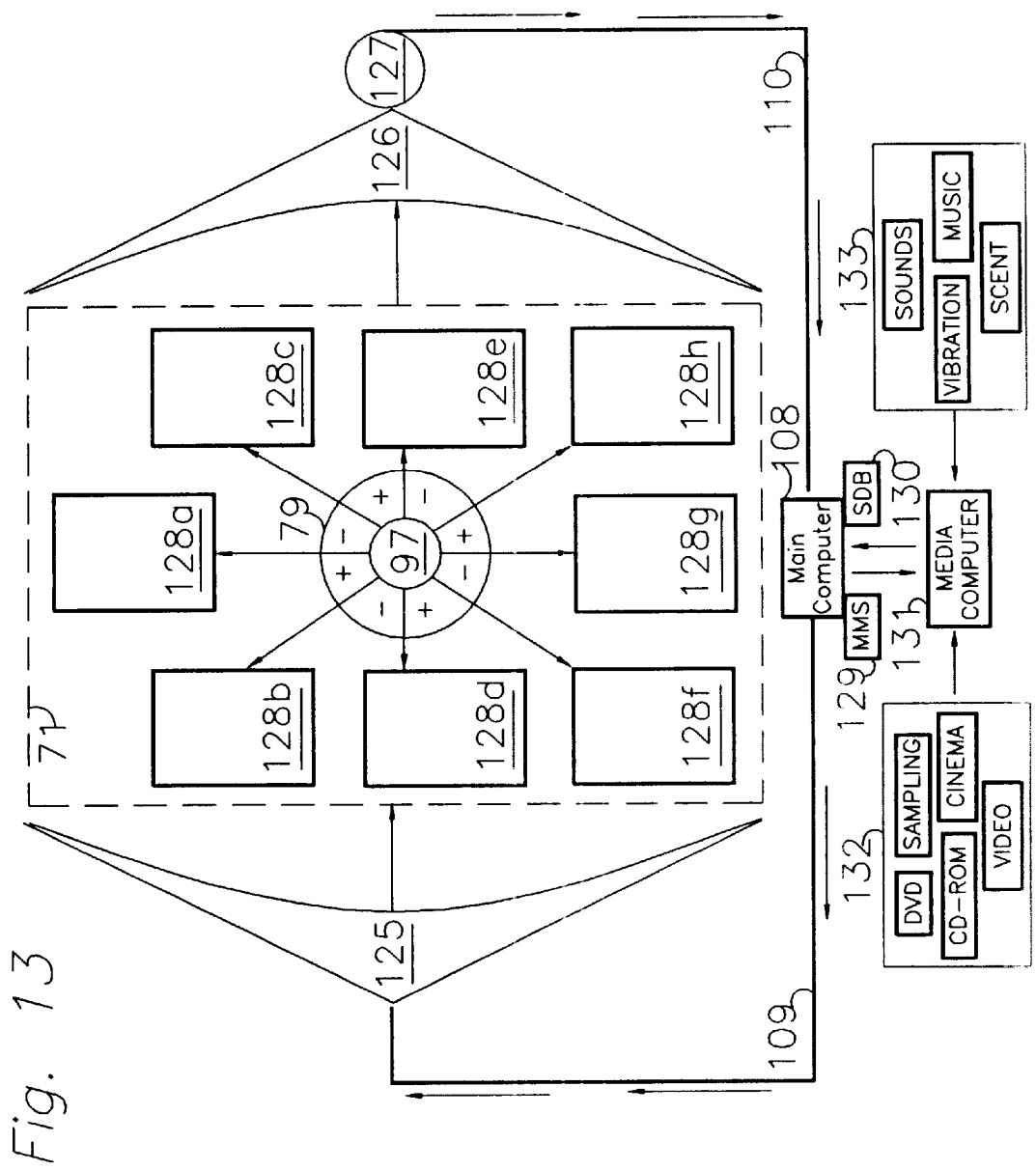
FIG. 13 depicts the ASSDM system with its planned multiple scenario means, embodied in symbolic quests, according to the invention.
Figure 14:
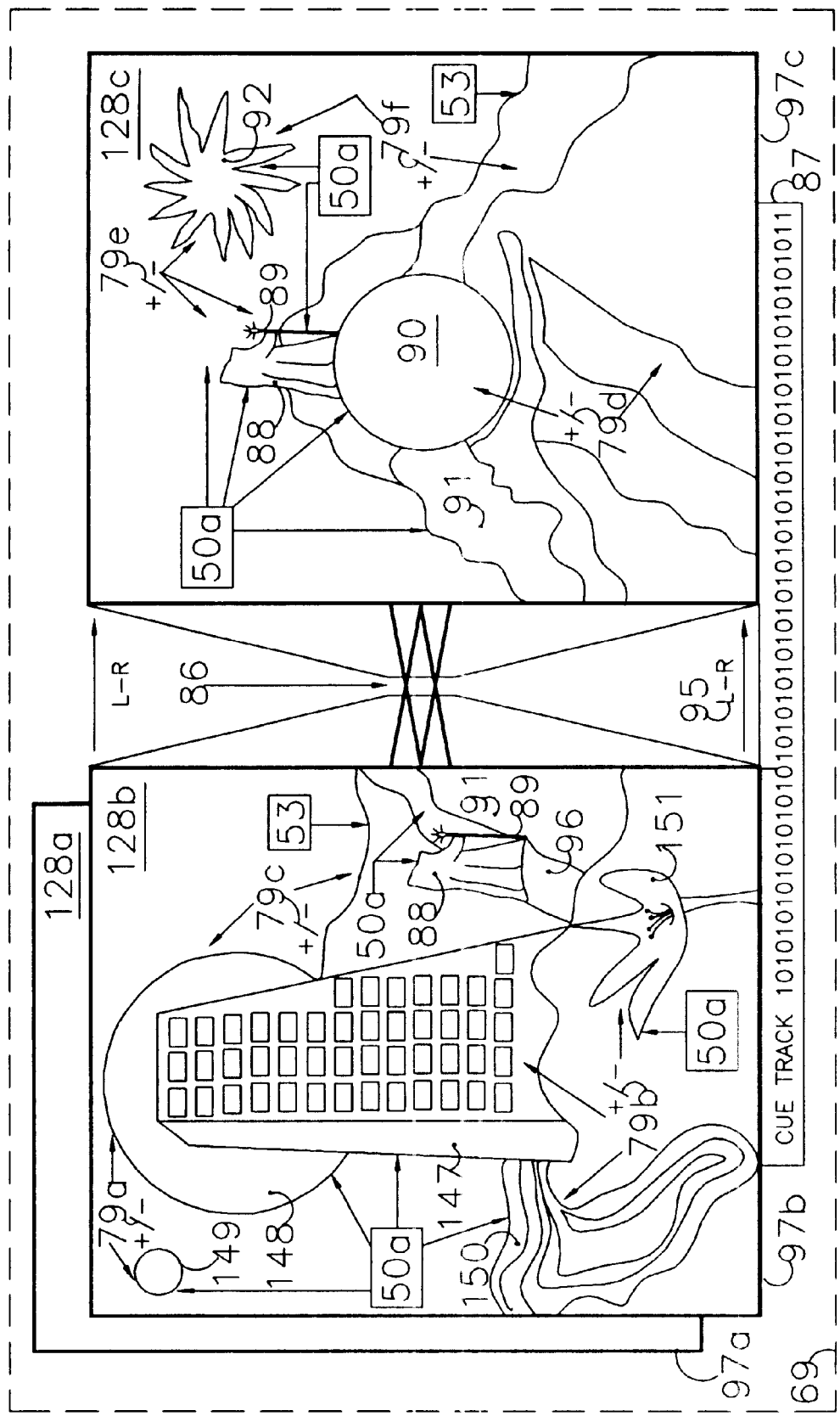
FIG. 14 depicts a cinematic style transition between one AMV event to another AMV event, according to the invention.

In FIG. 8, FIG. 14, two symbolic pathways (SP) 97*b*, and 97*c*, and the embodied symbolic containers (SCr) 128*b*, and 128*c*, are connotative continuations of the aforementioned symbolic pathway (SP) 97*a* and symbolic container (SCr) 128*a*. Three symbolic pathways (SP) 97*a*, 97*b* and 97*c* are codified components of the eight part randomly applied symbolic quest (RSQ) 70 as depicted in FIG. 3, and the planned and programmed symbolic quest (PSQ) 71 depicted in FIG. 13. These three symbolic pathways (SP) 97*a*, 97*b*, and 97*c* in fact tell a metaphorical-mythological 'story' of the participant's metaphorical-therapeutic-intent.

This depicted story can be used as a means to cause the participant to discover various psycho-spiritual-needs that he did not realize until being exposed to this symbolic quest (SQ) 69. This symbolic quest (SQ) can be formatted as an automatically configured, assembled and randomly applied symbolic quests (RSQ) 70 as depicted in FIG. 2, and FIG. 3. Once this story of the 'participant's self' is applied randomly in the inventions Stage Four, it is therefore determined by the retrieved analysis of the participant's psycho-biological EEG measurements 176 as depicted in FIG. 10. This 'random story' has relevant significance to the participant's metaphorical-therapeutic-intent. Once this is recognized by both the ASSDM facilitator and the participant, a planned and completely programmed and symbolic quest (SQ) 71, is therefore designed by the ASSDM facilitator and the participant. Therefore the inventions Stage Five is technically enabled by the inventions artificial intelligence means.

Referring to FIG. 8, and FIG. 14, during the self discovery processes experienced in Stage Four, the participant is exposed to the stress inducing aspects of the release of buried stored memory 53 based life event trauma (LET). In a metaphorical sense, a LET is the mythological 'devil,' or bedeviled aspect of the self. The inventions means and method thereby instruct the participant through the metaphorical-therapeutic-intent to embrace and explore the causality of this LET based 'bedevilment.' As Nietche said, "beware of casting out your devils because they may be the best part of you." Another words, it is healthier to know ones dark side, caused by life event traumas (LET) then to go through life denying ones devils. One must embrace one's totality completely in order to master the self.

The central aim of the present invention is to enable, through technological means, this intended transformative process. Life event traumas (LET) can invariably be one's inner salvation. These LETs can be used to strengthen ones resolve to attain mastery of the self, and live a healthier life instead of succumbing to the negative behavior caused by the blind or heretofore hidden impact of the life event trauma (LET). The LET is an embedded component of the participant's stored memory 53 that is metaphorically represented by the Mountain 91.

With refrnece now to FIG. 8, and FIG. 14, this three part abbreviated example of the eight part symbolic quest (SQ) 69 tells a story to the participant during the immersive experience of the AMV technological event 134 as depicted in FIG. 2. This selected AMV event 134 delivers the desired symbolic container (SCr) 128; propelled by the metaphorical-polarity 79a embodied in the selected symbolic constructs (SC) 50a. The very nature of the AMV technological experience 134, causes the participant to 'suspend belief' in the 'contained' old ways of feeling, thinking and behaving about the self. For the 'content' of the delivered symbolic container (SCr) 128, that is comprised of a plurality of selected symbolic constructs (50a), that in fact causes the desired 'suspension of beliefs.'

This psycho-symbolic therapeutic fact is due to the participant's 99 experience of the metaphorical-polarity 79b; that the experience of the metaphorical polarity 79b in fact causes the desired psychological-tension, and thus enables a movement within the stored memory 53, that is comprised of associated symbolic constructs (ASC) 51b. The new perception of the old memories therefore 'contain' the new perception based upon the participant's metaphorical-therapeutic-intent. The symbolic container (SCr) 128 is synonymous to Carl Gustav Jung's concept of the 'transcendent function.' The transcendent function is a mutual influence which is exerted between the ego or the 'I am principle,' and the self in the course of personality development and individuation. In terms of ASSDM the processes, the concept of 'I am' is defined by the relationship of the 'sense of self' that is connected to stored memory based symbolic constructs (SC) 50b as depicted in FIG. 2. We as a species tend to codify ourselves as an amalgamation of our past experiences. The invention's symbolic container (SCr) is the transport mechanism that contains the participant's metaphorical-therapeutic intent, embodied in specially arranged symbolic constructs (SC) 50a that in fact create the invention's symbolic container (SCr) 128. This symbolic container (SCr) simultaneously contains and embodies the experience of the participant's life event trauma (LET) 94.

The invention provides the technological AMV processes that envelop the participant in the transformative experience from the past, to the present and onto the future. As the participant experiences the symbolic quest (SQ) 69, and the symbolic container (SCr) that creates the numinous transference that in fact transforms the participant's perceptions of the past life event trauma (LET). As the invention's technological means, methods and apparatus continue to deliver the virtual reality based hypertext experience, a new more manageable perception of the LET emerges in terms of the participant's present day life situation and experiences. The symbolic container (SCr) therefore, becomes the participant in that he now identifies more the present perception of the symbolic container (SCr) instead of the symbolic quality of the life event trauma (LET) 94. The participant in fact becomes the embodiment of the metaphroical-therapeutic-intent that 'is' now the symbolic container (SCr), which is comprised of specially arranged symbolic constructs (SC) 50a, that are embodied in the symbolic pathways (SP) 97, that are technically and narratively linked to create the invention's symbolic quest (SQ) 69.

The participant's 99 reception of the new symbolic 'data' of embodied non associated symbolic constructs (NSC) 54b, contained within the technological parameters of the AMV event 134, and therefore transforms the NSCs into ASCs. Furthermore the AMV event 134 that delivers the aforesaid new 'symbolic data' causes the belief structures of the participant's critical judgement 135, to be disrupted. Because the bases of human critical judgement is derived from prior life experience (LE). And therefore, the most dominate and critical form of stored memory 53 is life event trauma (LET) 94, that is comprised of symbolic constructs (SC) 50b. When the critical judgement 135 processes are disrupted, the desired; 'suspension-of-belief' is attained.

Once attained, the new 'symbolic data' contained within the symbolic containers (SCr) 128, that are comprised of selected symbolic constructs (SC) 50b, that are embodied in the inventions symbolic pathways (SP) 69, that can be formatted as randomly applied symbolic quest (RSQ) 70, and/or programmed and planned symbolic quest 28 (PSQ) 71, become embodied with the symbolic construct (SC) 50b formats of the participant's 99 stored memory, thus creating the basis of the new perspective of the self. Thus the goal of attaining a new internal mythological story of the self is achieved. During the initial phases of the ASSDM experience, the participant 99 has revealed various symbolic themes that he feels might need to be addressed.

The facilitator then arranges for a generic symbolic quest (SQ) that is designed to deal with certain psycho-symbolic issues that all people tend to encounter in their lives. By being exposed to these generic quests, the participant becomes more familiar with what specific psycho-symbolic issues he needs to deal with. The invention is designed to act as a 'feedback-mirror' that takes the participant deeper and deeper into himself, until he is able to manage his internal mythological landscape more effectively. These generic symbolic quest programs are stored in databases that are integrated and controlled by the invention's artificial intelligence means, and retrieved from the main computer 108, and the media computer 131, and other specialized ASSDM computer operational data bases.

Figure 15:
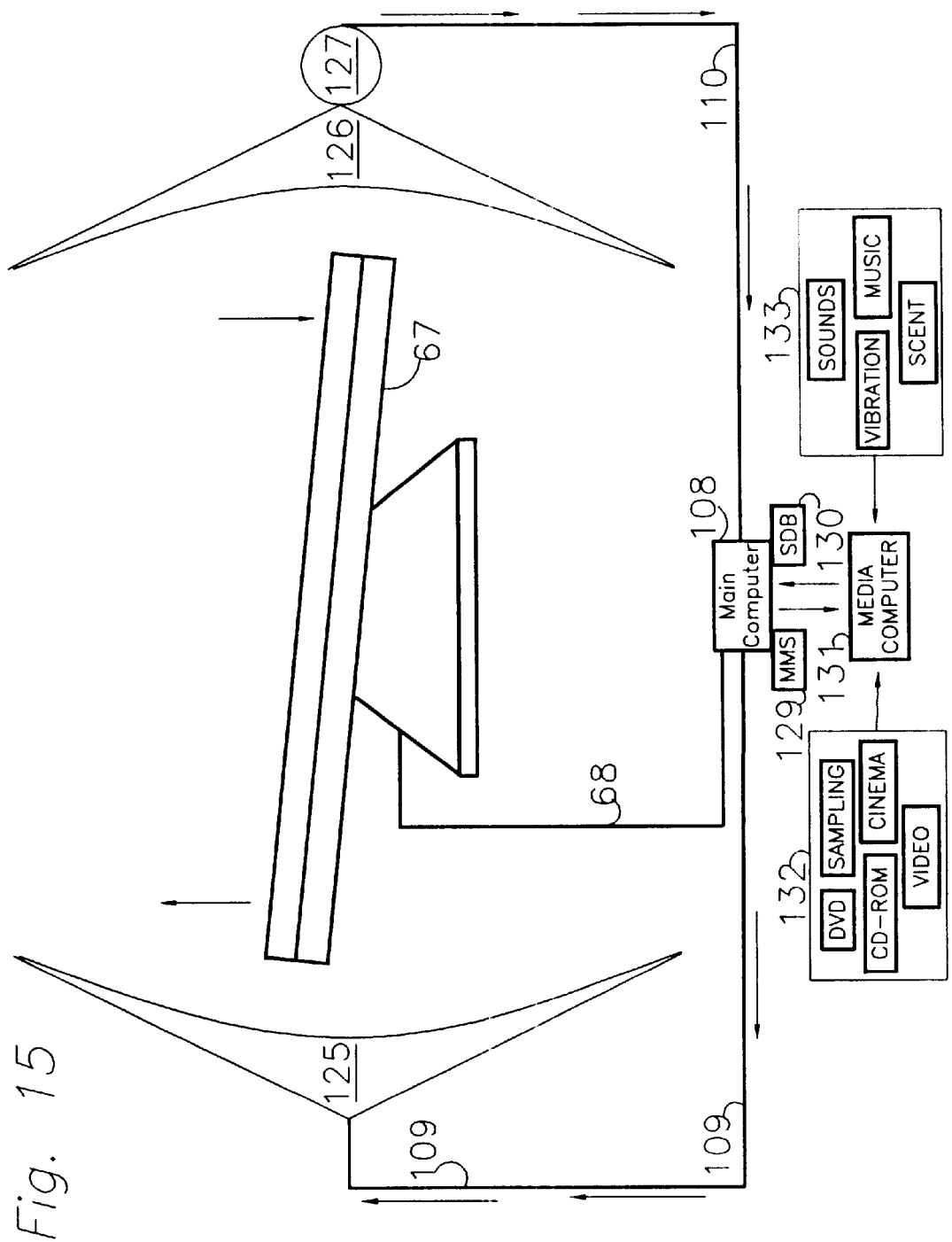
FIG. 15 depicts a tactile vibration platform integrated with the invention's artificial intelligence means, according to the invention.
Figure 17:
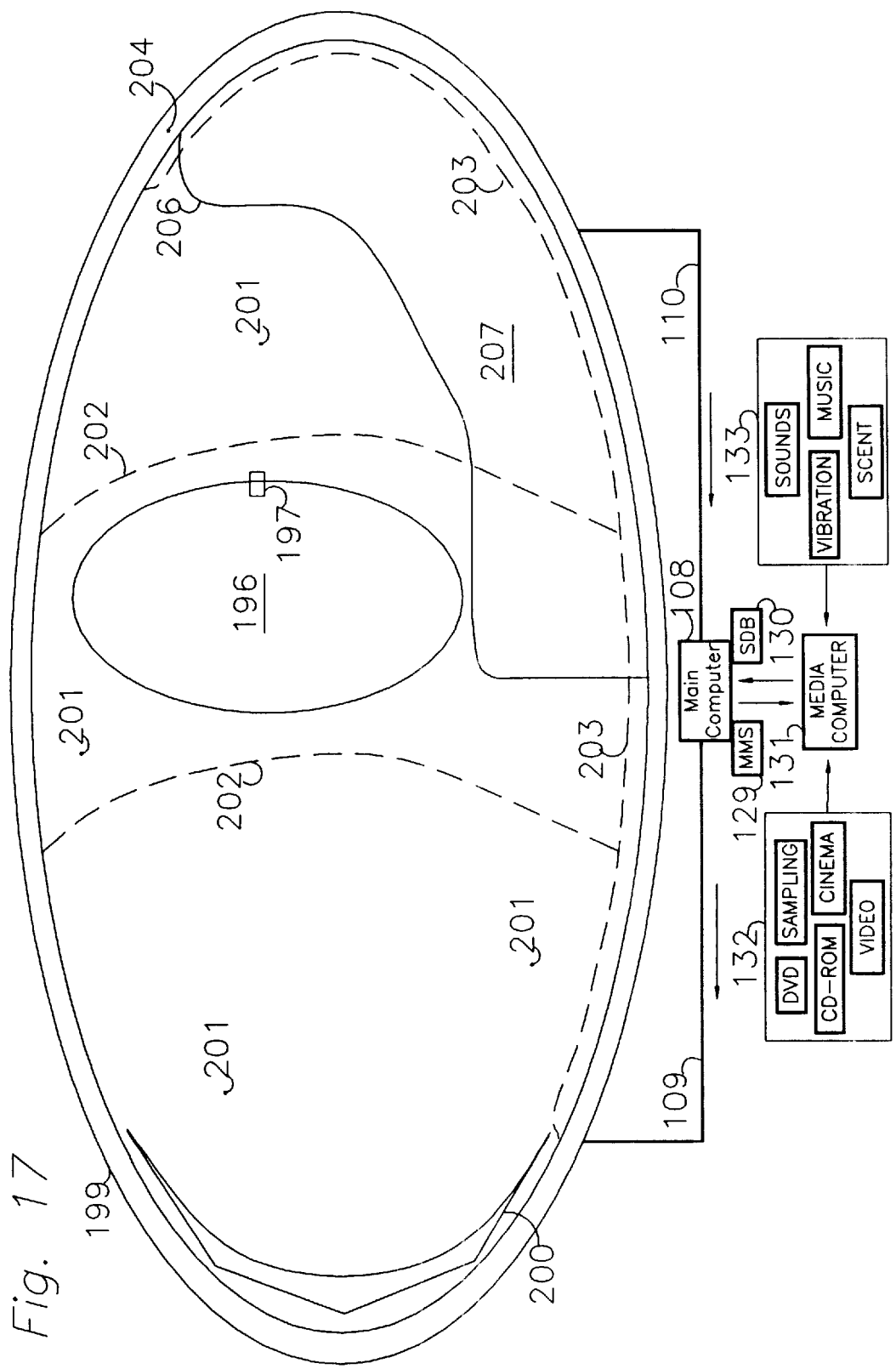
FIG. 17 shows the invention's Egg Room-AMV life simulator, according to the invention.

The specific symbolic quest (SQ) programs are derived from the pre-produced media sources 129, that are embodied in multimedia storage and transport apparatuses 132. Other types of visual, audio, vibration and other media 133 can be delivered to the participant 99 via the AMV apparatus. This includes such multi-media sources as video and audio information to an HMD 101 as depicted in FIG. 5, or vibration and sound based data to the holochair 107; or, to the tactile-position information can be sent to the tactile-position-wheel 152 as depicted in FIG. 4; or to the egg-room-hologram 199 as depicted in FIG. 17; or to the flotation tank 162 as depicted in FIG. 9; or to the tactile-vibration bed 67 as depicted in FIG. 15.

The multimedia sources 129 are technologically governed by the inventions media computer 131, the IMX system 185 and the connected time code and cue 'local area network' LAN 242 as depicted in FIG. 11. Referring to FIG. 2, once a facilitator initiates either an (RSQ) 70 or an (PSQ) 71 at the facilitator computer station 188 as depicted in FIG. 11, the Main computer 108, Media computer 131 take over the control of the multimedia storage and transport system 179. The media computer 131 causes the IMX non-linear, multimedia production system to initialize and operate in accord the specific type of media needed for a particularly designed symbolic quest (SQ).

With refernece now to FIGS. 2, 8, and 14, the symbolic quest (SQ) 69 is first randomly applied, and therefore is a randomly applied symbolic quest (SQ) 70. At this stage, a possible scenario of the participant's metaphorical-therapeutic-intent is embodied in an abbreviated form in contrast to the eight randomly applied symbolic quest (RSQ) 70 depicted in FIG. 3, and the programmed and planned symbolic quest (PSQ) 71 depicted in FIG. 13. Referring to FIG. 2, FIG. 8 and FIG. 14, the participant's abbreviated symbolic quest (SQ) 69 depicted in the three symbolic pathways (SP) 97a, 97b and 97c embody multimedia symbolic construct (SC) content that is applied and delivered via multiple AMV technological events. These AMV events are assembled cinematically via the invention's computer based artificial intelligence means; compiled as a multiform; multi-narrative; multi-sensory format. This particular symbolic quest (SQ) is randomly assembled, stored and retrieved for the purpose of activating a participant's internal thoughts and feelings about the self. These internal thoughts connote the participant's internal mythological thinking that relates to the participant's sense of well being. Most people have negative self-conceptual images that relate to "I am no good, I cannot measure up, and I am not worthy," and other such negative reinforcements. The symbolic content can be applied to the participant's senses in a sequential-linear format. Or, the symbolic content can be applied in a non-logical, non-linear abstract format.

Because of the intense sensory immersion experience of the AMV technological event 134 exposure to the depicted metaphorical content can in fact induce all types of psycho-biological responses. The invention's artificial intelligence means represented by the depicted main computer 108, media computer 131, media storage and transport means 132, and other such multi-media data storage and retrieval systems can apply hundreds of pre-produced and prepared generic symbolic quests (SQ) 69. These generic symbolic quests (SQ) can relate to all sorts of human behavior and self-awareness issues.

The applied format depends upon the particular ASSDM Stage; and the specific intended level of the stage the participant is experiencing, or, about to experience. For example, symbolic pathway (SP) 97a, metaphorically connotes the emergence or rising of a Tower 147, that represents a falsehood or a negative delusion about the participant's internal self view. The depicted symbolic container (SCr) 128a metaphorically connotes through applied multimedia such as; video, computer generated imagery, film sources, selected audio sources that include; supportive vocal narration, sound effect reinforcement of the narrative, vibration, artificial scent, applied heat, cold, and other sensory stimuli. The aforesaid sensory stimuli reinforces the desired metaphorical-therapeutic-intent embodied within the content format of the generic symbolic quest (SQ) that is designed to trigger and then reinforce the participant's awareness of possible internal psycho-symbolic issues.

The symbolic construct (SC) 50a Tower 147 as just thrust itself up through the Mountain side 91 that metaphorically connotes the participant's stored memory 53 as depicted in FIG. 2, FIG. 8, and FIG. 14. Furthermore, the Flowing Lava 150 metaphorically suggests that the 'heat' of metaphorical-tension 79b, that is caused by the thrusting Tower 147, and the resultant Flowing Lava 150 is symbolic of the psychological movement. This movement that transpires within the consciousness of the participant 99 must be endured in order to change his internal perception of what and whom he is in everyday life. The Spring Flower 151 is a symbolic construct (SC) 50a that metaphorically suggest that from the destructive quality of the Tower 147, that there is fact the hope of life changing renewal.

Referring to FIG. 14, the depicted symbolic pathway (SP) 97b embodies a symbolic container (SCr) 128b that further reinforces the participant's metaphorical-intent. For example, in this symbolic pathway (SP) 97b a Pathway 96 appears as does a Wizard 88 whom uses a Staff of Light 89 to assist him while he travels this Pathway 96 of self discovery. This AMV technological event as depicted in FIG. 2, and FIG. 14, reinforces the depicted narrative from the aforementioned multi-media sources by suggesting that the Wizard 88 is in fact the participant who is travelling this arduous Pathway 96. The Wizard's Staff 89 is symbolic of the participant's 'guiding or inner light' or ability to enact the desired psychological change within the self. The next part of this abbreviated symbolic quest (SQ) 69 is the third symbolic pathway (SP) 97c, that embodies the desired metaphorical-therapeutic-intent embodied in the 'goal' of the depicted symbolic quest (SQ) 69. The third part appears within to the senses of the immersed participant via a conventional cinematic transition 86 that is in fact a 'lap dissolve' that occurs from screen left to screen right 95. When the third symbolic pathway (SP) 97c fully appears to the participant's senses the embodied symbolic container (SCr) 128c begins to invoke its metaphorical-symbolic content.

The participant further learns to truly experience his own inner transformative journey, because the Wizard 88 is the metaphorical embodiment of his true self. The arduous Pathway 96 depicted in the previous symbolic pathway (SP) 97b as now been transformed into a Solid Sphere 90 that connotes a sense of worldly completion. In fact each symbolic construct (SC) 50a can be separately and electronically cataloged, stored and transported in terms of its metaphorical relevance to the instant symbolic quest (SQ) and the participant's metaphorical-therapeutic-intent or therapeutic agenda. During an immersive AMV event each separate symbolic construct (SC) 50a can be layered or overlaid by the use and creation of computer generated imagery and or computer based animation in conjunction with supportive narrative based audio, sound-transducer-vibration, external lighting and other multi-media special effects. This is especially effective in the invention's egg room environment.

The Light of Staff 89 has guided to his star self, represented by the symbolic construct (SC) 50a the Star 92. There exists metaphorical-polarity 79d between the old memories depicted by the rough chaotic Mountain 91 and the concentrated, refined and well organized sense of self represented by the refined and well defined Solid Sphere 90, upon which the participant-Wizard 88 now stands. The Star 92 as a symbolic construct (SC) 50a metaphorically connotes the unlimited potential that resides within the participant's true self. The symbolic polarity 79e in fact 'propels' the participant 99 Wizard 88 towards his inner Star 92 light.

This randomly applied and generically structured symbolic quest (RSQ) 70 is assembled from the invention's vast library of symbolic pathways (SP) that can be retrieved either randomly from a spooler-assembler program embedded in the main computer 108 and the media computer 131 as depicted in FIG. 2, and FIG. 11. Furthermore, the same generically structured symbolic quest (SQ) 69 can be formatted in a planned and programmed scenario, in accord with the specific details embodied in the participant's metaphorical-therapeutic-intent. These same generic symbolic pathways (SP) can in fact be utilized in the invention's planned and pre-programmed symbolic quests (PSQ) 71 as depicted in the FIG. 13. The same general narrative structure can be applied to the creation of a randomly applied symbolic quest (RSQ) 70 as shown in FIG. 3.

The inventions innovative software, firmware and hardware means embodied within the technological structures of the main computer, media computer, that control and manage all the invention's special use of the associated ASSDM virtual reality multi media and multi sensory apparatus (AMV) complete an entirely novel behavior modification system. Additionally, the invention provides complete artificial intelligence control and management of the specially designed AMV apparatus. Said AMV apparatus can be located within a specially designed ASSDM therapeutic facility and or located within the participant's office of home.

The invention's specially designed randomly applied symbolic quest (RSQ) planned and programmed symbolic quest (PSQ) can be completely controlled and delivered to a private personal computer (PPC) and the inventions portable consciousness machine (CM) via the internet world wide web (WWW). These aforementioned symbolic quests (SQ) can be formatted as symbolic-quest-therapeutic-prescriptions (SQTP) that contain linear and non-linear AMV sequences that embody the invention's AMV-REM programming techniques. These specialized virtual reality sequences can be recorded and stored within the technological structures of compact disc read-only memory (CD-ROM), digital video disc (DVD), recordable compact disc (RCD), Sony Play Station Disc™, Nintendo Game cartridges™, digital video tapes (DV), analog video tapes (AV), and selected audio only digital and analog storage and playback mediums.

Furthermore, the invention provides for the delivery of SQTP; real time video and audio to the participant's wearable consciousness machine (CM) via a wireless telephony or satellite network. Such prior art wearable devices as the Private Eye which generates a full size virtual computer screen display in front of the participant's visual perceptions that in fact appears to float a few feet in front of the participant and fits in the palm of his hand. This prior art device enables personal computer interaction in a very small medium. However, the present invention provides totally unique usage and configuration of such prior art devices.

Referring now to FIGS. 8 and 14, embodied within the artificial technological structures of the inventions AMV based symbolic quests (SQ) are cue and control information contained in the aforementioned multimedia storage and retrieval mediums. This cueing information is also known in the art as 'house keeping information' that is embedded within the formatted structures of video tapes, CD-ROMS, DVDs, DVs, and laser discs (LD) 87. The present invention uses this conventional information to simultaneously monitor the participant's physiological reactions to the symbolic content of the selected symbolic quest (SQ), and therefore further insert new symbolic information stored in the selected multimedia record and playback apparatus in accord with the participant's metaphorical-therapeutic-intent. Furthermore, this same control and cue information 87 is used to control the invention's selected AMV apparatus. The main computer 108 and media computer 131 contain the invention's unique software and firmware means that automatically cues the symbolic content, that is in fact contained in the stored symbolic programs. These symbolic programs are structured as symbolic pathways (SP) 97, that further contain symbolic containers (SCr) 128 that in fact create the invention's symbolic quests (SQ) 69 regardless of the intended planned or randomly programmed format.

For example, referring to FIG. 4, FIG. 10, and FIG. 11, the participant paces himself in the invention's tactile-position-wheel 152. Embodied within the technological structure of the wheel are powerful servo-motors 159 that position the participant's body in accord with the symbolic-content of the selected and applied symbolic quest (SQ) 69. For example, if the symbolic content of the AMV technological event indicates that the participant needs to be positioned to simulate flying like a bird, the main computer 108 instructs the wheel to move in relation to the aforesaid symbolic content. The wheel 152 is comprised of a primary wheel 153, a secondary wheel 115 and a platform 158 that enables the participant to be positioned in almost unlimited attack attitudes. The send and receive cable sends appropriate electrical voltage to the embodied servos 159 and is governed by the inventions main computer 108 and media computer 131, as a result of what read by the multimedia-transport systems 179 cue track 87. Simultaneously, the main computer 108 reads and responds to the participant's physiological responses via sensors contained within the body suit 182 and head mounted display (HMD) 101 and revealed in the EEG readouts 176 as depicted in FIG. 10.

The successful operation of the electrooculosymbolic system requires little training of the participant. The measured brain waves that the ASDM technological system respond to, are emitted simply by the participant focusing his attention to the displayed, heard, and felt symbolic constructs (SC), that are embodied within specially arranged symbolic containers (Scr), that comprise the selected symbolic quests(SQ). The SC are technically and narratively linked. The electrooculosymbolic system and the electronically linked ASSDM technological AMV apparatus system therefore responds to a simple exercise of the participant's will in accord with his metaphorical-therapeutic intent.

This intent or therapeutic agenda is embodied in the specially arranged symbolic Scr that contain the technical indicators of where the participant is focusing his attention to with respect to how his brain waves and specific occipital flashes are measured and analyzed. Upon analysis, the ASSDM multi-media transport system responds with respect to the linear and non-linear psycho-symbolic content of the AMV event narrative, that comprises a technically linked cue track and SC that embody hidden pulses that are detectable to the participant's eye ocular mechanisms.

This symbolic content is tracked by the main computer 108 and media computer 131. These computers 'read' the cue track 87 contained within the substrate of the selected multimedia storage and transport system 179 via the invention's time code and cue system local area network (LAN) 242. Furthermore, the participant's physiological and electromyographic signals for tracking muscle responses are technologically coupled to the participant's immediate reactions to the symbolic content that in fact is experienced by the participant during an AMV event. Other consciousness reactions are also simultaneously tracked by reading his brain waves, heart rate, muscle tension, breathing rate, and by simultaneously measuring the occipital flash rates revealed in the invention's aforementioned electrooculosymbolic processes and procedures. The invention also provides the means and method of tracking the participant eye movement and position in relation to the perceived symbolic content being immediately experienced during the invention's symbolic quest (SQ) that is embodied in the inventions AMV technological sensory immersive event.

Referring to FIG. 5, depicted here along with the invention's holochair 107 is the HMD 101, a physiological sensor headband 106, the output signal cable 110 of the sensor head band and the audio video input signal cable 109. This input cable 109 is connected to the audio/video apparatus contained within the HMD 101, that in fact delivers the symbolic content to the participant's senses embodied in the invention's symbolic quests (SQ). The output cable 110 is directed connected to the electrooculosymbolic amplification system that comprises a brain occipital flash amplifier 102. The tiny signals detected by the electrodes first need to be amplified so that they are many thousands of times stronger. The main technical difficulty is that small amounts of electrical noise can easily become amplified as well unless certain technological precautions are taken. The invention provides for a conventional differential amplifier. This device is contained within the signal amplifier 102, and amplifies only the voltage between two points. This tactic works because most sources of electrical noise tend to effect all signals equally. This system is also shielded from the invention's other AMV apparatus and the inherent magnetic fields thus emitted.

The electrooculosymbolic system also includes an analog to digital converter 103. The amplified voltages need to be translated to a form that the main computer 108 can understand. To accomplish this task, specialized circuit call an analog-to-digital converter repeatedly samples the incoming signal at a cyclical rate of 4,000 times a second. This circuitry then converts the voltage levels to series of digital/binary numbers, e.g., zeros and ones. The precision of this conversion is such that the error introduced by the translation algorithm is limited to a small fraction of a percent of typical signal levels. This system also includes a digital signal processor (DSP) 104. A DSP integrated circuit is designed to perform certain numerical calculations swiftly and efficiently. The invention's electrooculosymbolic contains this DSP so that it acts to extract important features of the participant's measured physiological reaction signals and the sequence of numbers it receives from the A/D converter 103 and to recognize particular patterns in this data stream. Then, using these results, it recognizes which muscles generated the original electrical signals that emanate from the participant's reactions to the invention's symbolic content.

Another important part of the invention's electrooculosymbolic system is the optical isolation component 105. Because electric shock can occur whenever electrodes on the skin are connected to a high-voltage apparatus, precautions have to be taken to avoid injury. In this system the electrical signal is interrupted at one point and transformed to an optical signal that is transmitted over a short distance to the main computer 108. By breaking the electrical path with an optical link, the signal can pass unimpeded. The electrical signals are generated by eye movements, and the flash and movement rates of the symbolic constructs (SC) and symbolic containers (SCr) detected by the participant's eyes. The participant's eyes are directly connected to the participant's occipital lobes that generate flash rates that directly correspond to the movement and flash rates of symbolic content delivered to his senses by such AMV apparatus as the HMD 101.

The main computer 108 then further detects and determines what additional symbolic content that needs to be reinforced and cued and retrieved from the invention's media transport system as depicted in FIG. 11, governed by the cue track 87 data bits directly associated with the symbolic content of the selected pathway (SP) 97*a*, 97*b*, and 97*c*, that is comprised of selected symbolic constructs (SC) 50*a*, that are further embodied in the selected symbolic containers (SCr) 128*a*, 128*b*, and 128*c* as depicted in FIG. 8, and FIG. 14.

Each symbolic construct (SC) 50*a* can emanate and display hidden flash rates that are detectable to the participant's eye and measured by the invention's electrooculosymbolic system. For example, referring to FIG. 6, there is depicted a cathode ray tube (CRT) and/or liquid crystal display (LCD) stereo viewer 112*a* that is an integral part of the HMD 101. Inside the stereo display 112*b* is projected the selected symbolic constructs (SC). These squares 120, 121 and 124, circle, 122 rectangles 118 and 119 and ellipses 123 represent basic configurations of symbolic constructs (SC). These symbolic constructs (SC) are embodied in symbolic containers (SCr) that are integrated into selected symbolic quests (SQ) and projected to the participant's visual senses during an AMV event, is further embodied within one or more the invention's selected therapeutic stages.

Figure 6:
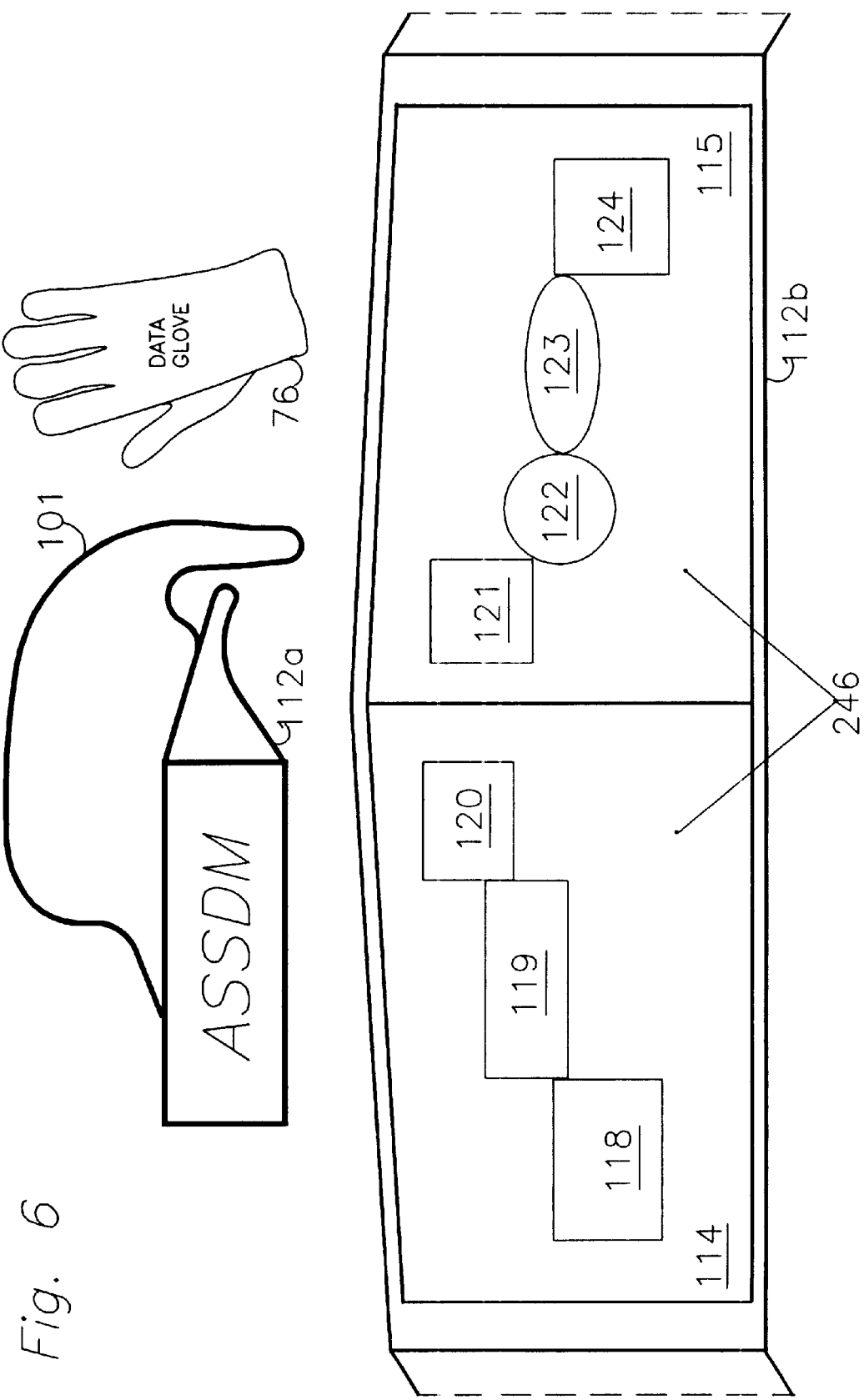
FIG. 6 illustrates the HMD and its cathode ray tube (CRT) display while in projecting electrooculosymbolic-symbols, according to the invention.

Each of these basic symbols can relate to and represent any of the aforementioned symbolic constructs (SC) 50*a* as depicted in FIG. 8 and FIG. 14. Referring to FIG. 6, each of the squares can have unique flash or movement rates that are detected, measured and evaluated by the invention's electrooculosymbolic system and the main computer 108. For example the rectangle 118 can have a hidden flash or pulse rate of three per second. The rectangle 199 can have pulse rate of two per second. The square 120 can have a pulse rate of 1.5 pulse per second. The square 121 can have pulse rate of four per second. The square 124 can have a pulse rate of five per second. The circle 122 can have a pulse rate of 10 per second and the ellipse can have a pulse rate of 15 per second. Depending upon the metaphorical relation of each of these simple symbolic constructs (SC) much participant pattern attention tracking information can be accurately detected, measured and evaluated by the main computer 108 and by a an ASSDM facilitator.

The facilitator observes the participant's reactions when seated at his physiological monitoring station 189 and his symbolic quest (SQ) observation terminal 188, and the electrooculosymbolic terminal 187 as depicted in FIG. 11. The electrooculosymbolic terminal 187 displays what symbolic construct (SC) the participant is focusing on, so that the facilitator can also evaluate various aspects of the metaphorical-polarity process and its resultant psychological stress.

In FIGS. 6, 8, and 14, these represented flash and movement rates can be embedded in each depicted symbolic construct (SC) 50*a*. The multi-media narrative content, that is directly and electronically connected and synchronized with its associated cue track 87 data bits, and synchronized with the particular flash or movement rate of the symbolic construct (SC) 50*a* the participant is focusing his attention, therefore determine what additional symbolic content information the main computer 108 selects to reinforce, for the desired therapeutic purpose. Also, the main computer 108 can determine that the participant's current focus is causing him to much physiological stress and therefore can diminish the impact of the current symbolic quest (SQ) content or shut the instant AMV technological event down completely.

For example, if the participant is experiencing negative stress that is being measured by the invention's physiological apparatus in real time while gazing at the hot flowing Lava 150, or the Tower 147, the invention's electrooculosymbolic system simultaneously measures the flash or movement rates of the hidden pulse signals embedded within each of these symbolic constructs (SC) 50*a*. This act of measuring physiological levels, while the participant is experiencing the stress identifies what part of the symbolic quest (SQ), that is comprised of multiple symbolic pathways (SP), the further is embodied in selected multiple symbolic containers (SCr), that is constructed on selected symbolic constructs (SC) that contain the hidden pulses. The movement of selected symbolic constructs (SC), while the participant is observing them can also measured.

This measured and retrieved information combined with the main computers 108 software and firmware control, then can diminish the impact by adding soothing music. Other psycho-symbolic diversions such as narrative suggestions, or vibrations, or artificial scents, or cooling temperatures and other supportive sensory stimuli delivered by the media computer 131, and the invention's multimedia transport system 179 as depicted in FIG. 11.

Another important aspect of this process example, if the participant is focusing his attention on the Wizard 88 symbolic construct as depicted FIG. 14, and he is experiencing reverie, and other positive emotions thus measured by the inventions EEG system 178 and physiological measuring devices. Then the multimedia narrative can be reinforced to support the positive effects of the metaphorical-therapeutic-intent as command and controlled by the main computer and the ASSDM facilitator. All ASSDM AMV apparatus can be controlled, positioned and managed in accord with the contained narrative as well.

With reference now to FIG. 6, the inventions also provides for a unique infrared eye movement tracker 246 that measures the focal position of the participant's eye in relation to the flash and movement rate of the currently observed symbolic construct (SC) represented by the aforementioned squares, circles, rectangles, and ellipses. This system operates in conjunction with the invention's electrooculosymbolic system. The CRT/LCD display also generates an infrared field 246 that measures the focal position of the eye by the reflectant qualities of the participant's cornea-to-retina line-of-sight which is in fact reflected from the retina back to the invention's infrared field. This eye position information is sent back to the invention's electrooculosymbolic system and evaluated by the main computer 108. The electrooculosymbolic system further measures the difference in voltage generated by the infrared light first fed to the HMD, and then it measures the difference of the infrared light reflected back to the infrared field from the participant's eyes. There is a fundamental law of reflectance at work here. In that what ever the measured percentage of light generated from its source is, the light reflected back is always less by a measured percentage rate. The detected difference and its pinpointed reflectant focus on the generated infrared field, therefore determine the position of the participant's eyes. Again, the position of his eye, the symbolic construct (SC) he is focusing upon, coupled with it's preprogrammed flash and movement rate determine what the main computer 108 needs to do to in relation to reinforcing or diminishing what symbolic content and its psychological impact upon the participant's senses.

Figure 7:
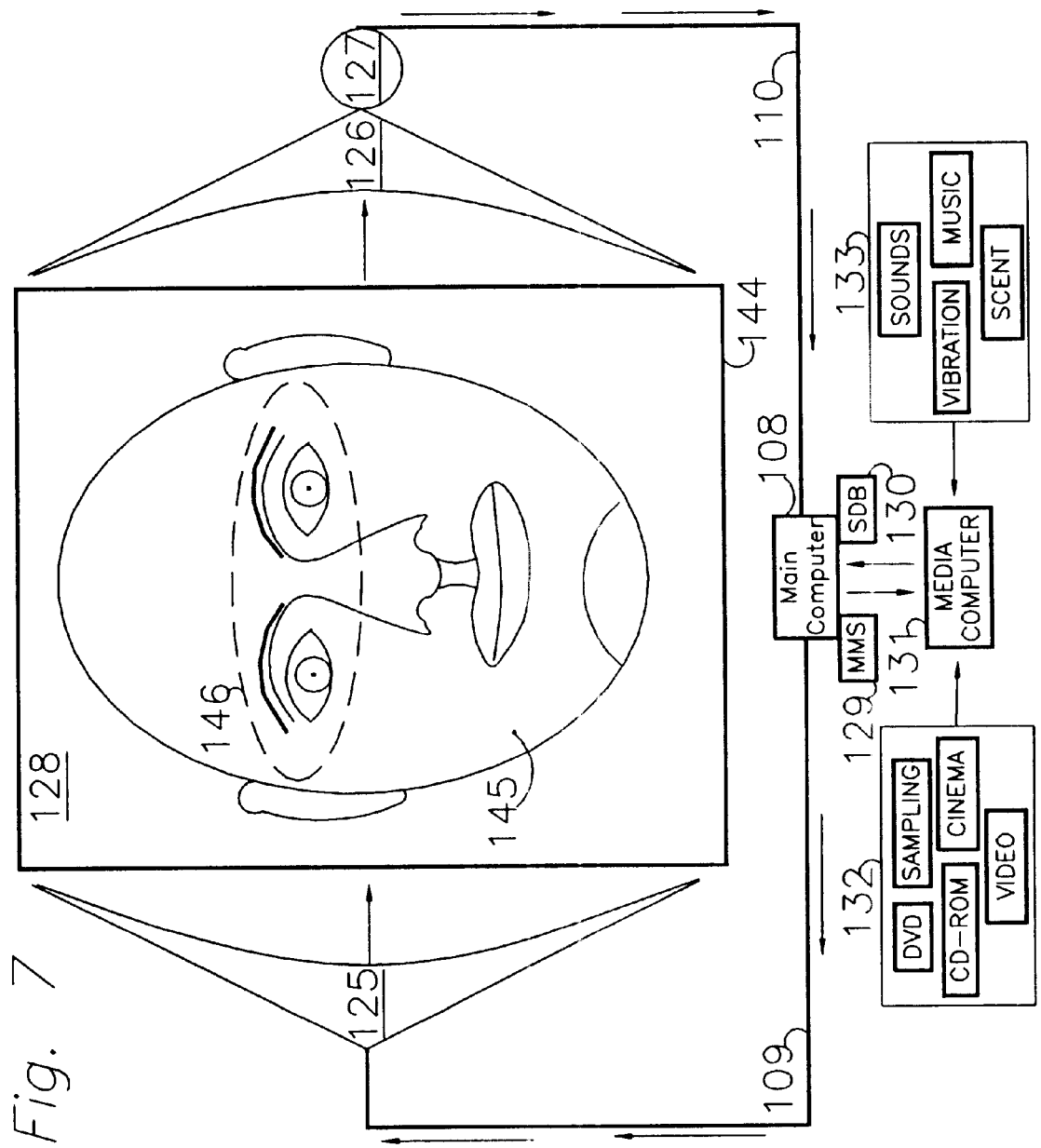
FIG. 7 illustrates the facial expression system as symbolic container that creates a life-experience-simulation (LES), according to the invention.

Referring to FIG. 7, depicted here is a symbolic container (SCr) 128 that is configured to project a computer generated morphed FIG. 144. The human face 145 is derived in much the same way a forensic illustrator creates the image of missing person or a wanted criminal. The invention utilizes the creation of human face in order to recreate the particulars of a life event trauma (LET) that may be caused by a parent, a sibling or some other person that may have contributed to a participant's earlier traumatic experience. For example during the preverbal stages of a child's early life, various traumatic events associated with a mother or father's face can cause life long dysfunctional reactions. What is especially crucial during these earlier life events is how the child perceives the expression around eyes 146 of a significant person whom may have dominated their earlier life. The invention uses this fact to revisit this traumatic experience by recreating the facial expressions and associative narrative multi-media stimuli so that the participant can revisit the life event trauma (LET) as an adult so that a particularly traumatic event can be understood and its impact significantly diminished. By combining this method with the invention's AMV-REM means and method a new therapeutic paradigm is created within the confines of the invention's artificial intelligence based apparatus.

Figure 12:
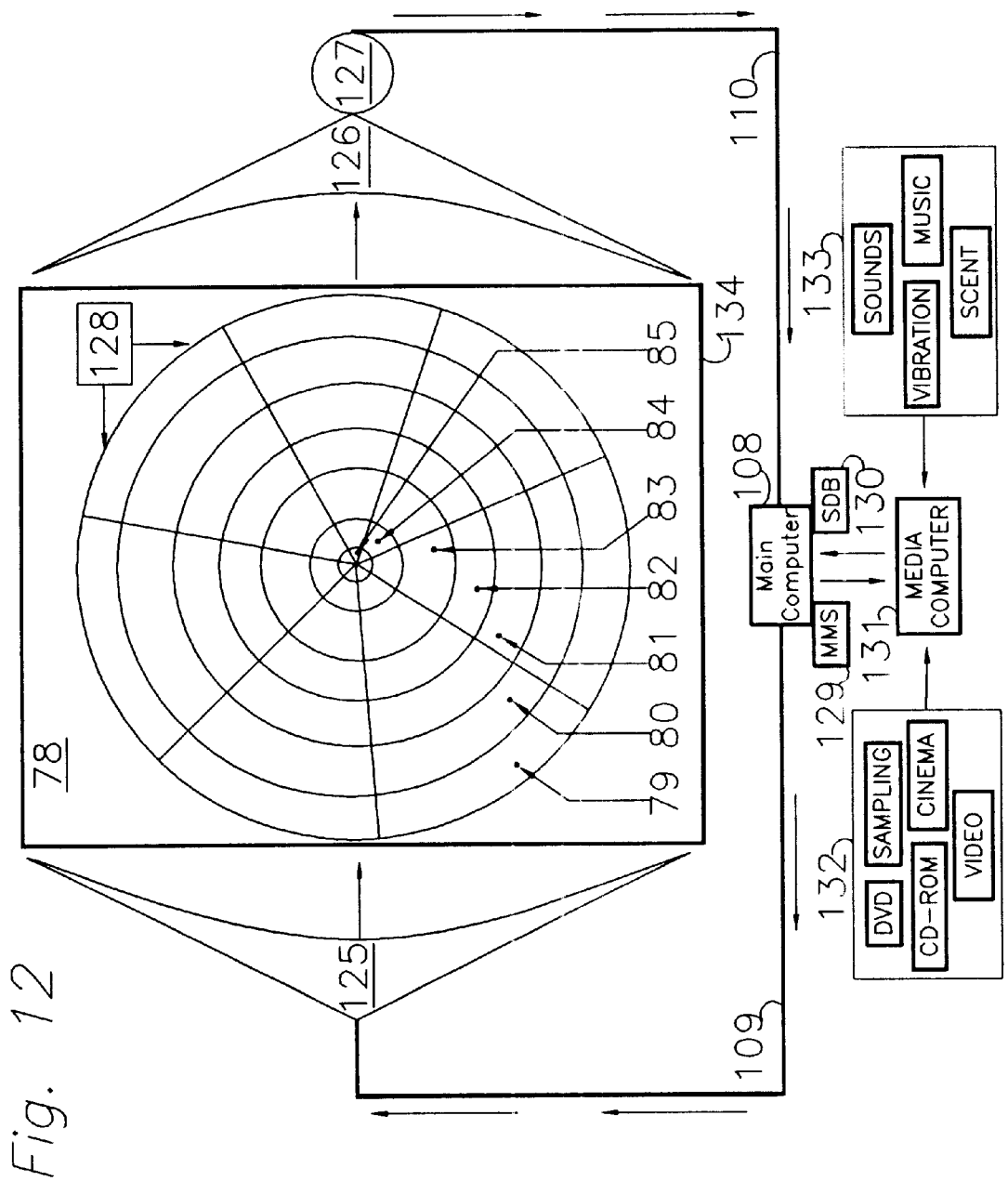
FIG. 12 depicts the usage of an abstract symbolic container, according to the invention.

In FIG. 12, here is an abstract circular mandala 78 that is a symbolic container (SCr) 128 used to create a perceptual convergence. Each circle or ring 79, 80, 81, 82, 83, 84, and 85 projects a different color and flash rate. This image can be used for the purposes of inducing relaxation, and subliminal programming of person's consciousness. There are many patterns that can be generated using this seven-level mandala. Coupled with linear and non-linear narrative structures, and further combined with the inventions AMV-REM techniques many different types of desired psychological results can be realized coupled with the participant's metaphorical-therapeutic-intent.

Referring to FIG. 17, the present invention provides for a unique 'consciousness simulator,' as known as the 'egg room.' This simulator is derived from earlier flight simulators used by flight training schools. However there is only a tangential relationship between the egg room and prior art simulators. The egg room hologram 199 is uniquely constructed to transmit heat and cold through the walls that are filled with colloidal fluid 204 and other matter that transmits, heat, cold and sound vibration to pinpointed locations within the structure of the room. The televisor walls 201 project specially selected symbolic quest (SQ) without the need of a participant wearing any special AMV apparatus. The egg room 199 is the complete multi-sensory apparatus. The participant enters the egg room 199 through a door or hatchway 196. The latch 197 is set flush in the curved wall as to not of noticeable to the participant's visual senses while being immersed within an AMV multi sensory event. There is provided a main curve rear projected or LCD screen 200 that is used to project specialized symbolic quests (SQ) when the televisor walls 201 are not used. Or, the screen 200 is used in conjunction with the televisor walls 201. There is also provided a colloidal fluid filled couch or bed 207 that moves on flush mounted tracks for lateral side-to-side movement 202 and forward and reverse movement 203. This couch or bed 207 shapes itself via software, firmware and hardware means depending upon the narrative multi-sensory information contained within the selected symbolic quest (SQ).

The present invention also provides for specialized internet worldwide web based ASSDM based psycho-symbolic services. Referring to FIG. 18, there is provided a specialized private personal computer (PPC) based programs that deliver real time video and audio programming via the internet. The invention provides for its own fully integrated internet service provider (ISP) 72 network that serves an unlimited number of participant's whom choose to access and utilize ASSDM services that originate from a specialized cyber center 228. Each PPC 75a, 75b, 75c, 75d, 75e, 75f, 75g and 75h is interfaced with an optional specialized head band that contains EEG sensors 106a, 106b, 106c, 106d, 106e, 106f, 106g, and 106h. Additionally there is provided a hard wired or wireless EEG sensing and interpretation device 205a, 205b, 205c, 205d, 205e, 205f, 205g, and 205h. These wireless devices transmit the participant's EEG traces and aforementioned occipital flash data to the PPC that in turn relays to the ASSDM cyber center 228 via the internet world wide web and the dedicated ASSDM ISP 72 for real time evaluation.

This system operates essentially the same way as the aforementioned ASSDM facility AMV system and apparatus. The only real difference is just the participant's location, and also there less immersive intensity with the aforementioned ASSDM internet based services. Also, it is assumed that most internet based participant's have experienced the ASSDM facility center experience, and in fact utilize the ASSDM internet services for psycho-symbolic reinforcement by periodically downloading to updated symbolic prescriptions that relate to his on-going metaphorical-therapeutic-intent.

There is also provided real time video conferencing via the internet. For each PPC is supplied with and connected to a small digital video camera, 229a, 229b, 229c, 229d 229e, 229f, 229g, and 229h. Real time video and audio can be provided with such software as Motorola's TrueStream™ video software that enables high quality video and audio in real time using 28.8 BPS or higher speed modems. The invention uses such software to enable its innovative psycho-symbolic therapeutic services. This wearable real-time multimedia retrieval and playback system, can be used by the participant to download symbolic quest (SQ) prescriptions. These symbolic quest (SQ) prescriptions can be downloaded to the PPCs hard drive, and or to the aforementioned real time video and audio transport and storage systems such as digital and analog videotapes and recordable compact disc.

Figure 21:
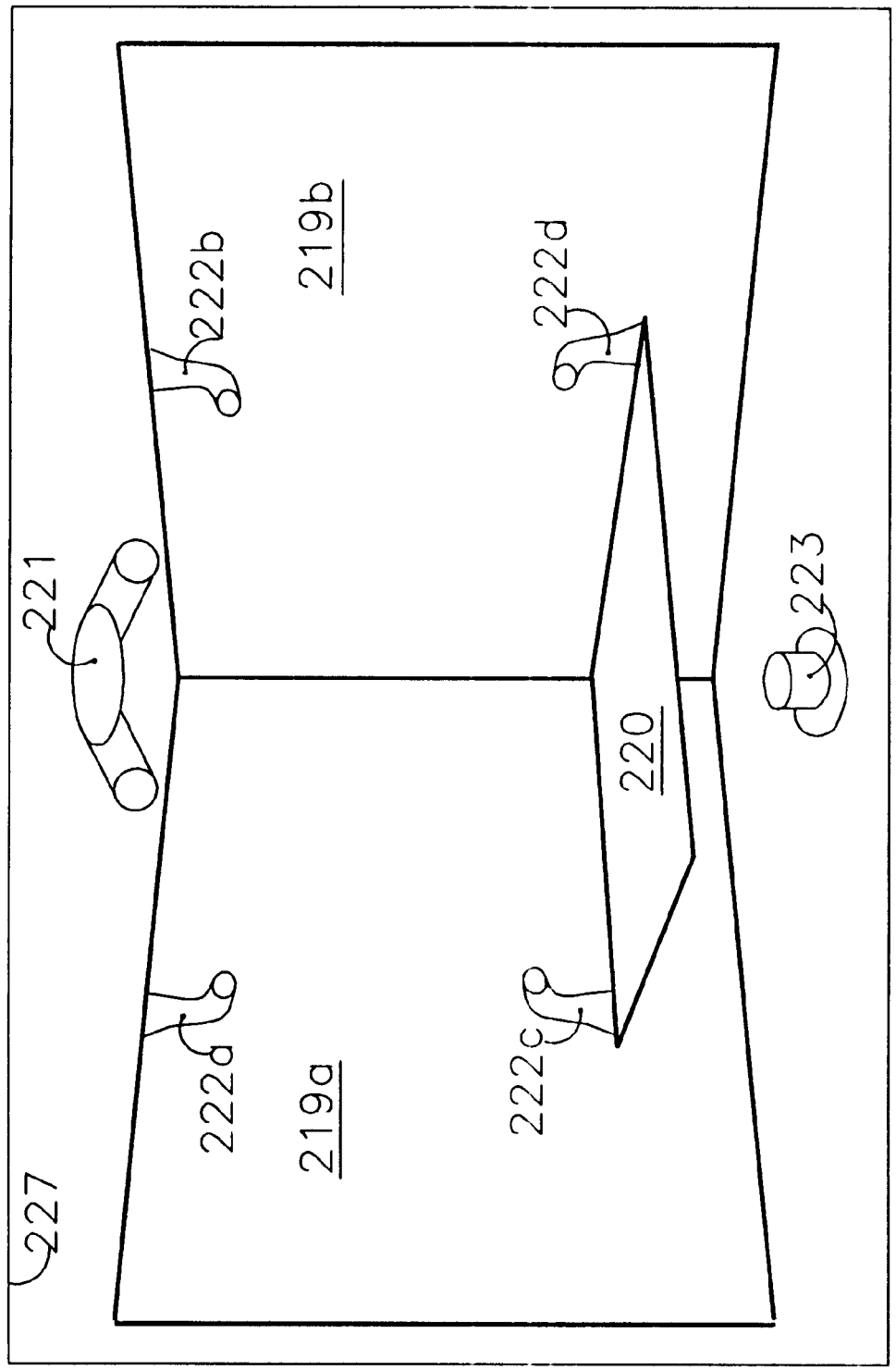
FIG. 21 is a depiction of an ASSDM Cybersymbolic facilitator telecubicle, according to the invention.

The invention also provides unique psycho-symbolic and psycho-dramatic services via the internet world wide web (WWW), the ASSDM ISP and its cyber center. Located at the cyber center are one or more telecubicles. Referring to FIG. 21, there is provided a specially constructed telecubicle 227 whereby a live ASSDM trained facilitator interacts with the participant via the internet, and the aforementioned PPC interactive system. There is provided large front projector 221, or rear and or LCD configured screens 219a, 219b and 200 that display the participant's face. The facilitators face is therefore pick up by one to four cameras 222a, 222b, 222c and 222d. There is also provided a floor projector 223 that displays a participant's face on the desk like screen 220. There is also provided interactive audio apparatus that support the discussions between the ASSDM facilitator and the participant. This is particularly useful for one-on-one therapy that can take place between a participant whom may be located on the other side of the world. This system is especially useful for interviews of new participant's who is experiencing the aforementioned first stages of the ASSDM experience. Therefore, the first explorative stages of the ASSDM experience can be enabled via the internet world wide web (WWW).

The invention provides the aforementioned cyber center. The cyber center is an internet based facility that encompasses the highest quality video and audio production facilities that enable real time multi-participant interactive psycho-symbolic and psycho-dramatic therapy. This cyber center allows for one or many participant's to interact with a live facilitator or with a computer generated facilitator-psycho-symbolic character. The cyber center coupled with the internet based real time video and audio equipment that is further enabled by specially configured PPCs creates a cyber 'theater-in-the-round.'

With reference now to FIG. 19, there is provided a specially designed cyber center 228 that comprises of cutting edge digital video and audio equipment and real time production control. This system is basically an expanded AMV multi-media system that serves multiple participant's via the internet instead of just one participant. Additionally, a live facilitator can interact with multiple participants within the ASSDM virtual world. In fact he can be in a tactile position wheel 152 as depicted in FIG. 4, or sit in the invention holochair 107 which is interfaced with the cyber center 244, and its production control center 178 as depicted in FIG. 5. These unique configurations can enable interaction with multiple participants in cyber space via a computer generated hypertext environment in real time. Therefore each participant can become a morphed character, and the facilitator interacts with each character while flying through or sitting in a computer generated world that each participant is experiencing via his internet based PPC. An HMD can be interfaced with the participants PPC, whereby he too can be immersed with a single participant or with many other participants along with the facilitator, and benefit from these intense psycho-symbolic services via the internet.

Therefore, the cyber center 228 comprises of multiple multimedia storage and transport systems 179, and multiple media computers and main computers 108. There is also provided real time video and audio internet source switching and routing apparatus 234, additional cyber center AMV apparatus interface 244. All of this equipment is controlled by the main computers and the inventions cue and synchronized control system 242. There is provided multiple televisor walls 230a, 230b, 230c, 230d, 230e, 230f, and 230g. There is also provided a special servo and motor controlled stage 232 that rotates around a stationary center stage 231. The facilitator can stand or sit in the center stationary stage 231, while outer movable stage rotates 245 upon manual command from ASSDM cyber center production personnel or automatic command and control via the main computer 108 and the cue and synchronizing system 242. Attached to this rotating stage are four digital video cameras 233a, 233b 233c and 233d that rotate with the stage to capture the best position of the facilitator. An AMV apparatus such as the tactile position wheel 152 can also be placed in the center stage 231 as depicted in FIG. 4, or the holochair 107 as depicted in FIG. 5 whereby it is interface with the cyber center 244.

In FIG. 20, the cyber center 228 and its televisor walls 230a, 230b, 230c, 230d, 230e, 230f and 230g can contain and project multiple participants in each square 235. Therefore dozens of participants can be linked together in interactive multimedia 'chat' groups whereby each group is dealing with similar metaphorical-therapeutic-intent based ASSDM techniques.

The invention also provides a portable battery powered, and wearable 'consciousness machine.' Referring to FIG. 16, in many ways the invention's 'wearable 'consciousness machine' (CM) 209 resembles conventional wearable personal computers and other such apparatus developed in the late 80's and early 90's. However this system comprises software, firmware and hardware means that enable the inventions symbolic quest (SQ) prescriptions are programs that enable the user or participant's metaphorical-therapeutic-intent. The CM 209 is designed to accept DVDs, or conventional CD-ROMS and recordable compact disks. Contained within the DVD or CD-ROMs are symbolic quest (SQ) programs that can be purchased at an ASSDM center, or from a special dealer that distributes ASSDM consumer based products. Additionally, the CM 209 can be interfaced 217 with a PPC via its RS232 multipin port 210 and new symbolic quest (SQ) prescription programs can be down loaded from the internet world wide web (WWW), that is connected to the ASSDM cyber center's ISP.

The ISP is interconnected with special multimedia storage systems that are dedicated for internet multimedia access. The CM 209 has a power button, 212 a scrollable alpha numeric menu that is displayed via the supplied CRT visors 206 which are configured in the same way as the HMD displays 112a depicted in FIG. 6. However, the CRT visor 206 does not have the complete immersive characteristic, as does the aforementioned HMD. A recordable compact disk 208 can be inserted in the designated slot 216, and a new symbolic-prescription can be downloaded and played back on the CM 209 or in any other deck that is compatible with the recordable compact disk format. There is also provided headphones 207 to listen to the audio portion of the symbolic prescription. There is also provided an optional data glove 76 so that the participant can interact with object oriented virtual reality immersion programs that require participant interaction.

There is also provided a cellular telephone, and or a personal communication system (PCS) and or satellite transceiver 211, and wireless antenna 218 that is specially configured to accept real video and audio symbolic prescriptions that are delivered via a currently serving wireless network. These wireless networks are specially integrated and connected to the invention's cyber center and ISP, via the internet world wide web (WWW) and the associated wireline signaling and communications networks. There are new satellite networks such as many planned and currently operating low earth orbit (LEO) systems that can enable the invention's wireless services. Satellite systems such as the Orbcomm LEO network that provide downlink data rates such as 25,000 bps, in fact can enable robust real time transmission of video and audio symbolic-prescriptions to a plurality of participant's via their cellular, PCS and or satellite compatible consciousness machine (CM) 209. Other satellite systems such as Microsoft's Teledesic and Motorola's Iridium satellite networks can also be used for uplink and downlink access to the invention's cyber center, and the participant's consciousness machine (CM) 209. Direct broadcast satellite (DBS) networks that operate on K, KU and Ka band can also deliver real time video and audio prescriptions.

The Inmarsat mobile satellite communications can also enable the invention's conscious machine (CM) 209 in the same manner as the Orbcomm satellite system. The signaling side or back end of all of these cellular, PCS and satellite networks can be integrated to the invention's cyber center via the internet TCP/IP architecture. Such network systems as signaling system seven (SS7) network, asynchronous transfer mode (ATM), T-carriers, via a dedicated data link to the public switched telephone network (PSTN), or via a virtual packet switched connectionless wireline network are also envisioned for use with the present invention.

The aforementioned wireless and wireline networks can enable and enhance the invention's wireless symbolic-prescription delivery. One wireline and wireless based communications platform is called asynchronous transfer mode (ATM). This system can be used to transport digital video and audio based symbolic-prescriptions via wireline terrestrial networks, and wireless space segment satellite networks. The present invention provides for the integration of high-speed data based ATM architecture that enables delivery of real time audio and video to the consciousness machine (CM) 209. In the future, ATM will be used for wireline and air interface protocols and modulation schemes used in cellular, PCS and broadband wireless networks. The inventions will use these ATM based systems as well.

Figure 22:
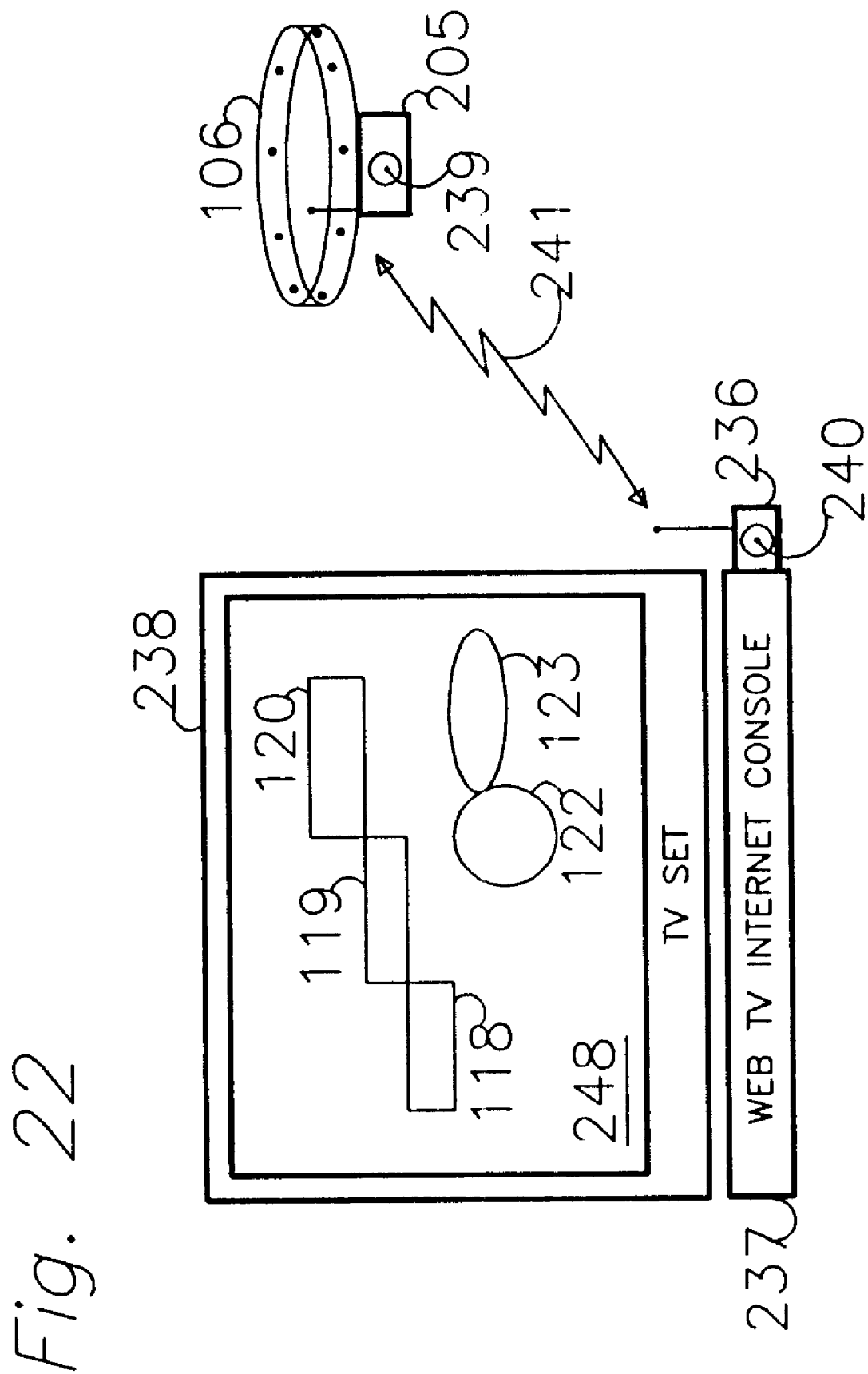
FIG. 22 depicts the invention's wireless EEG transmitter in relation to the personal computer WEB TV platform, according to the invention.

Referring to FIG. 22, the invention also provides for real time interaction with a specially configured WEB TV console 237 that is connected to a conventional television monitor 238. Attached and fully integrated with the WEB TV console 27 is a wireless or infrared 240 based transceiver 236. The radio or infrared signal 241 interacts with a compatible and wearable EEG headband 106 that has an attached battery powered EEG reader 205, that is also capable of transmitted EEG information in infrared data protocols 239. Depicted on the CRT screen 248 of the WEB TV system are the same basic symbols 118, 119, 120, 122 and 123 that are depicted in FIG. 6 and also represent the exact same embodied processes and procedures. Referring to FIG. 22, therefore, the aforementioned symbols and the system processes have previously been described. Therefore, further detailed description of the process need not be explained.

In FIG. 16, various selections can be viewed via the CRT scrolled while viewing the CRT/LCD visors 206 and controlled by the up button 213 and the down button 214. There is also provided EGG sensing headband 106 that can be technically integrated with the CRT/LCD visors 106 or kept separately. There is also provided a specialized battery powered EEG communicator 205 and a wireless radio antenna 224 that communicates via wireless with the CM 209 and detects and transmits brain wave information to the CM 209. The EEG information is then relayed to the currently serving wireless network that in turn relays it the cyber center via conventional telephony signaling means, and or via the internet world wide web (WWW). The aforesaid wireless EEG information is managed in the same aforementioned way as the PPC interface. There is also provided the aforementioned Private Eye display system 247 that can be used instead of the CRT/LCD visor or HMD.

In FIG. 7, the invention also enables an additional feature to its novel means, methods and apparatus. A cyberscanning system may be used to scan the physical characteristic of any person's face and full body. All that the user needs to do is to sit or sand and be scanned for about 17 seconds. This system is currently begin used for such applications as scanning and digitizing the physical likeness of celebrities and others into a computer data base. Once stored, these images can be used to create computer-animated characters for films and videos. In effect, these images can be sued to recreate the actor or celebrity and animate him so that he can become a cyberactor that is a life-like reflection and expression of the real person. The present invention uses this type of cyberware technique, software, and hardware means to scan in the likeness of any participant.

The SCr 128 may embody the true likeness of the participant 145, so that in effect, the participant can have psycho-symbolic dialogues and interactions with himself as a mirror image in cyberspace. Certain key aspects of the participant's metaphorical-therapeutic-intent can be profoundly served using the cyber method and adapting it to the invention's means, methods and apparatus as previously described. This maybe an especially effective therapeutic tool when used within the framework of the present invention's stages. Furthermore, by scanning the participant's likeness into the ASSDM image storage and retrieval systems, the computer generated and animated likeness can be inserted within the narrative of many symbolic pathways (SP) that are embodied in selected symbolic quests (SQ). The participant can therefore experience himself as a reflection of the potential self being transformed before his senses. The participant's voice, speech patterns, facial expressions and other familiar personal hallmarks may be integrated into a selected symbolic quest (SQ) and played back to the participant. Furthermore, the participant can be immersed into a choice driven cyber-hypertext journey that is governed by the inventions artificial intelligence means (AI). The AMV technological event can be used by the participant to truly face negative aspects of his own behavior, and simultaneously discover ways to overcome and replace these negative characteristics with positive characteristics. By looking at himself 145 as depicted in FIG. 7, and directly and completely interact with himself via deep dialogs and other means, he can rapidly overcome all sorts of dysfunctional behavior.

This mirrored transformative experience also acts as a transcendent function that causes the participant to embody the characteristics that are embodied in the narrative structure transpiring in real time before his senses where he is the main character. The participant therefore becomes the reflection of himself that he experiences in real time before him. Furthermore, this cyberware scanning approach that closely approximates photorealism is an important component for producing the inventions symbolic prescriptions and utilizing them over the internet, and via the inventions consciousness machine. This innovative approach to using cyberscanning can utterly reinforce the participants metaphorical-therapeutic-intent. Also, the psycho-dramatic-therapeutic potential of this technique has clear potential for the participant to know himself firsthand while dialoging with and acting out positive and negative aspects of his personality. Furthermore, the participant can see himself as a main character of his own symbolic quest (SC) and deeply participate with his own transformative journey.

For example, in FIG. 14, the wizard 88 can have an accurate likeness of the participants face and body gestures in order to deeply reinforce the participant's metaphorical-therapeutic-intent while experiencing the metaphorical tension (MT) 79 that is an inherent component of the symbolic quest (SQ). Furthermore, the invention's physiological measurement means and methods can be used to measure the aforementioned stress. In addition, the inventions electroocoulosymbolic means and methods can be used to embed the aforementioned hidden pulses within the substrate of the symbolic construct (SC) content, that is further embodied in a selected symbolic pathway (SP) that comprises the symbolic quest (SQ)

Additional object and advantages of the present invention will readily occur to those skilled in the art. The electrooculosymbolic system can be utilized by television advertiser's in order to gauge what a viewer is watching at a particular time. In addition, the invention will measure how he is emotionally responding to the programming content. This is accomplished by mapping the received brain wave information. Is the viewer experiencing pleasure or not? The results can be transmitted via the internet to data collection center. Therefore, the invention in its broader aspects is not limited to the specific details, representative devices, and illustrative examples shown and described. Accordingly, departures may be made from such details without departing from the spirit or scope of the general invention's means and methods defined by the appended claims and their equivalents.

What is claimed is:

1. An apparatus for behavior modification and memory enhancement, comprising:

means for evaluating and constructing a symbolic profile of a subject participant;

means for interpreting said subject participants stored symbolic constructs;

virtual reality instruction means for instructing the participant in behavior and memory modification;

means for evaluating and recording physiologic parameters of the subject participant and delivering symbolic containers to the participant; and means for delivery of symbolic prescriptions to said participant.

2. The apparatus of claim 1, wherein said symbolic prescriptions are delivered to said participant via the internet.

3. A method for accessing and recognition of stored memory symbolic constructs, comprising:

isolating symbolic quests embodied within multiple multimedia virtual reality events;

delivering said multimedia virtual reality events to a user by artificial intelligence and multi-media means;

applying said symbolic constructs to said user.

4. The method for accessing and recognition of stored memory symbolic constructs of claim 3, wherein said symbolic constructs are embodied within symbolic containers.

5. The method for accessing and recognition of stored memory symbolic constructs of claim 4, wherein said symbolic containers are contained within said multiple multimedia virtual reality events.

6. The method for accessing and recognition of stored memory symbolic constructs of claim 3, wherein said multiple multimedia virtual reality events are cued by biologial sensor signals.

7. The method for accessing and recognition of stored memory symbolic constructs of claim 3, wherein said multiple multimedia virtual reality events are linear sequences.

8. The method for accessing and recognition of stored memory symbolic constructs of claim 3, wherein said multiple multimedia virtual reality events are non-linear sequences.

9. The method for accessing and recognition of stored memory symbolic constructs of claim 7, wherein said linear sequences comprise life event scenarios.

10. The method for accessing and recognition of stored memory symbolic constructs of claim 3, wherein said symbolic quests are configured and delivered in a planned and arranged symbolic quest.

11. The method for accessing and recognition of stored memory symbolic constructs of claim 3, wherein said symbolic quests are configured and delivered in a randomly arranged symbolic quest.

12. The method for accessing and recognition of stored memory symbolic constructs of claim 3, wherein further including the step of retreivieng and measuring data from biological signal sensors.

13. The method for accessing and recognition of stored memory symbolic constructs of claim 3, wherein said symbolic constructs are associated symbolic constructs.

14. The method for accessing and recognition of stored memory symbolic constructs of claim 3, wherein said symbolic constructs are non-associated symbolic constructs.

15. The method for accessing and recognition of stored memory symbolic constructs of claim 3, wherein said symbolic constructs are singular symbolic constructs.

* * * * *